US005795723A

United States Patent [19]
Tapscott et al.

[11] Patent Number: 5,795,723
[45] Date of Patent: Aug. 18, 1998

[54] EXPRESSION OF NEUROGENIC BHLH GENES IN PRIMITIVE NEUROECTODERMAL TUMORS

[75] Inventors: Stephen J. Tapscott; James M. Olson. both of Seattle, Wash.

[73] Assignee: Fred Hutchinson Cancer Research Center, Seattle, Wash.

[21] Appl. No.: 910,973

[22] Filed: Aug. 7, 1997

Related U.S. Application Data

[63] Continuation-in-part of Ser. No. 552,142, Nov. 2, 1995, Pat. No. 5,695,995, which is a continuation-in-part of Ser. No. 239,238, May 6, 1994, abandoned.

[51] Int. Cl.$^6$ .............................. C12Q 1/68; C12Q 1/04; C12P 21/02; C07H 21/04
[52] U.S. Cl. .............................. 435/6; 435/34; 435/69.1; 536/23.1
[58] Field of Search .............................. 435/6, 29, 325, 435/34, 69.1, 69.4, 172.3, 257.33, 320.1, 357, 360; 536/23.1, 23.5, 23.51

[56] References Cited

U.S. PATENT DOCUMENTS

| | | | |
|---|---|---|---|
| 5,302,519 | 4/1994 | Blackwood et al. | 435/69.1 |
| 5,322,801 | 6/1994 | Kingston et al. | 436/501 |
| 5,352,595 | 10/1994 | Tapscott et al. | 435/172.3 |
| 5,695,995 | 12/1997 | Weintraub et al. | 435/325 |

OTHER PUBLICATIONS

Maniatis et al., "Molecular cloning: A Laboratory Manual." Cold Spring Harbor Laboratory. Cold Spring Harbor, NY, 1982. p. 227.
Wilson, P.A. et al., "Induction of epidermis and inhibition of neural fate by Bmp–4," *Nature*, 376:331–333 (1995).
Lee, J.E. et al., "Conversion of Xenopus Ectoderm into Neurons by NeuroD, a Basic Helix–Loop–Helix Protein," *Science*, 268:836–844 (1995).
Shimizu, C. et al., "MATH–2, a mammalian helix–loop–helix factor structurally related to the product of Drosophila proneural gene atonal, is specifically expressed in the nervous system," *Eur. J. Biochem.*, 229:239–248 (1995).
Naya, F.J. et al., "Tissue-specific regulation of the insulin gene by a novel basic helix–loop–helix transcription factor," *Genes and Development*, 9:1009–1019 (1995).
Singson, A. et al., "Direct downstream targets of proneural activators in the imaginal disc include genes involved in lateral inhibitory signaling," *Genes & Development*, 8:2058–2071 (1994).
Turner, D.L. et al., "Expression of achaete–scute homolog 3 in Xenopus embryos converts ectodermal cells to a neural fate," *Genes & Development*, 8:1434–1447 (1994).
Rupp. R.A.W. et al., "Xenopus embryos regulate the nuclear localization of XMyoD." *Genes & Development*, 8:1311–1323 (1994).

Buffinger, N. et al., "Myogenic specification in somites: induction by axial structures," *Development*, 120:1443–1452 (1994).
Kramatschek, B. et al., "Neuroectodermal transcription of the Drosophila neurogenic genes E(spl) and HLH–m5 is regulated by proneural genes," *Development*, 120:815–826 (1994).
Burcin, M. et al., "Factors influencing nuclear receptors in transcriptional repression," *Cancer Biology*, 5:337–346 (1994).
Rudnicki, M.A. et al., "MyoD or Myf–5 Is Required for the Formation of Skeletal Muscle," *Cell*, 75:1351–1359 (1993).
Guillemot, F. et al., "Mammalian *achaete–scute* Homolog 1 Is Required for the Early Development of Olfactory and Autonomic Neurons," *Cell*, 75:463–476 (1993).
Lamb. T.M. et al., "Neural Induction by the Secreted Polypeptide Noggin," *Science*, 262:713–718 (1993).
Hasty, P. et al., "Muscle deficiency and neonatal death in mice with a targeted mutation in the myogenin gene," *Nature*, 364:501–506 (1993).
Nabeshima, Y. et al., "Myogenin gene disruption results in perinatal lethality because of severe muscle defect," *Nature*, 364:532–535 (1993).
Guillemot, F. et al., "Dynamic expression of the murine *Achaete–Scute* homologue *Mash–1* in the developing nervous system," *Mechanisms of Development*, 42:171–185 (1993).
Rong, P.M et al., "The neural tube/notochord complex is necessary for vertebral but not limb and body wall striated muscle differentiation," *Development*, 115:657–672 (1992).
Lo, L.C. et al., "Mammalian *achaete–scute* homolog 1 is transiently expressed by spatially restricted subsets of early neuroepithelial and neural crest cells," *Genes & Development*, 5:1524–1537 (1991).
Blackwood, E.M. et al., "Max: A Helix–Loop–Helix Zipper Protein That Forms a Sequence–Specific DNA–Binding Complex with Myc." *Science*, 251:1211–1217 (1991).
Johnson, J.E. et al., "Two rat homologues of *Drosophila achaete–scute* specifically expressed in neuronal precursors," *Nature*, 346:858–861 (1990).
Gobel et al., "NSCL–2: A Basic Domain Helix–Loop–Helix Gene Expressed in Early Neurogenesis," *Cell Growth and Diff.*, 3:143–148 (1992).
Ball, D.W. et al., "Identification of a Human *Achaete–Schute* Homolog Highly Expressed in Neuroendocrine Tumors," *Proc. Natl. Acad. Sci. USA*, 90:5648–5652 (1993).

(List continued on next page.)

*Primary Examiner*—Nancy Degen
*Attorney, Agent, or Firm*—Christensen O'Connor Johnson & Kindness PLLC

[57] ABSTRACT

Provided are methods of classifying and prognosticating human neuroectodermal tumors by analyzing a sample of the tumor to determine whether various bHLH proteins are detectably expressed in the sample. In the methods disclosed herein, expression of the bHLH genes is assessed by measuring transcripts or proteins expressed from the genes.

6 Claims, No Drawings

OTHER PUBLICATIONS

Biegel, J.A. et al., "Isochromosome 17q Demonstrated by Interphase Fluorescence In Situ Hybridization in Primitive Neuroectodermal Tumors of the Central Nervous System," *Genes, Chromo. & Cancer,* 14:85–96 (1995).

Trojanowski, J.Q. et al., "Medulloblastomas and Related Privitive Neuroectodermal Brain Tumors of Childhood Recapitulate Molecular Milestones in the Maturation of Neuroblasts," *Mol. & Chem. Neuro.,* 17:121–135 (1992).

Schütz, B.R. et al., "Mapping of Chromosomal Gains and Losses in Primitive Neuroectodermal Tumors by Comparative Genomic Hybridization," *Genes, Chromo. & Cancer,* 16:196–203 (1996).

Kozmik, Z. et al., "Deregulated Expression of PAX5 in Medulloblastoma," *Proc. Natl. Acad. Sci. USA,* 92:5709–5713 (1995).

Clark, J. et al., "Expression of Members of the MYF Gene Family in Human Rhabdomyosarcomas," *Br. J. Cancer,* 64:1039–1042 (1991).

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 2089 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Mus musculus ( i x ) FEATURE:
        ( A ) NAME/KEY: CDS
        ( B ) LOCATION: 229..1302

( x i ) SEQUENCE DESCRIPTION: SEQ ID NO:1:

```
ACTACGCAGC  ACCGAGGTAC  AGACACGCCA  GCATGAAGCA  CTGCGTTTAA  CTTTTCCTGG       60

AGGCATCCAT  TTTGCAGTGG  ACTCCTGTGT  ATTTCTATTT  GTGTGCATTT  CTGTAGGATT      120

AGGGAGAGGG  AGCTGAAGGC  TTATCCAGCT  TTTAAATATA  GCGGGTGGAT  TTCCCCCCCT      180

TTCTTCTTCT  GCTTGCCTCT  CTCCCTGTTC  AATACAGGAA  GTGGAAAC ATG ACC AAA        237
                                                         Met Thr Lys
                                                           1

TCA TAC AGC GAG AGC GGG CTG ATG GGC GAG CCT CAG CCC CAA GGT CCC            285
Ser Tyr Ser Glu Ser Gly Leu Met Gly Glu Pro Gln Pro Gln Gly Pro
    5              10                  15

CCA AGC TGG ACA GAT GAG TGT CTC AGT TCT CAG GAC GAG GAA CAC GAG            333
Pro Ser Trp Thr Asp Glu Cys Leu Ser Ser Gln Asp Glu Glu His Glu
 20              25                  30                      35

GCA GAC AAG AAA GAG GAC GAG CTT GAA GCC ATG AAT GCA GAG GAG GAC            381
Ala Asp Lys Lys Glu Asp Glu Leu Glu Ala Met Asn Ala Glu Glu Asp
            40                  45                  50

TCT CTG AGA AAC GGG GGA GAG GAG GAG GAA GAT GAG GAT CTA GAG                429
Ser Leu Arg Asn Gly Gly Glu Glu Glu Glu Glu Asp Glu Asp Leu Glu
                55                  60                  65

GAA GAG GAG GAA GAA GAA GAG GAG GAG GAG GAT CAA AAG CCC AAG AGA            477
Glu Glu Glu Glu Glu Glu Glu Glu Glu Glu Asp Gln Lys Pro Lys Arg
            70                  75                  80

CGG GGT CCC AAA AAG AAA AAG ATG ACC AAG GCG CGC CTA GAA CGT TTT            525
Arg Gly Pro Lys Lys Lys Lys Met Thr Lys Ala Arg Leu Glu Arg Phe
        85                  90                  95

AAA TTA AGG CGC ATG AAG GCC AAC GCC CGC GAG CGG AAC CGC ATG CAC            573
Lys Leu Arg Arg Met Lys Ala Asn Ala Arg Glu Arg Asn Arg Met His
100                 105                 110                 115

GGG CTG AAC GCG GCG CTG GAC AAC CTG CGC AAG GTG GTA CCT TGC TAC            621
Gly Leu Asn Ala Ala Leu Asp Asn Leu Arg Lys Val Val Pro Cys Tyr
                    120                 125                 130

TCC AAG ACC CAG AAA CTG TCT AAA ATA GAG ACA CTG CGC TTG GCC AAG            669
Ser Lys Thr Gln Lys Leu Ser Lys Ile Glu Thr Leu Arg Leu Ala Lys
                135                 140                 145

AAC TAC ATC TGG GCT CTG TCA GAG ATC CTG CGC TCA GGC AAA AGC CCT            717
Asn Tyr Ile Trp Ala Leu Ser Glu Ile Leu Arg Ser Gly Lys Ser Pro
            150                 155                 160

GAT CTG GTC TCC TTC GTA CAG ACG CTC TGC AAA GGT TTG TCC CAG CCC            765
Asp Leu Val Ser Phe Val Gln Thr Leu Cys Lys Gly Leu Ser Gln Pro
        165                 170                 175
```

-continued

| | | | | | | | | | | | | | | | | |
|---|---|---|---|---|---|---|---|---|---|---|---|---|---|---|---|---|
| ACT | ACC | AAT | TTG | GTC | GCC | GGC | TGC | CTG | CAG | CTC | AAC | CCT | CGG | ACT | TTC | 813 |
| Thr | Thr | Asn | Leu | Val | Ala | Gly | Cys | Leu | Gln | Leu | Asn | Pro | Arg | Thr | Phe | |
| 180 | | | | 185 | | | | | 190 | | | | | | 195 | |
| TTG | CCT | GAG | CAG | AAC | CCG | GAC | ATG | CCC | CCG | CAT | CTG | CCA | ACC | GCC | AGC | 861 |
| Leu | Pro | Glu | Gln | Asn | Pro | Asp | Met | Pro | Pro | His | Leu | Pro | Thr | Ala | Ser | |
| | | | | 200 | | | | | 205 | | | | | 210 | | |
| GCT | TCC | TTC | CCG | GTG | CAT | CCC | TAC | TCC | TAC | CAG | TCC | CCT | GGA | CTG | CCC | 909 |
| Ala | Ser | Phe | Pro | Val | His | Pro | Tyr | Ser | Tyr | Gln | Ser | Pro | Gly | Leu | Pro | |
| | | | 215 | | | | | 220 | | | | | 225 | | | |
| AGC | CCG | CCC | TAC | GGC | ACC | ATG | GAC | AGC | TCC | CAC | GTC | TTC | CAC | GTC | AAG | 957 |
| Ser | Pro | Pro | Tyr | Gly | Thr | Met | Asp | Ser | Ser | His | Val | Phe | His | Val | Lys | |
| | | 230 | | | | 235 | | | | | 240 | | | | | |
| CCG | CCG | CCA | CAC | GCC | TAC | AGC | GCA | GCT | CTG | GAG | CCC | TTC | TTT | GAA | AGC | 1005 |
| Pro | Pro | Pro | His | Ala | Tyr | Ser | Ala | Ala | Leu | Glu | Pro | Phe | Phe | Glu | Ser | |
| | 245 | | | | 250 | | | | | 255 | | | | | | |
| CCC | CTA | ACT | GAC | TGC | ACC | AGC | CCT | TCC | TTT | GAC | GGA | CCC | CTC | AGC | CCG | 1053 |
| Pro | Leu | Thr | Asp | Cys | Thr | Ser | Pro | Ser | Phe | Asp | Gly | Pro | Leu | Ser | Pro | |
| 260 | | | | | 265 | | | | | 270 | | | | | 275 | |
| CCG | CTC | AGC | ATC | AAT | GGC | AAC | TTC | TCT | TTC | AAA | CAC | GAA | CCA | TCC | GCC | 1101 |
| Pro | Leu | Ser | Ile | Asn | Gly | Asn | Phe | Ser | Phe | Lys | His | Glu | Pro | Ser | Ala | |
| | | | | 280 | | | | | 285 | | | | | 290 | | |
| GAG | TTT | GAA | AAA | AAT | TAT | GCC | TTT | ACC | ATG | CAC | TAC | CCT | GCA | GCG | ACG | 1149 |
| Glu | Phe | Glu | Lys | Asn | Tyr | Ala | Phe | Thr | Met | His | Tyr | Pro | Ala | Ala | Thr | |
| | | | 295 | | | | | 300 | | | | | 305 | | | |
| CTG | GCA | GGG | CCC | CAA | AGC | CAC | GGA | TCA | ATC | TTC | TCT | TCC | GGT | GCC | GCT | 1197 |
| Leu | Ala | Gly | Pro | Gln | Ser | His | Gly | Ser | Ile | Phe | Ser | Ser | Gly | Ala | Ala | |
| | | 310 | | | | | 315 | | | | | 320 | | | | |
| GCC | CCT | CGC | TGC | GAG | ATC | CCC | ATA | GAC | AAC | ATT | ATG | TCT | TTC | GAT | AGC | 1245 |
| Ala | Pro | Arg | Cys | Glu | Ile | Pro | Ile | Asp | Asn | Ile | Met | Ser | Phe | Asp | Ser | |
| | 325 | | | | | 330 | | | | | 335 | | | | | |
| CAT | TCG | CAT | CAT | GAG | CGA | GTC | ATG | AGT | GCC | CAG | CTT | AAT | GCC | ATC | TTT | 1293 |
| His | Ser | His | His | Glu | Arg | Val | Met | Ser | Ala | Gln | Leu | Asn | Ala | Ile | Phe | |
| 340 | | | | | 345 | | | | | 350 | | | | | 355 | |

| | | | | | |
|---|---|---|---|---|---|
| CAC | GAT | TAGAGGGCAC | GTCAGTTTCA | CTATTCCCGG | GAAACGAATC | CACTGTGCGT | 1349 |
| His | Asp | | | | | |

| | | | | | |
|---|---|---|---|---|---|
| ACAGTGACTG | TCCTGTTTAC | AGAAGGCAGC | CCTTTTGCTA | AGATTGCTGC | AAAGTGCAAA | 1409 |
| TACTCAAAGC | TTCAAGTGAT | ATATGTATTT | ATTGTCGTTA | CTGCCTTTGG | AAGAAACAGG | 1469 |
| GGATCAAAGT | TCCTGTTCAC | CTTATGTATT | GTTTCTATA | GCTCTTCTAT | TTTAAAAATA | 1529 |
| ATAATACAGT | AAAGTAAAAA | AGAAAATGTG | TACCACGAAT | TCGTGTAGC | TGTATTCAGA | 1589 |
| TCGTATTAAT | TATCTGATCG | GGATAAAAAA | AATCACAAGC | AATAATTAGG | ATCTATGCAA | 1649 |
| TTTTTAAACT | AGTAATGGGC | CAATTAAAAT | ATATATAAAT | ATATATTTTT | CAACCAGCAT | 1709 |
| TTTACTACCT | GTGACCTTTC | CCATGCTGAA | TTATTTTGTT | GTGATTTGT | ACAGAATTTT | 1769 |
| TAATGACTTT | TTATAACGTG | GATTTCCTAT | TTAAAACCA | TGCAGCTTCA | TCAATTTTTA | 1829 |
| TACATATCAG | AAAAGTAGAA | TTATATCTAA | TTTATACAAA | ATAATTTAAC | TAATTTAAAC | 1889 |
| CAGCAGAAAA | GTGCTTAGAA | AGTTATTGCG | TTGCCTTAGC | ACTTCTTTCT | TCTCTAATTG | 1949 |
| TAAAAAGAA | AAAAAAAAA | AAAAACTCG | AGGGGGGGCC | CGGTACCCAG | CTTTTGTTCC | 2009 |
| CTTTAGTGAG | GGTTAATTGC | GCGCTTGGCG | TAATCATGGT | CATAGCTGTT | TCCTGTGTGA | 2069 |
| ATTGTTATCC | GCTCACAATT | | | | | 2089 |

( 2 ) INFORMATION FOR SEQ ID NO:2:

( i ) SEQUENCE CHARACTERISTICS:
        ( A ) LENGTH: 357 amino acids
        ( B ) TYPE: amino acid (D) TOPOLOGY: linear (ii) MOLECULE TYPE: protein (xi) SEQUENCE DESCRIPTION: SEQ ID NO:2:

```
Met Thr Lys Ser Tyr Ser Glu Ser Gly Leu Met Gly Glu Pro Gln Pro
 1               5                  10                  15
Gln Gly Pro Pro Ser Trp Thr Asp Glu Cys Leu Ser Ser Gln Asp Glu
              20                  25                  30
Glu His Glu Ala Asp Lys Lys Glu Asp Glu Leu Glu Ala Met Asn Ala
          35                  40                  45
Glu Glu Asp Ser Leu Arg Asn Gly Gly Glu Glu Glu Glu Glu Asp Glu
      50                  55                  60
Asp Leu Glu Glu Glu Glu Glu Glu Glu Glu Glu Glu Asp Gln Lys
 65                  70                  75                  80
Pro Lys Arg Arg Gly Pro Lys Lys Lys Met Thr Lys Ala Arg Leu
                  85                  90                  95
Glu Arg Phe Lys Leu Arg Arg Met Lys Ala Asn Ala Arg Glu Arg Asn
              100                 105                 110
Arg Met His Gly Leu Asn Ala Ala Leu Asp Asn Leu Arg Lys Val Val
          115                 120                 125
Pro Cys Tyr Ser Lys Thr Gln Lys Leu Ser Lys Ile Glu Thr Leu Arg
      130                 135                 140
Leu Ala Lys Asn Tyr Ile Trp Ala Leu Ser Glu Ile Leu Arg Ser Gly
145                 150                 155                 160
Lys Ser Pro Asp Leu Val Ser Phe Val Gln Thr Leu Cys Lys Gly Leu
                  165                 170                 175
Ser Gln Pro Thr Thr Asn Leu Val Ala Gly Cys Leu Gln Leu Asn Pro
              180                 185                 190
Arg Thr Phe Leu Pro Glu Gln Asn Pro Asp Met Pro Pro His Leu Pro
          195                 200                 205
Thr Ala Ser Ala Ser Phe Pro Val His Pro Tyr Ser Tyr Gln Ser Pro
      210                 215                 220
Gly Leu Pro Ser Pro Pro Tyr Gly Thr Met Asp Ser Ser His Val Phe
225                 230                 235                 240
His Val Lys Pro Pro Pro His Ala Tyr Ser Ala Ala Leu Glu Pro Phe
                  245                 250                 255
Phe Glu Ser Pro Leu Thr Asp Cys Thr Ser Pro Ser Phe Asp Gly Pro
              260                 265                 270
Leu Ser Pro Pro Leu Ser Ile Asn Gly Asn Phe Ser Phe Lys His Glu
          275                 280                 285
Pro Ser Ala Glu Phe Glu Lys Asn Tyr Ala Phe Thr Met His Tyr Pro
      290                 295                 300
Ala Ala Thr Leu Ala Gly Pro Gln Ser His Gly Ser Ile Phe Ser Ser
305                 310                 315                 320
Gly Ala Ala Ala Pro Arg Cys Glu Ile Pro Ile Asp Asn Ile Met Ser
                  325                 330                 335
Phe Asp Ser His Ser His His Glu Arg Val Met Ser Ala Gln Leu Asn
              340                 345                 350
Ala Ile Phe His Asp
          355
```

(2) INFORMATION FOR SEQ ID NO:3:

(i) SEQUENCE CHARACTERISTICS:
(A) LENGTH: 1275 base pairs

-continued ( B ) TYPE: nucleic acid
( C ) STRANDEDNESS: double
( D ) TOPOLOGY: linear ( i i ) MOLECULE TYPE: cDNA ( v i ) ORIGINAL SOURCE:
( A ) ORGANISM: Xenopus laevis ( i x ) FEATURE:
( A ) NAME/KEY: CDS
( B ) LOCATION: 25..1083

( x i ) SEQUENCE DESCRIPTION: SEQ ID NO:3:

```
ATTTCCTTTC TCCAGATCTA AAAA ATG ACC AAA TCG TAT GGA GAG AAT GGG                      51
                           Met Thr Lys Ser Tyr Gly Glu Asn Gly
                            1                   5

CTG ATC CTG GCC GAG ACT CCG GGC TGC AGA GGA TGG GTG GAC GAA TGC                      99
Leu Ile Leu Ala Glu Thr Pro Gly Cys Arg Gly Trp Val Asp Glu Cys
 10              15                  20                  25

CTG AGT TCT CAG GAT GAA AAC GAT CTG GAG AAA AAG GAG GGA GAG TTG                     147
Leu Ser Ser Gln Asp Glu Asn Asp Leu Glu Lys Lys Glu Gly Glu Leu
                 30                  35                  40

ATG AAA GAA GAC GAT GAA GAC TCA CTG AAT CAT CAC AAT GGA GAG GAG                     195
Met Lys Glu Asp Asp Glu Asp Ser Leu Asn His His Asn Gly Glu Glu
             45                  50                  55

AAC GAG GAA GAG GAT GAA GGG GAT GAG GAG GAG GAG GAC GAT GAA GAT                     243
Asn Glu Glu Glu Asp Glu Gly Asp Glu Glu Glu Glu Asp Asp Glu Asp
         60                  65                  70

GAT GAT GAG GAT GAC GAC CAG AAA CCC AAA AGG CGA GGA CCG AAA AAG                     291
Asp Asp Glu Asp Asp Asp Gln Lys Pro Lys Arg Arg Gly Pro Lys Lys
     75                  80                  85

AAA AAA ATG ACG AAA GCC CGG GTG GAG CGA TTT AAA GTG AGA CGC ATG                     339
Lys Lys Met Thr Lys Ala Arg Val Glu Arg Phe Lys Val Arg Arg Met
 90                  95                 100                 105

AAG GCA AAC GCC AGG GAG AGG AAT CGC ATG CAC GGA CTC AAC GAT GCC                     387
Lys Ala Asn Ala Arg Glu Arg Asn Arg Met His Gly Leu Asn Asp Ala
             110                 115                 120

CTG GAC AGT CTG CGC AAA GTT GTG CCC TGC TAC TCC AAA ACA CAA AAG                     435
Leu Asp Ser Leu Arg Lys Val Val Pro Cys Tyr Ser Lys Thr Gln Lys
         125                 130                 135

TTG TCT AAG ATT GAA ACT CTG CGC CTG GCT AAG AAC TAC ATC TGG GCT                     483
Leu Ser Lys Ile Glu Thr Leu Arg Leu Ala Lys Asn Tyr Ile Trp Ala
     140                 145                 150

CTT TCT GAG ATT TTA AGG TCC GGC AAA AGC CCA GAC CTG GTG TCC TTT                     531
Leu Ser Glu Ile Leu Arg Ser Gly Lys Ser Pro Asp Leu Val Ser Phe
 155                 160                 165

GTA CAA ACT CTC TGC AAA GGT TTG TCG CAG CCC ACC ACC AAT CTA GTA                     579
Val Gln Thr Leu Cys Lys Gly Leu Ser Gln Pro Thr Thr Asn Leu Val
170                 175                 180                 185

GCG GGG TGT CTG CAG CTG AAC CCC AGA ACT TTC CTT CCT GAG CAG AGT                     627
Ala Gly Cys Leu Gln Leu Asn Pro Arg Thr Phe Leu Pro Glu Gln Ser
             190                 195                 200

CAG GAC ATC CAG TCG CAC ATG CAA ACA GCG AGC TCT TCC TTC CCT CTG                     675
Gln Asp Ile Gln Ser His Met Gln Thr Ala Ser Ser Ser Phe Pro Leu
         205                 210                 215

CAG GGC TAT CCC TAT CAG TCC CCT GGT CTT CCC AGT CCC CCT TAT GGT                     723
Gln Gly Tyr Pro Tyr Gln Ser Pro Gly Leu Pro Ser Pro Pro Tyr Gly
     220                 225                 230

ACC ATG GAC AGC TCC CAT GTA TTC CAC GTC AAG CCT CAC TCC TAT GGG                     771
Thr Met Asp Ser Ser His Val Phe His Val Lys Pro His Ser Tyr Gly
 235                 240                 245

GCG GCC CTG GAG CCT TTC TTT GAC AGC AGC ACC GTC ACT GAG TGT ACC                     819
```

```
Ala  Ala  Leu  Glu  Pro  Phe  Phe  Asp  Ser  Ser  Thr  Val  Thr  Glu  Cys  Thr
250                 255                      260                      265

AGC  CCG  TCA  TTC  GAT  GGT  CCC  CTG  AGC  CCA  CCC  CTT  AGT  GTT  AAT  GGG    867
Ser  Pro  Ser  Phe  Asp  Gly  Pro  Leu  Ser  Pro  Pro  Leu  Ser  Val  Asn  Gly
                    270                      275                      280

AAC  TTT  ACT  TTT  AAA  CAC  GAG  CAT  TCG  GAG  TAT  GAT  AAA  AAT  TAC  ACG    915
Asn  Phe  Thr  Phe  Lys  His  Glu  His  Ser  Glu  Tyr  Asp  Lys  Asn  Tyr  Thr
                285                      290                      295

TTC  ACT  ATG  CAC  TAT  CCT  GCA  GCC  ACT  ATA  TCC  CAG  GGC  CAC  GGA  CCA    963
Phe  Thr  Met  His  Tyr  Pro  Ala  Ala  Thr  Ile  Ser  Gln  Gly  His  Gly  Pro
           300                      305                      310

TTG  TTC  TCC  ACG  GGG  GGA  CCA  CGC  TGT  GAA  ATC  CCA  ATA  GAC  ACC  ATC   1011
Leu  Phe  Ser  Thr  Gly  Gly  Pro  Arg  Cys  Glu  Ile  Pro  Ile  Asp  Thr  Ile
     315                      320                      325

ATG  TCC  TAT  GAC  GGT  CAC  TCC  CAC  CAT  GAA  AGA  GTC  ATG  AGT  GCC  CAG   1059
Met  Ser  Tyr  Asp  Gly  His  Ser  His  His  Glu  Arg  Val  Met  Ser  Ala  Gln
330                      335                      340                      345

CTA  AAT  GCC  ATC  TTT  CAT  GAT  TAACCCTTGG  AAGATCAAAA  CAACTGACTG            1110
Leu  Asn  Ala  Ile  Phe  His  Asp
                    350

TGCATTGCCA  GGACTGTCTT  GTTTACCAAG  GGCAGACACG  TGGGTAGTAA  AAGTGCAAAT           1170

GCCCCACTCT  GGGGCTGTAA  CAAACTTGAT  CTTGTCCTGC  CTTTAGATAT  GGGGAAACCT           1230

AATGTATTAA  TTCCCACCTC  CTTCCAATCG  ACACTCCTTT  AAATT                            1275
```

( 2 ) INFORMATION FOR SEQ ID NO:4:

( i ) SEQUENCE CHARACTERISTICS:
        ( A ) LENGTH: 352 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Lys  Ser  Tyr  Gly  Glu  Asn  Gly  Leu  Ile  Leu  Ala  Glu  Thr  Pro
 1              5                        10                       15

Gly  Cys  Arg  Gly  Trp  Val  Asp  Glu  Cys  Leu  Ser  Ser  Gln  Asp  Glu  Asn
               20                       25                       30

Asp  Leu  Glu  Lys  Lys  Glu  Gly  Glu  Leu  Met  Lys  Glu  Asp  Asp  Glu  Asp
               35                       40                       45

Ser  Leu  Asn  His  His  Asn  Gly  Glu  Glu  Asn  Glu  Glu  Asp  Glu  Gly
          50                        55                       60

Asp  Glu  Glu  Glu  Glu  Asp  Asp  Glu  Asp  Asp  Glu  Asp  Asp  Asp  Asp  Gln
 65                      70                       75                       80

Lys  Pro  Lys  Arg  Arg  Gly  Pro  Lys  Lys  Lys  Met  Thr  Lys  Ala  Arg
                    85                       90                       95

Val  Glu  Arg  Phe  Lys  Val  Arg  Arg  Met  Lys  Ala  Asn  Ala  Arg  Glu  Arg
               100                      105                      110

Asn  Arg  Met  His  Gly  Leu  Asn  Asp  Ala  Leu  Asp  Ser  Leu  Arg  Lys  Val
               115                      120                      125

Val  Pro  Cys  Tyr  Ser  Lys  Thr  Gln  Lys  Leu  Ser  Lys  Ile  Glu  Thr  Leu
     130                      135                      140

Arg  Leu  Ala  Lys  Asn  Tyr  Ile  Trp  Ala  Leu  Ser  Glu  Ile  Leu  Arg  Ser
145                      150                      155                      160

Gly  Lys  Ser  Pro  Asp  Leu  Val  Ser  Phe  Val  Gln  Thr  Leu  Cys  Lys  Gly
                    165                      170                      175

Leu  Ser  Gln  Pro  Thr  Thr  Asn  Leu  Val  Ala  Gly  Cys  Leu  Gln  Leu  Asn
               180                      185                      190
```

```
Pro  Arg  Thr  Phe  Leu  Pro  Glu  Gln  Ser  Gln  Asp  Ile  Gln  Ser  His  Met
          195                      200                      205

Gln  Thr  Ala  Ser  Ser  Ser  Phe  Pro  Leu  Gln  Gly  Tyr  Pro  Tyr  Gln  Ser
     210                      215                      220

Pro  Gly  Leu  Pro  Ser  Pro  Pro  Tyr  Gly  Thr  Met  Asp  Ser  Ser  His  Val
225                      230                      235                      240

Phe  His  Val  Lys  Pro  His  Ser  Tyr  Gly  Ala  Ala  Leu  Glu  Pro  Phe  Phe
               245                      250                      255

Asp  Ser  Ser  Thr  Val  Thr  Glu  Cys  Thr  Ser  Pro  Ser  Phe  Asp  Gly  Pro
               260                      265                      270

Leu  Ser  Pro  Pro  Leu  Ser  Val  Asn  Gly  Asn  Phe  Thr  Phe  Lys  His  Glu
          275                      280                      285

His  Ser  Glu  Tyr  Asp  Lys  Asn  Tyr  Thr  Phe  Thr  Met  His  Tyr  Pro  Ala
          290                      295                      300

Ala  Thr  Ile  Ser  Gln  Gly  His  Gly  Pro  Leu  Phe  Ser  Thr  Gly  Gly  Pro
305                           310                      315                      320

Arg  Cys  Glu  Ile  Pro  Ile  Asp  Thr  Ile  Met  Ser  Tyr  Asp  Gly  His  Ser
               325                      330                      335

His  His  Glu  Arg  Val  Met  Ser  Ala  Gln  Leu  Asn  Ala  Ile  Phe  His  Asp
               340                      345                      350
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

```
Asn  Ala  Arg  Glu  Arg  Arg  Arg
1                   5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:6:

```
Asn  Glu  Arg  Glu  Arg  Asn  Arg
1                   5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:7:

```
Asn  Ala  Arg  Glu  Arg
```

( 2 ) INFORMATION FOR SEQ ID NO:8:

( i ) SEQUENCE CHARACTERISTICS:
        ( A ) LENGTH: 524 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 9F1

( i x ) FEATURE:
        ( A ) NAME/KEY: CDS
        ( B ) LOCATION: 57..524

( x i ) SEQUENCE DESCRIPTION: SEQ ID NO:8:

```
TTTTCTGCT  TTCTTTCTG  TTTGCCTCTC  CCTTGTTGAA  TGTAGGAAAT  CGAAAC                    56

ATG ACC AAA TCG TAC AGC GAG AGT GGG CTG ATG GGC GAG CCT CAG CCC                    104
Met Thr Lys Ser Tyr Ser Glu Ser Gly Leu Met Gly Glu Pro Gln Pro
 1               5                  10                  15

CAA GGT CCT CCA AGC TGG ACA GAC GAG TGT CTC AGT TCT CAG GAC GAG                    152
Gln Gly Pro Pro Ser Trp Thr Asp Glu Cys Leu Ser Ser Gln Asp Glu
             20                  25                  30

GAG CAC GAG GCA GAC AAG AAG GAG GAC GAC CTC GAA GCC ATG AAC GCA                    200
Glu His Glu Ala Asp Lys Lys Glu Asp Asp Leu Glu Ala Met Asn Ala
         35                  40                  45

GAG GAG GAC TCA CTG AGG AAC GGG GGA GAG GAG GAG GAC GAA GAT GAG                    248
Glu Glu Asp Ser Leu Arg Asn Gly Gly Glu Glu Glu Asp Glu Asp Glu
     50                  55                  60

GAC CTG GAA GAG GAG GAA GAA GAG GAA GAG GAG GAT GAC GAT CAA AAG                    296
Asp Leu Glu Glu Glu Glu Glu Glu Glu Glu Asp Asp Asp Gln Lys
 65                  70                  75                  80

CCC AAG AGA CGC GGC CCC AAA AAG AAG AAG ATG ACT AAG GCT CGC CTG                    344
Pro Lys Arg Arg Gly Pro Lys Lys Lys Lys Met Thr Lys Ala Arg Leu
                 85                  90                  95

GAG CGT TTT AAA TTG AGA CGC ATG AAG GCT AAC GCC CGG GAG CGG AAC                    392
Glu Arg Phe Lys Leu Arg Arg Met Lys Ala Asn Ala Arg Glu Arg Asn
             100                 105                 110

CGC ATG CAC GGA CTG AAC GCG GCG CTA GAC AAC CTG CGC AAG GTG GTG                    440
Arg Met His Gly Leu Asn Ala Ala Leu Asp Asn Leu Arg Lys Val Val
         115                 120                 125

CCT TGC TAT TCT AAG ACG CAG AAG CTG TCC AAA ATC GAG ACT CTG CGC                    488
Pro Cys Tyr Ser Lys Thr Gln Lys Leu Ser Lys Ile Glu Thr Leu Arg
     130                 135                 140

TTG GCC AAG AAC TAC ATC TGG GCT CTG TCG GAG ATC                                    524
Leu Ala Lys Asn Tyr Ile Trp Ala Leu Ser Glu Ile
145                 150                 155
```

( 2 ) INFORMATION FOR SEQ ID NO:9:

( i ) SEQUENCE CHARACTERISTICS:
        ( A ) LENGTH: 156 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Met Thr Lys Ser Tyr Ser Glu Ser Gly Leu Met Gly Glu Pro Gln Pro

|   | 1 |   |   |   | 5 |   |   |   |   | 10 |   |   |   |   | 15 |
|---|---|---|---|---|---|---|---|---|---|---|---|---|---|---|---|
| Gln | Gly | Pro | Pro | Ser | Trp | Thr | Asp | Glu | Cys | Leu | Ser | Ser | Gln | Asp | Glu |
|   |   |   | 20 |   |   |   |   | 25 |   |   |   |   | 30 |   |   |
| Glu | His | Glu | Ala | Asp | Lys | Lys | Glu | Asp | Leu | Glu | Ala | Met | Asn | Ala |
|   |   | 35 |   |   |   |   | 40 |   |   |   |   | 45 |   |   |
| Glu | Glu | Asp | Ser | Leu | Arg | Asn | Gly | Gly | Glu | Glu | Glu | Asp | Glu | Asp | Glu |
|   | 50 |   |   |   |   | 55 |   |   |   |   | 60 |   |   |   |
| Asp | Leu | Glu | Glu | Glu | Glu | Glu | Glu | Glu | Glu | Asp | Asp | Asp | Gln | Lys |
| 65 |   |   |   |   | 70 |   |   |   |   | 75 |   |   |   |   | 80 |
| Pro | Lys | Arg | Arg | Gly | Pro | Lys | Lys | Lys | Met | Thr | Lys | Ala | Arg | Leu |
|   |   |   |   | 85 |   |   |   |   | 90 |   |   |   |   | 95 |
| Glu | Arg | Phe | Lys | Leu | Arg | Arg | Met | Lys | Ala | Asn | Ala | Arg | Glu | Arg | Asn |
|   |   |   | 100 |   |   |   |   | 105 |   |   |   |   | 110 |   |   |
| Arg | Met | His | Gly | Leu | Asn | Ala | Ala | Leu | Asp | Asn | Leu | Arg | Lys | Val | Val |
|   |   | 115 |   |   |   |   | 120 |   |   |   |   | 125 |   |   |
| Pro | Cys | Tyr | Ser | Lys | Thr | Gln | Lys | Leu | Ser | Lys | Ile | Glu | Thr | Leu | Arg |
|   | 130 |   |   |   |   | 135 |   |   |   |   | 140 |   |   |   |
| Leu | Ala | Lys | Asn | Tyr | Ile | Trp | Ala | Leu | Ser | Glu | Ile |
| 145 |   |   |   |   | 150 |   |   |   |   | 155 |   |

( 2 ) INFORMATION FOR SEQ ID NO:10:

( i ) SEQUENCE CHARACTERISTICS:
        ( A ) LENGTH: 1535 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 14B1 (neuroD2)

( i x ) FEATURE:
        ( A ) NAME/KEY: CDS
        ( B ) LOCATION: 55..1194

( x i ) SEQUENCE DESCRIPTION: SEQ ID NO:10:

```
CCCCTCACTT TGTGCTGTCT GTCTCCCCTT CCCGCCCGGG GNCCCTCAGG CACCATGCTG      60
ACCCGCCTGT TCAGCGAGCC CGGCCTTCTC TCGGACGTGC CCAAGTTCGC CAGCTGGGGC     120
GACGGCGAAG ACGACGAGCC GAGGAGCGAC AAGGGCGACG CGCCGCCACC GCCACCGCCT     180
GCGCCCGGGC CAGGGGCTCC GGGGCCAGCC CGGGCGGCCA AGCCAGTCCC TCTCCGTGGA     240
GAAGAGGGGA CGGAGGCCAC GTTGGCCGAG GTCAAGGAGG AAGGCGAGCT GGGGGGAGAG     300
GAGGAGGAGG AAGAGGAGGA GGAAGAAGGA CTGGACGAGG CGGAGGGCGA GCGGCCCAAG     360
AAGCGCGGGC CCAAGAAGCG CAAGATGACC AAGGCGCGCT TGGAGCGCTC CAAGCTTCGG     420
CGGCAGAAGG CGAACGCGCG GGAGCGCAAC CGCATGCACG ACCTGAACGC AGCCCTGGAC     480
AACCTGCGCA AGGTGGTGCC CTGCTACTCC AAGACGCAGA AGCTGTCCAA GATCGAGACG     540
CTGCGCCTAG CCAAGAACTA TATCTGGGCG CTCTCGGAGA TCCTGCGCTC CGGCAAGCGG     600
CCAGACCTAG TGTCCTACGT GCAGACTCTG TGCAAGGGTC TGTCGCAGCC CACCACCAAT     660
CTGGTGGCCG GCTGTCTGCA GCTCAACTCT CGCAACTTCC TCACGGAGCA AGGCGCCGAC     720
GGTGCCGGCC GCTTCCACGG CTCGGGCGGC CCGTTCGCCA TGCACCCCTA CCCGTACCCG     780
TGCTCGCGCC TGGCGGGCGC ACAGTGCCAG GCGGCCGGCG GCCTGGGCGG CGGCGCGGCG     840
```

-continued

| | | | | | |
|---|---|---|---|---|---|
| CACGCCCTGC | GGACCCACGG | CTACTGCGCC | GCCTACGAGA | CGCTGTATGC | GGCGGCAGGC | 900 |
| GGTGGCGGCG | CGAGCCCGGA | CTACAACAGC | TCCGAGTACG | AGGGCCCGCT | CAGCCCCCCG | 960 |
| CTCTGTCTCA | ATGGCAACTT | CTCACTCAAG | CAGGACTCCT | CGCCCGACCA | CGAGAAAAGC | 1020 |
| TACCACTACT | CTATGCACTA | CTCGGCGCTG | CCCGGTTCGC | GCCACGGCCA | CGGGCTAGTC | 1080 |
| TTCGGCTCGT | CGGCTGTGCG | CGGGGGCGTC | CACTCGGAGA | ATCTCTTGTC | TTACGATATG | 1140 |
| CACCTTCACC | ACGACCGGGG | CCCCATGTAC | GAGGAGCTCA | ATGCGTTTTT | TCATAACTGA | 1200 |
| GACTTCGCGC | CGNCTCCCTN | CTTTTTCTTT | TGCCTTTGCC | CGCCCCCTG | TCCCCAGCCC | 1260 |
| CCAGAGCGCA | GGGACACCCC | CATNCTACCC | CGGCNCCGGC | GGAGCGGGCC | ACCGGTCTGC | 1320 |
| CGCTCTCCTG | GGGCAGCGCA | GTCTGTTACN | TGTGGGTGGC | TGTCCCAGGG | GCCTCGCTTC | 1380 |
| CCCCAGGGAC | TCGCCTTCTC | TCTCCAAGGG | GTTCCCTCCT | CCTCTCTCCC | AAGGAGTGCT | 1440 |
| TCTCCAGGGA | CCTCTCTCCG | GGGGCTCCCT | GGAGGCACCC | CTCCCCCATT | CCCAATATCT | 1500 |
| TCGCTGAGGT | TTCCTCCTCC | CCCTCCTCCC | TGCAG | | | 1535 |

( 2 ) INFORMATION FOR SEQ ID NO:11:

( i ) SEQUENCE CHARACTERISTICS:
        ( A ) LENGTH: 381mino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:11:

```
Met Leu Thr Arg Leu Phe Ser Glu Pro Gly Leu Leu Ser Asp Val Pro
 1               5                  10                  15

Lys Phe Ala Ser Trp Gly Asp Gly Glu Asp Asp Glu Pro Arg Ser Asp
                20                  25                  30

Lys Gly Asp Ala Pro Pro Pro Pro Pro Ala Pro Gly Pro Gly Ala
                35                  40                  45

Pro Gly Pro Ala Arg Ala Ala Lys Pro Val Pro Leu Arg Gly Glu Glu
    50                  55                  60

Gly Thr Glu Ala Thr Leu Ala Glu Val Lys Glu Glu Gly Glu Leu Gly
65                  70                  75                  80

Gly Glu Glu Glu Glu Glu Glu Glu Glu Glu Gly Leu Asp Glu Ala
                85                  90                  95

Glu Gly Glu Arg Pro Lys Lys Arg Gly Pro Lys Lys Arg Lys Met Thr
                100                 105                 110

Lys Ala Arg Leu Glu Arg Ser Lys Leu Arg Arg Gln Lys Ala Asn Ala
        115                 120                 125

Arg Glu Arg Asn Arg Met His Asp Leu Asn Ala Ala Leu Asp Asn Leu
    130                 135                 140

Arg Lys Val Val Pro Cys Tyr Ser Lys Thr Gln Lys Leu Ser Lys Ile
145                 150                 155                 160

Glu Thr Leu Arg Leu Ala Lys Asn Tyr Ile Trp Ala Leu Ser Glu Ile
                165                 170                 175

Leu Arg Ser Gly Lys Arg Pro Asp Leu Val Ser Tyr Val Gln Thr Leu
            180                 185                 190

Cys Lys Gly Leu Ser Gln Pro Thr Thr Asn Leu Val Ala Gly Cys Leu
        195                 200                 205

Gln Leu Asn Ser Arg Asn Phe Leu Thr Glu Gln Gly Ala Asp Gly Ala
    210                 215                 220
```

|     |     |     |     |     |     |     |     |     |     |     |     |     |     |     |     |
|-----|-----|-----|-----|-----|-----|-----|-----|-----|-----|-----|-----|-----|-----|-----|-----|
| Gly | Arg | Phe | His | Gly | Ser | Gly | Gly | Pro | Phe | Ala | Met | His | Pro | Tyr | Pro |
| 225 |     |     |     | 230 |     |     |     | 235 |     |     |     |     |     | 240 |     |
| Tyr | Pro | Cys | Ser | Arg | Leu | Ala | Gly | Ala | Gln | Cys | Gln | Ala | Ala | Gly | Gly |
|     |     |     |     | 245 |     |     |     | 250 |     |     |     |     |     | 255 |     |
| Leu | Gly | Gly | Gly | Ala | Ala | His | Ala | Leu | Arg | Thr | His | Gly | Tyr | Cys | Ala |
|     |     |     | 260 |     |     |     |     | 265 |     |     |     |     | 270 |     |     |
| Ala | Tyr | Glu | Thr | Leu | Tyr | Ala | Ala | Ala | Gly | Gly | Gly | Gly | Ala | Ser | Pro |
|     |     | 275 |     |     |     |     | 280 |     |     |     |     | 285 |     |     |     |
| Asp | Tyr | Asn | Ser | Ser | Glu | Tyr | Glu | Gly | Pro | Leu | Ser | Pro | Pro | Leu | Cys |
|     | 290 |     |     |     |     | 295 |     |     |     |     | 300 |     |     |     |     |
| Leu | Asn | Gly | Asn | Phe | Ser | Leu | Lys | Gln | Asp | Ser | Ser | Pro | Asp | His | Glu |
| 305 |     |     |     |     | 310 |     |     |     |     | 315 |     |     |     |     | 320 |
| Lys | Ser | Tyr | His | Tyr | Ser | Met | His | Tyr | Ser | Ala | Leu | Pro | Gly | Ser | Arg |
|     |     |     |     | 325 |     |     |     |     | 330 |     |     |     |     | 335 |     |
| His | Gly | His | Gly | Leu | Val | Phe | Gly | Ser | Ser | Ala | Val | Arg | Gly | Gly | Val |
|     |     |     | 340 |     |     |     |     | 345 |     |     |     |     | 350 |     |     |
| His | Ser | Glu | Asn | Leu | Leu | Ser | Tyr | Asp | Met | His | Leu | His | His | Asp | Arg |
|     |     | 355 |     |     |     |     | 360 |     |     |     |     | 365 |     |     |     |
| Gly | Pro | Met | Tyr | Glu | Glu | Leu | Asn | Ala | Phe | Phe | His | Asn |     |     |     |
| 370 |     |     |     |     | 375 |     |     |     |     | 380 |     |     |     |     |     |

( 2 ) INFORMATION FOR SEQ ID NO:12:

( i ) SEQUENCE CHARACTERISTICS:
        ( A ) LENGTH: 1268 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens ( v i i ) IMMEDIATE SOURCE:
        ( B ) CLONE: 20A1 (neuroD3)

( i x ) FEATURE:
        ( A ) NAME/KEY: CDS
        ( B ) LOCATION: 55..768

( x i ) SEQUENCE DESCRIPTION: SEQ ID NO:12:

| CTGCAGCGCT | CTGAGCCGCT | TTCTATCTGT | CCGTCGGTCC | TGCACAGCGC | AACG ATG<br>Met<br>1 | 57 |
|---|---|---|---|---|---|---|

|     |     |     |     |     |     |     |     |     |     |     |     |     |     |     |     |
|-----|-----|-----|-----|-----|-----|-----|-----|-----|-----|-----|-----|-----|-----|-----|-----|
| CCA | GCC | CGC | CTT | GAG | ACC | TGC | ATC | TCC | GAC | CTC | GAC | TGC | GCC | AGC | AGC | 105
| Pro | Ala | Arg | Leu | Glu | Thr | Cys | Ile | Ser | Asp | Leu | Asp | Cys | Ala | Ser | Ser |
|     |     |     |     | 5   |     |     |     |     | 10  |     |     |     |     | 15  |     |
| AGC | GGC | AGT | GAC | CTA | TCC | GGC | TTC | CTC | ACC | GAC | GAG | GAA | GAC | TGT | GCC | 153
| Ser | Gly | Ser | Asp | Leu | Ser | Gly | Phe | Leu | Thr | Asp | Glu | Glu | Asp | Cys | Ala |
|     |     | 20  |     |     |     |     | 25  |     |     |     |     | 30  |     |     |     |
| AGA | CTC | CAA | CAG | GCA | GCC | TCC | GCT | TCG | GGG | CCG | CCC | GCG | CCG | GCC | CGC | 201
| Arg | Leu | Gln | Gln | Ala | Ala | Ser | Ala | Ser | Gly | Pro | Pro | Ala | Pro | Ala | Arg |
|     |     | 35  |     |     |     |     | 40  |     |     |     |     | 45  |     |     |     |
| AGG | GGC | GCG | CCC | AAT | ATC | TCC | CGG | GCG | TCT | GAG | GTT | CCA | GGG | GCA | CAG | 249
| Arg | Gly | Ala | Pro | Asn | Ile | Ser | Arg | Ala | Ser | Glu | Val | Pro | Gly | Ala | Gln |
| 50  |     |     |     |     | 55  |     |     |     |     | 60  |     |     |     |     | 65  |
| GAC | GAC | GAG | CAG | GAG | AGG | CGG | CGG | CGC | CGC | GGC | CGG | ACG | CGG | GTC | CGC | 297
| Asp | Asp | Glu | Gln | Glu | Arg | Arg | Arg | Arg | Arg | Gly | Arg | Thr | Arg | Val | Arg |
|     |     |     |     | 70  |     |     |     |     | 75  |     |     |     |     | 80  |     |
| TCC | GAG | GCG | CTG | CTG | CAC | TCG | CTG | CGC | AGG | AGC | CGG | CGC | GTC | AAG | GCC | 345
| Ser | Glu | Ala | Leu | Leu | His | Ser | Leu | Arg | Arg | Ser | Arg | Arg | Val | Lys | Ala |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     |     | 85  |     |     |     |     | 90  |     |     |     |     | 95  |     |     |
| AAC | GAT | CGC | GAG | CGC | AAC | CGC | ATG | CAC | AAC | TTG | AAC | GCG | GCC | CTG | GAC | 393 |
| Asn | Asp | Arg | Glu | Arg | Asn | Arg | Met | His | Asn | Leu | Asn | Ala | Ala | Leu | Asp |     |
|     |     | 100 |     |     |     |     | 105 |     |     |     |     | 110 |     |     |     |     |
| GCA | CTG | CGC | AGC | GTG | CTG | CCC | TCG | TTC | CCC | GAC | GAC | ACC | AAG | CTC | ACC | 441 |
| Ala | Leu | Arg | Ser | Val | Leu | Pro | Ser | Phe | Pro | Asp | Asp | Thr | Lys | Leu | Thr |     |
|     | 115 |     |     |     |     | 120 |     |     |     |     | 125 |     |     |     |     |     |
| AAA | ATC | GAG | ACG | CTG | CGC | TTC | GCC | TAC | AAC | TAC | ATC | TGG | GCT | CTG | GCC | 489 |
| Lys | Ile | Glu | Thr | Leu | Arg | Phe | Ala | Tyr | Asn | Tyr | Ile | Trp | Ala | Leu | Ala |     |
| 130 |     |     |     |     | 135 |     |     |     |     | 140 |     |     |     |     | 145 |     |
| GAG | ACA | CTG | CGC | CTG | GCG | GAT | CAA | GGG | CTG | CCC | GGA | GGC | GGT | GCC | CGG | 537 |
| Glu | Thr | Leu | Arg | Leu | Ala | Asp | Gln | Gly | Leu | Pro | Gly | Gly | Gly | Ala | Arg |     |
|     |     |     |     | 150 |     |     |     |     | 155 |     |     |     |     | 160 |     |     |
| GAG | CGC | CTC | CTG | CCG | CCG | CAG | TGC | GTC | CCC | TGC | CTG | CCC | GGT | CCC | CCA | 585 |
| Glu | Arg | Leu | Leu | Pro | Pro | Gln | Cys | Val | Pro | Cys | Leu | Pro | Gly | Pro | Pro |     |
|     |     |     | 165 |     |     |     |     | 170 |     |     |     |     | 175 |     |     |     |
| AGC | CCC | GCC | AGC | GAC | GCG | GAG | TCC | TGG | GGC | TCA | GGT | GCC | GCC | GCC | GCC | 633 |
| Ser | Pro | Ala | Ser | Asp | Ala | Glu | Ser | Trp | Gly | Ser | Gly | Ala | Ala | Ala | Ala |     |
|     |     | 180 |     |     |     |     | 185 |     |     |     |     | 190 |     |     |     |     |
| TCC | CCG | CTC | TCT | GAC | CCC | AGT | AGC | CCA | GCC | GCC | TCC | GAA | GAC | TTC | ACC | 681 |
| Ser | Pro | Leu | Ser | Asp | Pro | Ser | Ser | Pro | Ala | Ala | Ser | Glu | Asp | Phe | Thr |     |
|     | 195 |     |     |     |     | 200 |     |     |     |     | 205 |     |     |     |     |     |
| TAC | CGC | CCC | GGC | GAC | CCT | GTT | TTC | TCC | TTC | CCA | AGC | CTG | CCC | AAA | GAC | 729 |
| Tyr | Arg | Pro | Gly | Asp | Pro | Val | Phe | Ser | Phe | Pro | Ser | Leu | Pro | Lys | Asp |     |
| 210 |     |     |     |     | 215 |     |     |     |     | 220 |     |     |     |     | 225 |     |
| TTG | CTC | CAC | ACA | ACG | CCC | TGT | TTC | ATT | CCT | TAC | CAC | TAGGCCCTTT |  |  |  | 775 |
| Leu | Leu | His | Thr | Thr | Pro | Cys | Phe | Ile | Pro | Tyr | His |     |     |     |     |     |
|     |     |     | 230 |     |     |     |     |     | 235 |     |     |     |     |     |     |     |

| | | | | | |
|---|---|---|---|---|---|
| GTAGACACTG | TTACTTTCCC | CCTCCCCTAG | TCAGCAGGCA | ATAGATTGGG | CCCAGCTGCC | 835 |
| GCCTCGGGAC | CCCTCTCCAG | GCGGAGGGAG | GAAGCGGGAG | CTTTAAAGCA | GTCGGGGATA | 895 |
| CCTGAGCCGC | TTGTTAGGTC | GCCGCACCCT | CGCGGCGGAT | GTCTCTTGGT | CTGTTTCTCC | 955 |
| GGCCCTCAGC | CCAGCGCCCC | TCCTGCCCGC | CCCTAGACGG | CCTTTCCTTT | TGCACTTTCT | 1015 |
| GAACTCCACA | AAACCTCCTT | TGTGACTGGC | TCAGAACTGA | CCCCAGCCAC | CACTTCAGTG | 1075 |
| TGATTTAGAA | AAGGGACAGA | TCAGCCCCTG | AAGACGAGGT | GAAAAGTCAA | TTTTACAATT | 1135 |
| TGTAGAACTC | TAATGAAGAA | AAACGAGCAT | GAAAATTCGG | TTTGAGCCGG | CTGACAATAC | 1195 |
| AATGAAAAGG | CTTAAAAAGC | AGAGACAAGG | AGTGGGCTTC | ATGCATTATG | GATCCCGACC | 1255 |
| CCCACCACTG | CAG | | | | | 1268 |

( 2 ) INFORMATION FOR SEQ ID NO:13:

( i ) SEQUENCE CHARACTERISTICS:
        ( A ) LENGTH: 237 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Met | Pro | Ala | Arg | Leu | Glu | Thr | Cys | Ile | Ser | Asp | Leu | Asp | Cys | Ala | Ser |
| 1 | | | | 5 | | | | | 10 | | | | | 15 | |
| Ser | Ser | Gly | Ser | Asp | Leu | Ser | Gly | Phe | Leu | Thr | Asp | Glu | Glu | Asp | Cys |
| | | | 20 | | | | | 25 | | | | | 30 | | |
| Ala | Arg | Leu | Gln | Gln | Ala | Ala | Ser | Ala | Ser | Gly | Pro | Pro | Ala | Pro | Ala |
| | | 35 | | | | | 40 | | | | | 45 | | | |
| Arg | Arg | Gly | Ala | Pro | Asn | Ile | Ser | Arg | Ala | Ser | Glu | Val | Pro | Gly | Ala |
| 50 | | | | | 55 | | | | | 60 | | | | | |

-continued

| | | | | | | | | | | | | | | |
|---|---|---|---|---|---|---|---|---|---|---|---|---|---|---|
| Gln 65 | Asp | Asp | Glu | Gln | Glu 70 | Arg | Arg | Arg | Arg 75 | Arg | Gly | Arg | Thr | Arg Val 80 |
| Arg | Ser | Glu | Ala | Leu 85 | Leu | His | Ser | Leu | Arg 90 | Ser | Arg | Arg | Val 95 | Lys |
| Ala | Asn | Asp | Arg 100 | Glu | Arg | Asn | Arg | Met 105 | His | Asn | Leu | Asn 110 | Ala | Ala Leu |
| Asp | Ala | Leu 115 | Arg | Ser | Val | Leu | Pro 120 | Ser | Phe | Pro | Asp 125 | Thr | Lys | Leu |
| Thr | Lys 130 | Ile | Glu | Thr | Leu | Arg 135 | Phe | Ala | Tyr | Asn | Tyr 140 | Ile | Trp | Ala Leu |
| Ala 145 | Glu | Thr | Leu | Arg | Leu 150 | Ala | Asp | Gln | Gly | Leu 155 | Pro | Gly | Gly | Gly Ala 160 |
| Arg | Glu | Arg | Leu | Leu 165 | Pro | Pro | Gln | Cys | Val 170 | Pro | Cys | Leu | Pro 175 | Gly Pro |
| Pro | Ser | Pro | Ala 180 | Ser | Asp | Ala | Glu | Ser 185 | Trp | Gly | Ser | Gly 190 | Ala | Ala Ala |
| Ala | Ser | Pro 195 | Leu | Ser | Asp | Pro | Ser 200 | Ser | Pro | Ala | Ala 205 | Ser | Glu | Asp Phe |
| Thr | Tyr 210 | Arg | Pro | Gly | Asp | Pro 215 | Val | Phe | Ser | Phe | Pro 220 | Ser | Leu | Pro Lys |
| Asp 225 | Leu | Leu | His | Thr | Thr 230 | Pro | Cys | Phe | Ile | Pro 235 | Tyr | His | | |

( 2 ) INFORMATION FOR SEQ ID NO:14:

( i ) SEQUENCE CHARACTERISTICS:
        ( A ) LENGTH: 1560 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: HC2A ( i x ) FEATURE:
        ( A ) NAME/KEY: CDS
        ( B ) LOCATION: 57..1126

( x i ) SEQUENCE DESCRIPTION: SEQ ID NO:14:

| | | | | | | |
|---|---|---|---|---|---|---|
| TTTTTCTGCT | TTTCTTTCTG | TTTGCCTCTC | CCTTGTTGAA | TGTAGGAAAT | CGAAACATGA | 60 |
| CCAAATCGTA | CAGCGAGAGT | GGGCTGATGG | GCGAGCCTCA | GCCCCAAGGT | CCTCCAAGCT | 120 |
| GGACAGACGA | GTGTCTCAGT | TCTCAGGACG | AGGAGCACGA | GGCAGACAAG | AAGGAGGACG | 180 |
| ACCTCGAAGC | CATGAACGCA | GAGGAGGACT | CACTGAGGAA | CGGGGGAGAG | GAGGAGGACG | 240 |
| AAGATGAGGA | CCTGGAAGAG | GAGGAAGAAG | AGGAAGAGGA | GGATGACGAT | CAAAAGCCCA | 300 |
| AGAGACGCGG | CCCCAAAAAG | AAGAAGATGA | CTAAGGCTCG | CCTGGAGCGT | TTTAAATTGA | 360 |
| GACGCATGAA | GGCTAACGCC | CGGGAGCGGA | ACCGCATGCA | CGGACTGAAC | GCGGCGCTAG | 420 |
| ACAACCTGCG | CAAGGTGGTG | CCTTGCTATT | CTAAGACGCA | GAAGCTGTCC | AAAATCGAGA | 480 |
| CTCTGCGCTT | GGCCAAGAAC | TACATCTGGG | CTCTGTCGGA | GATCCTGCGC | TCAGGCAAAA | 540 |
| GCCCAGACCT | GGTCTCCTTC | GTTCAGACGC | TTTGCAAGGG | CTTATCCCAA | CCCACCACCA | 600 |
| ACCTGGTTGC | GGGCTGCCTG | CAACTCAATC | CTCGGACTTT | CTGCCTGAG | CAGAACCAGG | 660 |
| ACATGCCCCC | GCACCTGCCG | ACGGCCAGCG | CTTCCTTCCC | TGTACACCCC | TACTCCTACC | 720 |

```
AGTCGCCTGG GCTGCCCAGT CCGNCTTACG GTACCATGGA CAGCTCCCAT GTCTTCCACG    780
TTAAGCCTCC GCCGCACGCC TACAGCGCAG CGCTGGAGCC CTTCTTTGAA AGCCCTCTGA    840
CTGATTGCAC CAGCCCTTCC TTTGATGGAC CCCTCAGCCC GCCGCTCAGC ATCAATGGCA    900
ACTTCTCTTT CAAACACGAA CCGTCCGCCG AGTTTGAGAA AAATTATGCC TTTACCATGC    960
ACTATCCTGC AGCGACACTG GCAGGGGCCC AAAGCCACGG ATCAATCTTC TCAGGCACCG   1020
CTGCCCCTCG CTGCGAGATC CCCATAGACA ATATTATGTC CTTCGATAGC CATTCACATC   1080
ATGAGCGAGT CATGAGTGCC CAGCTCAATG CCATATTTCA TGATTAGAGG CACGCCAGTT   1140
TCACCATTTC CGGGAAACGA ACCCACTGTG CTTACAGTGA CTGTCGTGTT TACAAAAGGC   1200
AGCCCTTTGG TACTACTGCT GCAAAGTGCA AATACTCCAA GCTTCAAGTG ATATATGTAT   1260
TTATTGTCAT TACTGCCTTT GGAAGAAACA GGGGATCAAA GTTCCTGTTC ACCTTATGTA   1320
TTATTTTCTA TAGACTCTTC TATTTTAAAA AATAAAAAAA TACAGTAAAG TTTAAAAAAT   1380
ACACCACGAA TTTGGTGTGG CTGTATTCAG ATCGTATTAA TTATCTGATC GGGATAACAA   1440
AATCACAAGC AATAATTAGG ATCTATGCAA TTTTTAAACT AGTAATGGGC CAATTAAAAT   1500
ATATATAAAT ATATATTTCA ACCAGCATTT TACTACTTGT TACCTCCCAT GCTGAATTAT   1560
```

( 2 ) INFORMATION FOR SEQ ID NO:15:

( i ) SEQUENCE CHARACTERISTICS:
        ( A ) LENGTH: 356 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:15:

```
Met Thr Lys Ser Tyr Ser Glu Ser Gly Leu Met Gly Glu Pro Gln Pro
  1               5                  10                  15

Gln Gly Pro Pro Ser Trp Thr Asp Glu Cys Leu Ser Ser Gln Asp Glu
                 20                  25                  30

Glu His Glu Ala Asp Lys Lys Glu Asp Leu Glu Ala Met Asn Ala
             35                  40                  45

Glu Glu Asp Ser Leu Arg Asn Gly Gly Glu Glu Asp Glu Asp Glu
 50                  55                  60

Asp Leu Glu Glu Glu Glu Glu Glu Glu Asp Asp Asp Gln Lys
 65                  70                  75              80

Pro Lys Arg Arg Gly Pro Lys Lys Lys Met Thr Lys Ala Arg Leu
                 85                  90                  95

Glu Arg Phe Lys Leu Arg Arg Met Lys Ala Asn Ala Arg Glu Arg Asn
                100                 105                 110

Arg Met His Gly Leu Asn Ala Ala Leu Asp Asn Leu Arg Lys Val Val
             115                 120                 125

Pro Cys Tyr Ser Lys Thr Gln Lys Leu Ser Lys Ile Glu Thr Leu Arg
         130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
             180                 185                 190

Arg Thr Phe Leu Pro Glu Gln Asn Gln Asp Met Pro Pro His Leu Pro
```

|   |   | 195 |   |   |   |   | 200 |   |   |   |   | 205 |   |   |
|---|---|---|---|---|---|---|---|---|---|---|---|---|---|---|
| Thr | Ala 210 | Ser | Ala | Ser | Phe | Pro 215 | Val | His | Pro | Tyr | Ser 220 | Tyr | Gln | Ser | Pro |
| Gly 225 | Leu | Pro | Ser | Pro | Xaa 230 | Tyr | Gly | Thr | Met | Asp 235 | Ser | Ser | His | Val | Phe 240 |
| His | Val | Lys | Pro | Pro 245 | Pro | His | Ala | Tyr | Ser 250 | Ala | Ala | Leu | Glu | Pro 255 | Phe |
| Phe | Glu | Ser | Pro 260 | Leu | Thr | Asp | Cys | Thr 265 | Ser | Pro | Ser | Phe | Asp 270 | Gly | Pro |
| Leu | Ser | Pro 275 | Pro | Leu | Ser | Ile | Asn 280 | Gly | Asn | Phe | Ser | Phe 285 | Lys | His | Glu |
| Pro | Ser 290 | Ala | Glu | Phe | Glu | Lys 295 | Asn | Tyr | Ala | Phe | Thr 300 | Met | His | Tyr | Pro |
| Ala 305 | Ala | Thr | Leu | Ala | Gly 310 | Ala | Gln | Ser | His | Gly 315 | Ser | Ile | Phe | Ser | Gly 320 |
| Thr | Ala | Ala | Pro | Arg 325 | Cys | Glu | Ile | Pro | Ile 330 | Asp | Asn | Ile | Met | Ser 335 | Phe |
| Asp | Ser | His | Ser 340 | His | His | Glu | Arg | Val 345 | Met | Ser | Ala | Gln | Leu 350 | Asn | Ala |
| Ile | Phe | His 355 | Asp |   |   |   |   |   |   |   |   |   |   |   |   |

( 2 ) INFORMATION FOR SEQ ID NO:16:

( i ) SEQUENCE CHARACTERISTICS:
        ( A ) LENGTH: 1951 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mus musculus ( v i i ) IMMEDIATE SOURCE:
        ( B ) CLONE: 1.1.1 (mouse neuroD2)

( i x ) FEATURE:
        ( A ) NAME/KEY: CDS
        ( B ) LOCATION: 230..1378

( x i ) SEQUENCE DESCRIPTION: SEQ ID NO:16:

```
GAATTCAAGC TAGAGGCTGG TACCCCGCCT GGTAGAGATG CCACACTCGC TCCGCGGCTC      60

GCATGGCGCT CTGAAGACGC CGGCGCCCGC GCCTTGAGGA ACCGCTGCCC CCGCTCCCTG     120

AAGATGGGGG AACAATGAAA TAAGCGAGAA GATTCCTCTT CTCCCCCCTC TCTCTCTTGC     180

CCCCTCCCCC CTCCCCTCCC CTCTCCCCTT GACTCCTCTC TGAGGCACCA TGCTGACCCG     240

CCTGTTCAGC GAGCCCGGCC TCCTCTCGGA CGTGCCCAAG TTCGCCAGCT GGGGCGACGG     300

CGACGACGAC GAGCCGAGGA GCGACAAGGG CGACGCGCCG CCGCAGCCTT CTCCTGCTCC     360

CGGGTCGGGG GCTCCAGGAC CCGCCCGGGC CGCCAAGCCA GTGTCTCTTC GTGGAGGAGA     420

AGAGATCCCT GAACCCACGT TGGCTGAGGT CAAGGAGGAA GGAGAGCTGG GCGGCGAGGA     480

GGAGGAGGAA GAGGAGGAGG AGGAAGGACT GGACGAGGCG AAGGCGAGC GGCCCAAGAA     540

GCGCGGGCCG AAGAAACGCA AGATGACCAA GGCGCGTCTG GAGCGCTCCA AGCTGCGGCG     600

ACAGAAGGCC AATGCGCGCG AGCGCAACCG CATGCACGAC CTGAACGCGG CTCTGGACAA     660

CCTGCGCAAG GTGGTCCCCT GCTACTCCAA GACCCAGAAG CTGTCCAAGA TCGAGACCCT     720

GCGCCTGGCC AAGAACTACA TCTGGGCTCT CTCGGAGATC TTGCGCTCCG GGAAGCGGCC     780
```

-continued

```
GGATCTGGTG TCCTACGTGC AGACTCTGTG CAAGGGGCTG TCACAGCCCA CCACGAATCT      840
GGTGGCCGGC TGCCTGCAGT TAAACTCTCG TAACTTCCTC ACGGAGCAGG GCGCGGACGG      900
CGCCGGCCGC TTTCACGGCT CGGGTGGCCC GTTCGCCATG CATCCGTACC CATACCCGTG      960
CTCCCGCCTG GCAGGCGCAC AGTGTCAGGC GGCTGGCGGC CTGGGCGGAG GCGCGGCGCA     1020
CGCCCTGCGG ACCCACGGCT ACTGCGCCGC CTACGAGACG CTGTACGCGG CGGCCGGTGG     1080
CGGCGGCGCT AGCCCGGACT ACAACAGCTC CGAGTACGAG GGTCCACTCA GTCCCCCGCT     1140
CTGTCTCAAC GGCAACTTCT CGCTCAAGCA GGACTCGTCC CCCGATCACG AGAAGAGCTA     1200
CCACTACTCT ATGCACTACT CGGCGCTGCC CGGCTCACGC CACGGCCACG GCTGGTCTT     1260
CGGCTCGTCG GCCGTGCGCG GGGGCGTCCA CTCCGAGAAT CTCTTGTCTT ACGATATGCA     1320
CCTTCACCAC GATCGGGGCC CCATGTACGA GGAGCTCAAC GCATTTTCC ATAACTGAGA     1380
CCTCNCGCCG ACCCCTTCTT TTTCTTTGCC TTTGTCCGGC CCCTTAGCCC CAGCCCCANN     1440
AGCTCAGGGA GCTCCCACCG ACTCCAGAGC CGGGCNCTCG NCNCGCCGCC GGTTCTGCAG     1500
CTCTCCAGAG CGGCGTGCTC TCTTACCTGT GGGTGGCCCG TCCCAGGGGC CTCGCTTGCC     1560
TCTGGGGACT CGCCTTCTCT CTCTCCCCAG CGGCTTCCTC CTCCTTCTC TCGTGGAGAG     1620
CATCTCTNNN GATCTCCCGC CAGCCCTCCC AAGAGACTTC CTCCACATTC CCAAACTTGG     1680
GTTTTCTCTC CCCACCTCCA ACAGGCCAGA GGAGTTGGTA AGGGGTGCTG AGTCTCGGGA     1740
TAGTGTCTCC CCACTTATAG TTACTTAAAC AAACAAACAG ACACAGAGCT TCCAGCNAAA     1800
AGAGTTGGTA TCTCTTCCTT CTCGAAGANC ACCAGCCAGG AGCCCAACCG CCTTCACCCT     1860
AACACNGAAT CTCCNNGTTT TTTATTTTTT ATTTGGTGG GAGGGGATGT GGATTGAGAG     1920
GAAAGAGAGA GCCAAGCCAA TTTGTAACTA G                                    1951
```

( 2 ) INFORMATION FOR SEQ ID NO:17:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Mus musculus ( v i i ) IMMEDIATE SOURCE:
        ( B ) CLONE: 1.1.1 (murine neuroD2)

( x i ) SEQUENCE DESCRIPTION: SEQ ID NO:17:

```
Met Leu Thr Arg Leu Phe Ser Glu Pro Gly Leu Leu Ser Asp Val Pro
 1               5                  10                  15
Lys Phe Ala Ser Trp Gly Asp Gly Asp Asp Glu Pro Arg Ser Asp
             20                  25                  30
Lys Gly Asp Ala Pro Pro Gln Pro Ser Pro Ala Pro Gly Ser Gly Ala
             35                  40                  45
Pro Gly Pro Ala Arg Ala Ala Lys Pro Val Ser Leu Arg Gly Gly Glu
     50                  55                  60
Glu Ile Pro Glu Pro Thr Leu Ala Glu Val Lys Glu Glu Gly Glu Leu
 65                  70                  75                  80
Gly Gly Glu Glu Glu Glu Glu Glu Glu Glu Glu Gly Leu Asp Glu
                 85                  90                  95
Ala Glu Gly Glu Arg Pro Lys Lys Arg Gly Pro Lys Lys Arg Lys Met
                100                 105                 110
```

|     |     |     |     |     |     |     |     |     |     |     |     |     |     |     |
|---|---|---|---|---|---|---|---|---|---|---|---|---|---|---|
| Thr | Lys | Ala<br>115 | Arg | Leu | Glu | Arg | Ser<br>120 | Lys | Leu | Arg | Arg | Gln<br>125 | Lys | Ala | Asn |
| Ala | Arg<br>130 | Glu | Arg | Asn | Arg | Met<br>135 | His | Asp | Leu | Asn | Ala<br>140 | Ala | Leu | Asp | Asn |
| Leu<br>145 | Arg | Lys | Val | Val<br>150 | Pro | Cys | Tyr | Ser | Lys<br>155 | Thr | Gln | Lys | Leu | Ser | Lys<br>160 |
| Ile | Glu | Thr | Leu | Arg<br>165 | Leu | Ala | Lys | Asn | Tyr<br>170 | Ile | Trp | Ala | Leu | Ser<br>175 | Glu |
| Ile | Leu | Arg | Ser<br>180 | Gly | Lys | Arg | Pro | Asp<br>185 | Leu | Val | Ser | Tyr | Val<br>190 | Gln | Thr |
| Leu | Cys | Lys<br>195 | Gly | Leu | Ser | Gln | Pro<br>200 | Thr | Thr | Asn | Leu | Val<br>205 | Ala | Gly | Cys |
| Leu | Gln<br>210 | Leu | Asn | Ser | Arg | Asn<br>215 | Phe | Leu | Thr | Glu | Gln<br>220 | Gly | Ala | Asp | Gly |
| Ala<br>225 | Gly | Arg | Phe | His | Gly<br>230 | Ser | Gly | Gly | Pro | Phe<br>235 | Ala | Met | His | Pro | Tyr<br>240 |
| Pro | Tyr | Pro | Cys | Ser<br>245 | Arg | Leu | Ala | Gly | Ala<br>250 | Gln | Cys | Gln | Ala | Ala<br>255 | Gly |
| Gly | Leu | Gly | Gly<br>260 | Gly | Ala | Ala | His | Ala<br>265 | Leu | Arg | Thr | His | Gly<br>270 | Tyr | Cys |
| Ala | Ala | Tyr<br>275 | Glu | Thr | Leu | Tyr | Ala<br>280 | Ala | Ala | Gly | Gly | Gly<br>285 | Gly | Ala | Ser |
| Pro | Asp<br>290 | Tyr | Asn | Ser | Ser | Glu<br>295 | Tyr | Glu | Gly | Pro | Leu<br>300 | Ser | Pro | Pro | Leu |
| Cys<br>305 | Leu | Asn | Gly | Asn | Phe<br>310 | Ser | Leu | Lys | Gln | Asp<br>315 | Ser | Ser | Pro | Asp | His<br>320 |
| Glu | Lys | Ser | Tyr | His<br>325 | Tyr | Ser | Met | His | Tyr<br>330 | Ser | Ala | Leu | Pro | Gly<br>335 | Ser |
| Arg | His | Gly | His<br>340 | Gly | Leu | Val | Phe | Gly<br>345 | Ser | Ser | Ala | Val | Arg<br>350 | Gly | Gly |
| Val | His | Ser<br>355 | Glu | Asn | Leu | Leu | Ser<br>360 | Tyr | Asp | Met | His | Leu<br>365 | His | His | Asp |
| Arg | Gly<br>370 | Pro | Met | Tyr | Glu<br>375 | Glu | Leu | Asn | Ala | Phe<br>380 | Phe | His | Asn |

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vii) IMMEDIATE SOURCE:
(B) CLONE: JL34

(xi) SEQUENCE DESCRIPTION: SEQ ID NO:18:

CTCAGCATCA GCAACTCGGC    20

(2) INFORMATION FOR SEQ ID NO:19:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: cDNA (v i i) IMMEDIATE SOURCE:
    (B) CLONE: JL36

(x i) SEQUENCE DESCRIPTION: SEQ ID NO:19:

TCGGATCCCG TTCTAGGCGC GCCTTGGTC                                                               29

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (v i i) IMMEDIATE SOURCE:
        (B) CLONE: JL40

(x i) SEQUENCE DESCRIPTION: SEQ ID NO:20:

GTTTCCCAG TCACGACGTT G                                                                         21

(2) INFORMATION FOR SEQ ID NO:21:

(i) SEQUENCE CHARACTERISTICS:
        (A) LENGTH: 1333 base pairs
        (B) TYPE: nucleic acid
        (C) STRANDEDNESS: double
        (D) TOPOLOGY: linear (ii) MOLECULE TYPE: DNA (genomic)

(v i) ORIGINAL SOURCE:
        (A) ORGANISM: Mus musculus (v i i) IMMEDIATE SOURCE:
        (B) CLONE: neuroD3

(i x) FEATURE:
        (A) NAME/KEY: CDS
        (B) LOCATION: 101..835

(x i) SEQUENCE DESCRIPTION: SEQ ID NO:21:

CTGCAGAGGA CAGGTAGCCC CGGGTCGTAC GGACAGTAAG TGCGCTTCGA AGGCCGACCT                               60

CCAAACCTCC TGTCCGTCTG TCGGTCCTGC ACACTGCAAG ATG CCT GCC CCT TTG                                115
                                                Met Pro Ala Pro Leu
                                                 1               5

GAG ACC TGC ATC TCT GAT CTC GAC TGC TCC AGC AGC AAC AGC AGC AGC                                163
Glu Thr Cys Ile Ser Asp Leu Asp Cys Ser Ser Ser Asn Ser Ser Ser
             10              15                  20

GAC CTG TCC AGC TTC CTC ACC GAC GAG GAG GAC TGT GCC AGG CTA CAG                                211
Asp Leu Ser Ser Phe Leu Thr Asp Glu Glu Asp Cys Ala Arg Leu Gln
                 25              30                  35

CCC CTA GCC TCC ACC TCG GGG CTG TCC GTG CCA GCC CGG AGG AGC GCT                                259
Pro Leu Ala Ser Thr Ser Gly Leu Ser Val Pro Ala Arg Arg Ser Ala
             40              45                  50

CCC GCC CTC TCC GGG GCA TCG AAT GTT CCC GGT GCC CAG GAC GAA GAG                                307
Pro Ala Leu Ser Gly Ala Ser Asn Val Pro Gly Ala Gln Asp Glu Glu
         55              60                  65

CAG GAA CGG CGG AGG CGG CGA GGT CGC GCT CGG GTG CGG TCC GAG GCT                                355
Gln Glu Arg Arg Arg Arg Arg Gly Arg Ala Arg Val Arg Ser Glu Ala
 70              75                  80                       85

CTG CTG CAC TCC CTG CGG AGG AGT CGT CGC GTC AAA GCC AAC GAT CGC                                403
Leu Leu His Ser Leu Arg Arg Ser Arg Arg Val Lys Ala Asn Asp Arg
                     90                  95                  100

GAG CGC AAC CGC ATG CAC AAC CTC AAC GCT GCG CTG GAC GCC TTG CGC                                451
Glu Arg Asn Arg Met His Asn Leu Asn Ala Ala Leu Asp Ala Leu Arg

|  |  |  |  |  |  |  |  |  |  |  |  |  |  |  |  |  |
|---|---|---|---|---|---|---|---|---|---|---|---|---|---|---|---|---|
|  | 105 |  |  |  |  |  | 110 |  |  |  |  |  | 115 |  |  |  |
| AGC | GTG | CTG | CCC | TCG | TTC | CCC | GAC | GAC | ACC | AAG | CTC | ACC | AAG | ATT | GAG | 499 |
| Ser | Val | Leu | Pro | Ser | Phe | Pro | Asp | Asp | Thr | Lys | Leu | Thr | Lys | Ile | Glu |  |
|  |  | 120 |  |  |  |  |  | 125 |  |  |  |  | 130 |  |  |  |
| ACG | CTG | CGC | TTC | GCC | TAC | AAC | TAC | ATC | TGG | GCC | CTG | GCT | GAG | ACA | CTG | 547 |
| Thr | Leu | Arg | Phe | Ala | Tyr | Asn | Tyr | Ile | Trp | Ala | Leu | Ala | Glu | Thr | Leu |  |
|  |  | 135 |  |  |  |  | 140 |  |  |  |  |  | 145 |  |  |  |
| CGC | CTG | GCA | GAT | CAA | GGG | CTC | CCC | GGG | GGC | AGT | GCC | CGG | GAG | CGC | CTC | 595 |
| Arg | Leu | Ala | Asp | Gln | Gly | Leu | Pro | Gly | Gly | Ser | Ala | Arg | Glu | Arg | Leu |  |
| 150 |  |  |  |  |  |  | 155 |  |  |  |  | 160 |  |  | 165 |  |
| CTG | CCT | CCG | CAG | TGT | GTC | CCC | TGT | CTG | CCC | GGG | CCC | CCG | AGC | CCG | GCC | 643 |
| Leu | Pro | Pro | Gln | Cys | Val | Pro | Cys | Leu | Pro | Gly | Pro | Pro | Ser | Pro | Ala |  |
|  |  |  |  | 170 |  |  |  |  | 175 |  |  |  |  | 180 |  |  |
| AGC | GAC | ACT | GAG | TCC | TGG | GGT | TCC | GGG | GCC | GCT | GCC | TCC | CCC | TGC | GCC | 691 |
| Ser | Asp | Thr | Glu | Ser | Trp | Gly | Ser | Gly | Ala | Ala | Ala | Ser | Pro | Cys | Ala |  |
|  |  |  | 185 |  |  |  |  | 190 |  |  |  |  | 195 |  |  |  |
| ACT | GTG | GCA | TCA | CCA | CTC | TCT | GAC | CCC | AGT | AGT | CCC | TCG | GCT | TCA | GAA | 739 |
| Thr | Val | Ala | Ser | Pro | Leu | Ser | Asp | Pro | Ser | Ser | Pro | Ser | Ala | Ser | Glu |  |
|  |  | 200 |  |  |  |  |  | 205 |  |  |  | 210 |  |  |  |  |
| GAC | TTC | ACC | TAT | GGC | CCG | GGC | GAT | CCC | CTT | TTC | TCC | TTT | CCT | GGC | CTG | 787 |
| Asp | Phe | Thr | Tyr | Gly | Pro | Gly | Asp | Pro | Leu | Phe | Ser | Phe | Pro | Gly | Leu |  |
|  | 215 |  |  |  |  | 220 |  |  |  |  | 225 |  |  |  |  |  |
| CCC | AAA | GAC | CTG | CTC | CAC | ACG | ACG | CCC | TGT | TTC | ATC | CCA | TAC | CAC | TAGGCCTTT | 842 |
| Pro | Lys | Asp | Leu | Leu | His | Thr | Thr | Pro | Cys | Phe | Ile | Pro | Tyr | His |  |  |
| 230 |  |  |  |  | 235 |  |  |  |  | 240 |  |  |  | 245 |  |  |

TAAGGCAACA TCAATACATT CTTCCTCCCC CAGTCAAGA GCAATAATAG ATGGGGAACT 902

GGCTGAAGCC TCCGGGGGCC ACACTTACCC CCAAGTGAAT TCTGGGAGCT TTAAAGGGGG 962

GAGGGGGAAT ACCTGACCAC TTGTTAGGTT GCTGCACCCT CGCTGAAGCT GCCCTCGGTC 1022

TATTTCTCCA CCCCCAGCAC GGCCTCCCCC CCCCCCGCCC GCCCCAGAC GGCCTTTCGT 1082

TTTTGTTGCA CTTTCTGAAC TTCACAAAAC CTTCTTTGTG ACTGGCTCAG AACTGACCCC 1142

AGCCACCACT TCAGTGTGGT TTGGAAAAGG GACAGATGAG CCCCTGAAGA CGAGGTGAAA 1202

AGTCAATTTT ACAATTTGTA GAACTCTAAT GAAGAAAAAC GAGCATGAAA ATTCGGTTTG 1262

AGCCGGCTGA CAATACAATG GCAAGGCTTA AAAAGGAGCC ACAAGGAGTG GGCTTCATGC 1322

ATTATGGATC C 1333

( 2 ) INFORMATION FOR SEQ ID NO:22:

( i ) SEQUENCE CHARACTERISTICS:
( A ) LENGTH: 244 amino acids
( B ) TYPE: amino acid
( D ) TOPOLOGY: linear ( i i ) MOLECULE TYPE: protein ( x i ) SEQUENCE DESCRIPTION: SEQ ID NO:22:

| Met | Pro | Ala | Pro | Leu | Glu | Thr | Cys | Ile | Ser | Asp | Leu | Asp | Cys | Ser | Ser |
|---|---|---|---|---|---|---|---|---|---|---|---|---|---|---|---|
| 1 |  |  |  | 5 |  |  |  |  | 10 |  |  |  |  | 15 |  |

| Ser | Asn | Ser | Ser | Ser | Asp | Leu | Ser | Ser | Phe | Leu | Thr | Asp | Glu | Glu | Asp |
|---|---|---|---|---|---|---|---|---|---|---|---|---|---|---|---|
|  |  |  | 20 |  |  |  |  | 25 |  |  |  |  | 30 |  |  |

| Cys | Ala | Arg | Leu | Gln | Pro | Leu | Ala | Ser | Thr | Ser | Gly | Leu | Ser | Val | Pro |
|---|---|---|---|---|---|---|---|---|---|---|---|---|---|---|---|
|  |  |  | 35 |  |  |  |  | 40 |  |  |  |  | 45 |  |  |

| Ala | Arg | Arg | Ser | Ala | Pro | Ala | Leu | Ser | Gly | Ala | Ser | Asn | Val | Pro | Gly |
|---|---|---|---|---|---|---|---|---|---|---|---|---|---|---|---|
|  | 50 |  |  |  |  | 55 |  |  |  |  | 60 |  |  |  |  |

| Ala | Gln | Asp | Glu | Glu | Gln | Glu | Arg | Arg | Arg | Arg | Gly | Arg | Ala | Arg |
|---|---|---|---|---|---|---|---|---|---|---|---|---|---|---|
| 65 |  |  |  |  | 70 |  |  |  |  | 75 |  |  |  | 80 |

Val Arg Ser Glu Ala Leu Leu His Ser Leu Arg Arg Ser Arg Arg Val

|     |     |     |     |     |     |     |     | 85  |     |     |     |     | 90  |     |     |     |     | 95  |     |
| --- | --- | --- | --- | --- | --- | --- | --- | --- | --- | --- | --- | --- | --- | --- | --- | --- | --- | --- | --- |
| Lys | Ala | Asn | Asp | Arg | Glu | Arg | Asn | Arg | Met | His | Asn | Leu | Asn | Ala | Ala |
|     |     |     | 100 |     |     |     |     | 105 |     |     |     |     | 110 |     |     |
| Leu | Asp | Ala | Leu | Arg | Ser | Val | Leu | Pro | Ser | Phe | Pro | Asp | Asp | Thr | Lys |
|     |     | 115 |     |     |     |     | 120 |     |     |     |     | 125 |     |     |     |
| Leu | Thr | Lys | Ile | Glu | Thr | Leu | Arg | Phe | Ala | Tyr | Asn | Tyr | Ile | Trp | Ala |
|     | 130 |     |     |     |     | 135 |     |     |     |     | 140 |     |     |     |     |
| Leu | Ala | Glu | Thr | Leu | Arg | Leu | Ala | Asp | Gln | Gly | Leu | Pro | Gly | Gly | Ser |
| 145 |     |     |     |     | 150 |     |     |     |     | 155 |     |     |     |     | 160 |
| Ala | Arg | Glu | Arg | Leu | Leu | Pro | Pro | Gln | Cys | Val | Pro | Cys | Leu | Pro | Gly |
|     |     |     |     | 165 |     |     |     |     | 170 |     |     |     |     | 175 |     |
| Pro | Pro | Ser | Pro | Ala | Ser | Asp | Thr | Glu | Ser | Trp | Gly | Ser | Gly | Ala | Ala |
|     |     |     | 180 |     |     |     |     | 185 |     |     |     |     | 190 |     |     |
| Ala | Ser | Pro | Cys | Ala | Thr | Val | Ala | Ser | Pro | Leu | Ser | Asp | Pro | Ser | Ser |
|     |     | 195 |     |     |     |     | 200 |     |     |     |     | 205 |     |     |     |
| Pro | Ser | Ala | Ser | Glu | Asp | Phe | Thr | Tyr | Gly | Pro | Gly | Asp | Pro | Leu | Phe |
|     | 210 |     |     |     |     | 215 |     |     |     |     | 220 |     |     |     |     |
| Ser | Phe | Pro | Gly | Leu | Pro | Lys | Asp | Leu | Leu | His | Thr | Thr | Pro | Cys | Phe |
| 225 |     |     |     |     | 230 |     |     |     |     | 235 |     |     |     |     | 240 |
| Ile | Pro | Tyr | His |

( 2 ) INFORMATION FOR SEQ ID NO:23:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:23:

GTCACAAGTC AGCGCCCAAG                                        2 0

( 2 ) INFORMATION FOR SEQ ID NO:24:

( i ) SEQUENCE CHARACTERISTICS:
    ( A ) LENGTH: 20 nucleotides
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:24:

CGACGAGTAG GATGAGACCG                                        2 0

EXPRESSION OF NEUROGENIC BHLH GENES IN PRIMITIVE NEUROECTODERMAL TUMORS

This application is a continuation-in-part of PCT application No. PCT/US96/17532, filed Oct. 30, 1996, which is a continuation-in-part of U.S. application Ser. No. 08/552,142, filed Nov. 2, 1995, now U.S. Pat. No. 5,695,995, which is a continuation-in-part of PCT application No. PCT/US95/05741, filed May 8, 1995, which is a continuation-in-part of parent application U.S. Ser. No. 08/239,238, filed May 6, 1994 (abandoned).

This invention was made with government support under grant CA42506 awarded by the National Institutes of Health. The government has certain rights in the invention.

FIELD OF THE INVENTION

The invention relates to molecular biology and in particular to genes and proteins involved in vertebrate neural development and to methods for classifying and prognosticating neuroectodermal tumors.

BACKGROUND OF THE INVENTION

Transcription factors of the basic-helix-loop-helix (bHLH) family are implicated in the regulation of differentiation in a wide variety of cell types, including trophoblast cells (Cross et al., *Development* 121:2513–2523, 1995), pigment cells (Steingrimsson et al., *Nature Gen.* 8:251–255, 1994), B-cells (Shen, C. P. and T. Kadesch., *Molec. & Cell. Biol.* 15:3813–3822, 1995; Zhuang et al., *Cell* 79:875–884, 1994), chondrocytes and osteoblasts (Cserjesi et al., *Development* 121:1099–1110, 1995; Tamura, M. and M. Noda., *J. Cell Biol.* 126:773–782, 1994), and cardiac muscle (Burgess et al., *Develop. Biol.* 168:296–306, 1995; Hollenberg et al., *Molec. & Cell. Biol.* 15:3813–3822, 1995). bHLH proteins form homodimeric and heterodimeric complexes that bind with DNA in the 5' regulatory regions of genes controlling expression.

Perhaps the most extensively studied sub-families of bHLH proteins are those that regulate myogenesis and neurogenesis. The myogenic bHLH factors, (MyoD, myogenin, Myf5, and MRF4), appear to have unique as well as redundant functions during myogenesis (Weintraub, H., *Cell* 75:1241–1244, 1993; Weintraub et al., *Science* 251:761–766, 1991). It is thought that either Myf5 or MyoD is necessary to determine myogenic fate, whereas myogenin is necessary for events involved in terminal differentiation (Hasty et al., *Nature* 364:501–506, 1993; Nabeshima et al., *Nature* 364:532–535, 1993; Rudnicki et al., *Cell* 75:1351–1359, 1993; Venuti et al., *J. Cell Biol.* 128:563–576, 1995). Moreover, Myf expression has been observed in a number of rhabdomyosarcomas, and has been proposed as a marker for that category of tumor (Clark et al., *Br. J. Cancer* 64:1039–1042, 1991).

Recent work on neurogenic bHLH proteins suggests parallels between the myogenic and neurogenic sub-families of bHLH proteins. Genes of the *Drosophila melanogaster* achaete-scute complex and the atonal gene have been shown to be involved in neural cell fate determination (Anderson, D. J., *Cur. Biol.* 5:1235–1238, 1995; Campuzano, S. and J. Modolell., *Trends in Genetics* 8:202–208, 1992; Jaman et al., *Cell* 73:1307–1321, 1993), and the mammalian homologs, MASH1 and MATH1, are expressed in the neural tube at the time of neurogenesis (Akazawa et al., *J. Biol. Chem.* 270:8730–8738, 1995; Lo et al., *Genes & Dev.* 5:1524–1537, 1991). Two related vertebrate bHLH proteins, neuroD1 and NEX-1/MATH-2, are expressed slightly later in CNS development, predominantly in the marginal layer of the neural tube and persisting in the mature nervous system (Bartholoma, A. and K. A. Nave, *Mech. Dev.* 48:217–228, 1994; Lee et al., *Science* 268:836–844, 1995; Shimizu et al., *Eur. J. Biochem.* 229:239–248, 1995). NeuroD1 was also cloned as a factor that regulates insulin transcription in pancreatic beta cells and named "Beta2" (Naya et al., *Genes & Dev.* 9:1009–1019, 1995). Constitutive expression of neuroD1 in developing Xenopus embryos produces ectopic neurogenesis in the ectodermal cells, indicating that neuroD genes are capable of regulating a neurogenic program. A neuroD1 homolog having 36,873 nucleotides has been identified in *C. elegans* (Lee et al., 1995; Genbank Accession No. 010402), suggesting that this molecular mechanism of regulating neurogenesis may be conserved between vertebrates and invertebrates.

A human achaete-scute homolog has been identified and cloned whose predicted protein of 238 amino acids is 95% homologous to the mouse hash1 gene (Ball et al., *Proc. Natl. Acad. Sci. USA* 90:5648–5652, 1993). Northern blots revealed that transcripts from this bHLH gene were detectable in two types of cancer with neuroendocrine features, namely small cell lung cancer, and the calcitonin-secreting medullary thyroid carcinoma (id.). Thus, hash1 was proposed to provide a marker for cancers with neuroendocrine features.

Primitive neuroectodermal tumors (PNET) are the most common of the malignant central nervous system tumors that occur in children (Biegel et al., *Genes, Chrom. & Cancer* 14:85–96, 1995). Both supratentorial and infratentorial PNETs occur. Medulloblastoma, an infratentorial tumor that expresses neuronal intermediate filaments, synaptic vesicle proteins, growth factor receptors, and adhesion molecules, is the prototypic PNET. The location (posterior fossa) and properties of medulloblastomas suggests that they arise from neuroblasts that escape terminal differentiation (Trojanowski, J. Q., et al. *Mol. Chem. Neuropathol.* 17:121–135, 1992). Abnormalities in chromosome 17 have been observed in PNET biopsies, though the significance of these abnormalities has not been determined (Biegel et al., 1995; Schultz, et al., *Genes, Chrom. & Cancer* 16:196–203, 1996). Factors presently used to classify and prognosticate brain tumors include location, histopathology, patient age, and biological behavior of the tumor. However, such bases for tumor identification are not always sufficient for accurate prognostication. Supratentorial and infratentorial PNETs cannot always be distinguished, though they may respond differently to therapy. (Heideman, R. L. et al. "Tumors of the central nervous system." In: P. A. Pizzo and D. G. Poplack (eds.), *Principles and Practice of Pediatric Oncology*, 2nd. ed., pp. 633–682, 1993; Rorke, L. B., et al. *Cancer* 56:1869–1886, 1996; Packer, R. J., et al. *J. Neurosurg.* 81:690–698, 1994; Cohen, B. H. et al. *J. Clin. Oncol.* 13:1687–1696, 1995).

Because different types of brain tumors respond differently to various therapeutic regimens, accurate classification is highly useful to the physician in determining the best course of treatment for a particular patient. Medulloblastomas about half of the time are confined to the bridge that connects the two halves of the cerebellum (vermis). Medulloblastoma often is an aggressive and highly malignant type of tumor, and may invade other portions of the brain and spinal column. Thus, diagnosis based on location is not always reliable. Histologically, medulloblastoma is highly cellular, consisting of undifferentiated small dark round cells. Other PNETs with an identical histologic appearance, occurring predominantly in infants, are found at other locations in the brain. Thus, markers for a more accurate determination of PNET origin would facilitate the assignment of the therapeutic regimen most likely to be effective. Currently, no effective biologic markers exist for facilitating the stratification of treatment groups, assisting in prognosis, or providing targets for therapeutic intervention (Heideman et al., 1993).

SUMMARY OF THE INVENTION

The presently disclosed neuroD proteins represent a new sub-family of bHLH proteins and are implicated in vertebrate neuronal, endocrine and gastrointestinal development. Mammalian and amphibian neuroD proteins have been identified, and polynucleotide molecules encoding neuroD proteins have been isolated and sequenced. NeuroD genes encode proteins that are distinctive members of the bHLH family. In addition, the present invention provides a family of neuroD proteins that share a highly conserved HLH region. Representative polynucleotide molecules encoding members of the neuroD family include neuroD1, neuroD2 and neuroD3.

A representative nucleotide sequence encoding murine neuroD1 is shown in SEQ ID NO:1. The HLH coding domain of murine neuroD1 resides between nucleotides 577 and 696 in SEQ ID NO:1. The deduced amino acid sequence of murine neuroD1 is shown in SEQ ID NO:2. There is a highly conserved region following the helix-2 domain from amino acid 150 through amino acid 199 of SEQ ID NO:2 that is not shared by other bHLH proteins.

A representative nucleotide sequence encoding Xenopus neuroD1 is shown in SEQ ID NO:3. The HLH coding domain of Xenopus neuroD1 resides between nucleotides 376 and 495 in SEQ ID NO:3. The deduced amino acid sequence of Xenopus neuroD1 is shown in SEQ ID NO:4. There is a highly conserved region following the helix-2 domain from amino acid 157 through amino acid 199 of SEQ ID NO:4 that is not shared by other bHLH proteins.

Representative nucleotide and deduced amino acid sequences of the human neuroD family are shown in SEQ ID NOS:8-15. Representative nucleotide and deduced amino acid sequences of a human homolog of murine neuroD1 are shown in SEQ ID NOS:8 and 9 (partial genomic sequence) and SEQ ID NOS:14 and 15 (human neuroD1 cDNA). Representative nucleotide and deduced amino acid sequences of the human and murine neuroD2 are shown in SEQ ID NOS: 10 and 11, and 16 and 17, respectively. Representative nucleotide and deduced amino acid sequences for human neuroD3 are shown in SEQ ID NOS:12 and 13. The disclosed human clones, 9F1 (and its corresponding cDNA HC2A; now referred to as human neuroD1) and 14B1 (now referred to as human neuroD2), have an identical HLH motif: Amino acid residues 117-156 in SEQ ID NO:9 and 15, and residues 137-176 in SEQ ID NO:11 (corresponding to nucleotides 405-524 of SEQ ID NO:8 and SEQ ID NO:14, and nucleotides 463-582 of SEQ ID NO:10). Comparison of the deduced amino acid sequences of these neuroD genes shows that human neuroD3 contains an HLH domain between amino acid residues 108-147 of SEQ ID NO:13 (corresponding to nucleotides 376-495 of SEQ ID NO:12) and that murine neuroD2 contains an HLH domain between amino acids residues 138-177 of SEQ ID NO:17 (corresponding to nucleotides 641-760 of SEQ ID NO:16). The HLH domain of murine neuroD2 is identical to that of the human neuroD1 and human neuroD2 proteins. Similar analyses indicated that mouse neuroD3 contains an HLH domain between amino acid residues 109-148 of SEQ ID NO:22 (corresponding to nucleotides 425-544 of SEQ ID NO:21).

Expression of several bHLH genes were analyzed in cerebellar and cerebral primitive neuroectodermal tumors (PNETs), gliomas, and in cell lines derived from a variety of neuroectodermal tumors. Generally, the observed patterns of neuroD expression distinguished subclasses of neuroectodermal tumors and generally recapitulated gene expression patterns of tissues from which neuroectodermal tumors arise. For example, a striking association of neuroD3 with aggressive cases of medulloblastoma was noted, suggesting that neuroD3 provides a useful prognosticator for aggressive medulloblastoma.

DETAILED DESCRIPTION OF THE PREFERRED EMBODIMENT

The subject invention provides three representative members of the neuroD family of genes, namely, neuroD1, neuroD2 and neuroD3 (also called "neurogenin"). More specifically, the invention provides murine neuroD1 (SEQ ID NOS:1 and 2, Xenopus laevis neuroD1 (SEQ ID NOS:3 and 4, human neuroD1 (SEQ ID NOS:8, 9, 14, and 15, human neuroD2 (SEQ ID NOS:10 and 11), human neuroD3 (SEQ ID NOS:12 and 13), murine neuroD2 (SEQ ID NOS:16 and 17), and murine neuroD3 (SEQ ID NOS:21 and 22).

Provided are methods of classifying human neuroectodermal tumors by analyzing a sample of the tumor, such as, for example, a biopsy or a sample of an excised tumor. For this analysis, the expression of at least one basic helix loop (bHLH) gene is measured in the sample, and the tumor is classified as belonging to a particular subclass of neuroectodermal tumor in accord with the observed expression pattern. Examples of neuroectodermal tumor subclasses amenable to this analysis include supratentorial PNETs, such as neuroblastoma, as well as infratentorial PNETs, such as medulloblastoma. Predetermined profiles of bHLH expression associated with particular subclasses of neuroectodermal tumors are established by collecting tumor samples that have been classified by conventional methods, analyzing them for bHLH expression, and correlating the observed patterns of expression with the various subclasses of tumor. It is demonstrated that bHLH expression in several instances correlates with tumor subclass, and it is contemplated that these methods will be applicable to additional subclasses of neuroectodermal tumors. NeuroD genes whose measurement is useful in this context include neuroD1, neuroD2, neuroD3, but it is contemplated that additional neuroD family members will also contribute to this method of tumor classification. Hence, at least one, and preferably several, bHLH genes are analyzed in each tumor sample. For example, individual tumor samples may be analyzed for the expression of neuroD1, neuroD2, and neuroD3. It is determined that the tumor belongs to a given subclass of neuroectadermal tumors if the bHLH gene or genes expressed in the sample corresponds to a predetermined profile of basic helix loop helix expression associated with that subclass of neuroectodermal tumor.

Tumor samples typically will be obtained during excision of the tumor from the patient's brain, but may be obtained by other means, such as a biopsy or a spinal tap. Alternatively, the tumor sample may be obtained from the site of a metastatic tumor that originated from a brain tumor but that is located outside the brain cavity. Such metastatic tumors may appear in any part of the body, but most often are found in the spinal cord. Tumor samples also may be obtained from spinal fluid, which may be analyzed directly, or may be subjected to centrifugation to collect cellular material which in turn is analyzed.

The term "bHLH expression" refers to expression of the bHLH gene in the form of transcripts and/or polypeptide products. bHLH expression thus can be measured by using assays that detect bHLH RNA or polypeptides. bHLH transcripts typically are measured by hybridization under stringent conditions of RNA from the tumor sample with DNA or RNA probes corresponding specifically to the nucleotide sequences of non-conserved regions of cloned bHLH cDNAs, genes, or subportions thereof. By "non-conserved region" is meant that the probe does not encode the conserved bHLH domain itself. Hybridization methods for detecting bHLH transcripts include hybridization in solution, Northern blot analysis, dot blot or slot blot analysis, in situ hybridization, hybridizations wherein the probe is anchored to a solid substratum, liquid hybridization wherein the formed duplexes are subsequently captured on a solid substratum, or other methods of hybridization. Probes may be labeled directly, e.g., with radioisotopes or biotin, or may contain nucleotide sequences complementary to a secondary probe that itself is labeled.

The term "capable of hybridizing under stringent conditions" means that the probe anneals under stringent hybridization conditions to the target nucleic acid molecule. Individual probe molecules are generally between 7–1000 nucleotides in length, and preferably are between 10 and 650 nucleotides in length. Probe molecules longer than 1000 nucleotides may be used, but it is preferable that these be sheared to fragments of 200–500 nucleotides in length prior to use. Long DNA molecules to be used as probes may be sheared mechanically, enzymatically, or by brief alkali treatment.

"Stringent hybridization" is generally understood in the art to mean that the nucleic acid duplexes that form during the hybridization reaction are perfectly matched or nearly perfectly matched. Several rules governing nucleic acid hybridization have been well established. For example, it is standard practice to achieve stringent hybridization for polynucleotide molecules >200 nucleotides in length by hybridizing at a temperature 15°–25° C. below the melting temperature (Tm) of the expected duplex, and 5°–10° C. below the Tm for oligonucleotide probes (e.g., Sambrook et al., *Molecular Cloning*, [2d ed.], Cold Spring Harbor Laboratory Press, 1989, which is hereby incorporated by reference; see Section 11.45). Under such conditions, stable hybrid duplexes will form only if few or no mismatches are present. When Northern or Southern blots are performed, the detection of only well-matched hybrids can be assured by conducting the hybridization step under low or moderate stringency conditions, and then conducting the final wash steps under stringent wash conditions, i.e., at about 10°–14° C. below the Tm.

The Tm of a nucleic acid duplex can be calculated using a formula based on the % G+C contained in the nucleic acids, and that takes chain length into account, such as the formula Tm=81.5–16.6 (log [Na+])+0.41 (% G+C)–(600/N), where N=chain length (Sambrook et al., 1989, at Section 11.46). It is apparent from this formula that the effects of chain length on Tm is significant only when rather short nucleic acids are hybridized, and also that the length effect is negligible for nucleic acids longer than a few hundred bases.

The term "capable of hybridizing under stringent conditions" as used herein means that the subject nucleic acid molecules (whether DNA or RNA) anneal under stringent hybridization conditions to an oligonucleotide probe of 15 or more contiguous nucleotides of SEQ ID NO:1, SEQ ID NO:3, SEQ ID NO:8, SEQ ID NO:10, SEQ ID NO:12, SEQ ID NO:14, SEQ ID NO:16, or SEQ ID NO:21. Oligonucleotides 15 nucleotides or more in length are extremely unlikely to be represented more than once in a mammalian genome, hence such oligonucleotides can form specific hybrids (see, for example, Sambrook et al., at Section 11.7).

The choice of hybridization conditions will be evident to one skilled in the art and will generally be guided by the purpose of the hybridization, the type of hybridization (DNA-DNA or DNA-RNA), and the level of desired relatedness between the sequences. See, for example: Sambrook et al., 1989.; Hames and Higgins, eds., *Nucleic Acid Hybridization, A Practical Approach*, IRL Press, Washington D.C., 1985; Berger and Kimmel, eds., *Methods in Enzymology*, Vol. 52, *Guide to Molecular Cloning Techniques*, Academic Press Inc., New York, N.Y., 1987; and Bothwell, Yancopoulos and Alt, eds., *Methods for Cloning and Analysis of Eukaryotic Genes*, Jones and Bartlett Publishers, Boston, Mass. 1990; which are incorporated by reference herein in their entirety. The stability of nucleic acid duplexes is known to decrease with an increased number of mismatched bases, and further to be decreased to a greater or lesser degree depending on the relative positions of mismatches in the hybrid duplexes. Thus, the stringency of hybridization may be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and/or salt concentration of the wash solutions. For filter hybridizations, the final stringency of hybridization often is determined by the salt concentration and/or temperature used for the post-hybridization washes. In general, the stringency of hybridization reaction itself may be reduced by reducing the percentage of formamide in the hybridization solution. High stringency conditions, for example, may involve high temperature hybridization (e.g., 65°–68° C. in aqueous solution containing 4–6×SSC (1×SSC=0.15M NaCl, 0.015M sodium citrate), or 42° C. in 50% formamide combined with washes at high temperature (e.g., 5°–25° C. below the Tm), in a solution having a low salt concentration (e.g., 0.1×SSC). Low stringency conditions may involve lower hybridization temperatures (e.g., 35°–42° C. in 20–50% formamide) with washes conducted at an intermediate temperature (e.g., 40°–60° C.) and in a wash solution having a higher salt concentration (e.g., 2–6×SSC). Moderate stringency conditions, which may involve hybridization in 0.2–0.3M NaCl at a temperature between 50° C. and 65° C. and washes in 0.1×SSC, 0.1% SDS at between 50° C. and 55° C., may be used in conjunction with the disclosed polynucleotide molecules as probes to identify genomic or cDNA clones encoding members of the neuroD family.

To measure the amount of bHLH protein in a sample, antibody-based methods can be used. For example, either monoclonal or polyclonal antibody directed against the target protein can be used in Western blots, radioimmunoassays (RIA), enzyme-linked immunosorbent assays (ELISA), or the like.

For purposes of the subject invention, bHLH expression is "detected" if the level of bHLH transcripts or protein is elevated above the background level in the assay that is conducted to measure the transcripts or protein. "Background level" is the level of signal observed in control reactions in which the target transcript or protein is not present.

In one embodiment of the invention, a method is provided wherein a human neuroectodermal tumor is classified as a medulloblastoma by measuring neuroD1 and neuroD3 expression in a sample of the tumor, and determining that the tumor is a medulloblastoma if both neuroD1 and neuroD3 expression are detected in the sample.

High level expression of neuroD in neuroendocrine tumors and in rapidly proliferating regions of embryonic neural development (see below) indicates that measuring the levels of expression of neuroD or other bHLH genes may provide prognostic markers for assessing the growth rate and invasiveness of a neural tumor. Provided here is a method for prognosticating a human medulloblastoma based on measuring the expression of neuroD3, which is expressed in some but not all medulloblastomas (see Table 1, Example 17). It is determined that the tumor is an aggressive medulloblastoma if neuroD3 expression above the background level is detected in the sample. By "prognosticating" is meant the foretelling of the probable course of a tumor in advance of treatment, and predicting the likelihood that treatment will be successful.

The neuroD family of genes function during the development of the nervous system. Like MATH1 (Lo et al., *Genes & Dev.* 5:1524–1537, 1991), the expression of neuroD3 peaks during embryonic development and is not detected in the mature nervous system. NeuroD2 shows a high degree of sequence similarity to both neuroD1 and NEX-1/MATH2, and is similarly expressed both during embryogenesis and in the mature nervous system, demonstrating an expression pattern that partially overlaps with neuroD1. Like neuroD1, neuroD2 when expressed by transfection in Xenopus embryos induces neurogenesis in ectodermal cells. Heterologous expression of neuroD1 and neuroD2 indicates that these highly similar transcription factors demonstrate some target specificity, with the GAP-43 promoter being activated by neuroD2 and not by neuroD1. The partially overlapping expression pattern and target specificity of neuroD1 and neuroD2 suggests that this group of neurogenic transcription factors may contribute to the establishment of neuronal identity in the nervous system by acting on an overlapping but non-congruent set of target genes.

NeuroD proteins are transiently expressed in differentiating neurons during embryogenesis. NeuroD proteins are also detected in adult brain, in the granule layer of the hippocampus and the cerebellum. In addition, murine neuroD1 expression has been detected in the pancreas and gastrointestinal tissues of developing embryos and post-natal mice (see, e.g., Example 14). NeuroD proteins contain the basic helix-loop-helix (bHLH) domain structure that has been implicated in the binding of bHLH proteins to upstream recognition sequences and activation of downstream target genes. Based on homology with other bHLH proteins, the bHLH domain for murine neuroD1 is predicted to reside between amino acids 102 and 155 of SEQ ID NO:2, and between amino acids 101 and 157 of SEQ ID NO:4 for the amphibian neuroD1.

NeuroD proteins are transcriptional activators that control transcription of downstream target genes including genes that among other activities cause neuronal progenitors to differentiate into mature neurons. In the neural stage of the mouse embryo (e10), murine neuroD1 is highly expressed in the neurogenic derivatives of neural crest cells, the cranial and dorsal root ganglia, and postmitotic cells in the central nervous system (CNS). During mouse development, neuroD1 is expressed transiently and concomitant with neuronal differentiation in differentiating neurons in sensory organs such as in nasal epithelium and retina. In Xenopus embryos, ectopic expression of neuroD1 in non-neuronal cells induced formation of neurons. As discussed in more detail below, neuroD proteins are expressed in differentiating neurons and are capable of causing the conversion of non-neuronal cells into neurons. The present invention encompasses variants of neuroD genes that, for example, are modified in a manner that results in a neuroD protein capable of binding to its recognition site, but unable to activate downstream genes. The present invention also encompasses fragments of neuroD proteins that, for example, are capable of binding the natural neuroD partner, but that are incapable of activating downstream genes. NeuroD proteins encompass proteins retrieved from naturally occurring materials and closely related, functionally similar proteins retrieved by antisera specific to neuroD proteins, and recombinantly expressed proteins encoded by genetic materials (DNA, RNA, cDNA) retrieved on the basis of their similarity to the unique regions in the neuroD family of genes.

The present invention provides representative isolated and purified polynucleotide molecules encoding proteins of the neuroD family. Polynucleotide molecules encoding neuroD include those sequences resulting in minor genetic polymorphisms, differences between species, and those that contain amino acid substitutions, additions, and/or deletions. According to the present invention, polynucleotide molecules encoding neuroD proteins encompass those molecules that encode neuroD proteins or peptides that share identity with the sequences shown in SEQ ID NOS:2, 4, 9, 11,13, 15, and 17.

In some instances, one may employ such changes in the sequence of a recombinant neuroD polynucleotide molecule to substantially decrease or even increase the biological activity of neuroD protein relative to the wild-type neuroD activity, depending on the intended use of the preparation. Such changes may also be directed towards endogenous neuroD polynucleotide sequences using, for example, gene therapy methods to alter the gene product. Such changes are envisioned with regard to neuroD1, neuroD2, neuroD3, or other members of the neuroD gene family.

The neuroD1 proteins of the present invention are capable of inducing the expression in a frog embryo of neuron-specific genes, such as N-CAM, β-tubulin, and Xen-1, neurofilament M (NF-M), Xen-2, tanabin-1, shaker-1, and frog HSCL. As described below in Example 10, neuroD1 activity may be detected when neuroD is ectopically expressed in frog oocytes following, for example, injection of Xenopus neuroD1 RNA into one of the two cells in a two-cell stage Xenopus embryo, and monitoring expression of neuronal-specific genes in the injected as compared to uninjected side of the embryo by immunochemistry or in situ hybridization.

"Over-expression" means an increased level of a neuroD protein or of neuroD transcripts in a recombinant transformed host cell or in a tumor cell relative to the level of protein or transcripts in the untransformed host cell or in the normal cell from which the tumor is derived.

As noted above, the present invention provides isolated and purified polynucleotide molecules encoding various members of the neuroD family. The disclosed sequences may be used to identify and isolate additional neuroD polynucleotide molecules from suitable mammalian or non-mammalian host cells such as canine, ovine, bovine, caprine, lagomorph, or avian. In particular, the nucleotide sequences encoding the HLH region may be used to identify polynucleotide molecules encoding other proteins of the neuroD family. Complementary DNA molecules encoding neuroD family members may be obtained by constructing a cDNA library mRNA from, for example, fetal brain, newborn brain, and adult brain tissues. DNA molecules encoding neuroD family members may be isolated from such a library using the disclosed sequences to provide probes to be used in standard hybridization methods (e.g., Sambrook et al., *Molecular Cloning: A Laboratory Manual, Second Edition,* Cold Spring Harbor, N.Y., 1989, which is incorporated herein by reference), and Bothwell, Yancopoulos and Alt, ibid.) or by amplification of sequences using polymerase chain reaction (PCR) amplification (e.g., Loh et al., *Science* 243:217–222, 1989; Frohman et al., *Proc. Natl. Acad. Sci. USA* 85:8998–9002, 1988; Erlich (ed.), *PCR Technology: Principles and Applications for DNA Amplification,* Stockton Press, 1989; and Mullis et al., *PCR: The Polymerase Chain Reaction,* 1994, which are incorporated by reference herein in their entirety). In a similar manner, genomic DNA encoding neuroD proteins may be obtained using probes designed from the sequences disclosed herein. Suitable probes for use in identifying neuroD genes or transcripts may be obtained from neuroD-specific sequences that are highly conserved regions between mammalian and amphibian neuroD coding sequences. Nucleotide sequences, for example, from the region encoding the approximately 40 residues following the helix-2 domain are suitable for use in designing PCR primers. Alternatively, oligonucleotides containing specific DNA sequences from a human neuroD1, neuroD2, or neuroD3 coding region may be used within the described methods to identify related human neuroD genomic and cDNA clones. Upstream regulatory regions of neuroD may be obtained using the same methods. Suitable PCR primers are between 7–50 nucleotides in length, more preferably between 15 and 25 nucleotides in length. Typically, probes must be at least 10 nucleotides in length to form stable hybrids. Alternatively, neuroD polynucleotide molecules may be isolated using standard hybridization techniques with probes of at least about 15 nucleotides in length and up to and including the full coding sequence. Southern analysis of mouse genomic DNA probed with the murine neuroD1 cDNA under stringent conditions showed the presence of only one gene, suggesting that under stringent conditions bHLH genes from other protein families will not be identified. Other members of the neuroD family can be identified using degenerate oligonucleotides based on the sequences disclosed herein for PCR amplification or by hybridization at moderate stringency using probes based on the disclosed sequences.

The regulatory regions of neuroD may be useful as tissue-specific promoters. Such regulatory regions may find use in, for example, gene therapy to drive the tissue-specific expression of heterologous genes in pancreatic, gastrointestinal, or neural cells, tissues or cell lines. As shown in Example 14, murine neuroD1 promoter sequences reside within the 1.4 kb 5' untranslated region. Regulatory sequences within this region are identified by comparison to other promoter sequences and/or deletion analysis of the region itself.

In other aspects of the invention, a DNA molecule coding a neuroD protein is inserted into a suitable expression vector, which is in turn used to transfect or transform a suitable host cell. Suitable expression vectors for use in carrying out the present invention include a promoter capable of directing the transcription of a polynucleotide molecule of interest in a host cell and may also include a transcription termination signal, these elements being operably linked in the vector. Representative expression vectors may include both plasmid and/or viral vector sequences. Suitable vectors include retroviral vectors, vaccinia viral vectors, CMV viral vectors, BLUESCRIPT vectors, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomegalovirus promoter (Boshart et al., *Cell* 41:521–530, 1985) and the SV40 promoter (Subramani et al., *Mol. Cell. Biol.* 1:854–864, 1981). Suitable cellular promoters for expression of proteins in mammalian host cells include the mouse metallothionine-1 promoter (Palmiter et al., U.S. Pat. No. 4,579,821), a mouse Vk promoter (Bergman et al., *Proc. Natl. Acad. Sci. USA* 81:7041–7045, 1983; Grant et al. *Nucleic Acid. Res.* 15:5496, 1987), and tetracycline-responsive promoter (Gossen and Bujard, *Proc. Natl. Acad. Sci. USA* 89:5547–5551, 1992, and Pescini et al., *Biochem. Biophys. Res. Comm.* 202:1664–1667, 1994). Also contained in the expression vectors, typically, is a transcription termination signal located downstream of the coding sequence of interest. Suitable transcription termination signals include the early or late polyadenylation signals from SV40 (Kaufman and Sharp, *Mol. Cell. Biol.* 2:1304–1319, 1982), the polyadenylation signal from the Adenovirus 5 e1B region, and the human growth hormone gene terminator (DeNoto et al., *Nucleic Acid. Res.* 9:3719–3730, 1981). Mammalian cells, for example, may be transfected by a number of methods including calcium phosphate precipitation (Wigler et al., *Cell* 14:725, 1978; Corsaro and Pearson, *Somatic Cell Genetics* 7:603, 1981; Graham and Van der Eb, *Virology* 52:456, 1973), lipofection, microinjection, and electroporation (Neumann et al., *EMBO J* 1:8410845, 1982). Mammalian cells can be transduced with viruses such as SV40, CMV, and the like. In the case of viral vectors, cloned DNA molecules may be introduced by infection of susceptible cells with viral particles. Retroviral vectors may be preferred for use in expressing neuroD proteins in mammalian cells particularly if the neuroD genes used for gene therapy (for review, see, Miller et al. *Methods in Enzymology* 217:581–599, 1994; which is incorporated herein by reference in its entirety). It may be preferable to use a selectable marker to identify cells that contain the cloned DNA. Selectable markers are generally introduced into the cells along with the cloned DNA molecules and include genes that confer resistance to drugs, such as neomycin, hygromycin, and methotrexate. Selectable markers may also complement auxotrophs in the host cell. Yet other selectable markers provide detectable signals, such as β-galactosidase to identify cells containing the cloned DNA molecules. Selectable markers may be amplifiable. Such amplifiable selectable markers may be used to amplify the number of sequences integrated into the host genome.

As would be evident to one of ordinary skill in the art, the polynucleotide molecules of the present invention may be expressed in *Saccharomyces cerevisiae,* filamentous fungi, and *E. coli.* Methods for expressing cloned genes in *Saccharomyces cerevisiae* are generally known in the art (see, "Gene Expression Technology," *Methods in Enzymology,* Vol. 185, Goeddel (ed.), Academic Press, San Diego, Calif., 1990; and "Guide to Yeast Genetics and Molecular Biology," *Methods in Enzymology,* Guthrie and Fink (eds.), Academic Press, San Diego, Calif., 1991, which are incorporated herein by reference). Filamentous fungi may also be used to express the proteins of the present invention; for example, strains of the fungi Aspergillus (McKnight et al., U.S. Pat. No. 4,935,349, which is incorporated herein by reference). Methods for expressing genes and cDNAs in cultured mammalian cells and in *E. coli* are discussed in detail in Sambrook et al., 1989. As will be evident to one skilled in the art, one can express the protein of the instant invention in other host cells such as avian, insect, and plant cells using regulatory sequences, vectors and methods well established in the literature.

NeuroD proteins produced according to the present invention may be purified using a number of established methods such as affinity chromatography using anti-neuroD antibodies coupled to a solid support. Fusion proteins of antigenic tag and neuroD can be purified using antibodies to the tag. Additional purification may be achieved using conventional purification means such as liquid chromatography, gradient centrifugation, and gel electrophoresis, among others. Methods of protein purification are known in the art (see generally, Scopes, R., *Protein Purification*, Springer-Verlag, N.Y., 1982, which is incorporated herein by reference) and may be applied to the purification of recombinant neuroD described herein.

The invention provides isolated and purified polynucleotide molecules encoding neuroD proteins that are capable of hybridizing under stringent conditions to an oligonucleotide of 15 or more contiguous nucleotides of SEQ ID NO:1, SEQ ID NO:3, SEQ ID NO:8, SEQ ID NO:O10, SEQ ID NO:12, SEQ ID NO:14, and/or SEQ ID NO:16, and also including the polynucleotide molecules complementary to the coding strands. The subject isolated neuroD polynucleotide molecules preferably encode neuroD proteins that trigger differentiation in ectodermal cells, particularly neuroectodermal stem cells, and in more committed cells of that lineage, for example, epidermal precursor cells, pancreatic and gastrointestinal cells. Such neuroD expression products typically form heterodimeric bHLH protein complexes that bind in the 5'-regulatory regions of target genes and enhance or suppress transcription of the target gene.

In some instances, cancer cells may contain a non-functional neuroD protein or may contain no neuroD protein due to genetic mutation or somatic mutations such that these cells fail to differentiate. For cancers of this type, the cancer cells may be treated in a manner to cause the overexpression of wild-type neuroD protein to force differentiation of the cancer cells. Detection of overexpressed neuroD or other neurogenic differentiation factors may serve to identify different types of brain tumors.

Antisense neuroD nucleotide sequences, that is, nucleotide sequences complementary to the non-transcribed strand of a neuroD gene, may be used to block expression of mutant neuroD expression in neuronal precursor cells to generate and harvest neuronal stem cells or, alternatively, to suppress inappropriately expressed neuroD in tumor cells. The use of antisense oligonucleotides and their applications have been reviewed in the literature (see, for example, Mol and Van der Krul, eds., *Antisense Nucleic Acids and Proteins Fundamentals and Applications*, New York, N.Y., 1992; which is incorporated by reference herein in its entirety). Suitable antisense oligonucleotides are at least 11 nucleotide in length and may include untranslated (upstream or intron) and associated coding sequences. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, sites that interfere with ribosome progression, and 5' untranslated regions (promoter/enhancer) of the target gene. Antisense oligonucleotides may be prepared synthetically or by the insertion of a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense oligonucleotides. Synthetic oligonucleotides may be introduced, e.g., by electroporation, calcium phosphate precipitation, liposomes, or microinjection. Synthetic antisense oligonucleotides may be stabilized, e.g., by using intercalating agents that are covalently attached to either or both ends of the oligonucleotide, or by being made nuclease resistant by modifications to the phosphodiester backbone by the introduction of phosphotriesters, phosphonates, phosphorothioates, phosphoroselenoates, phosphoramidates, phosphorodithioates, or by using alpha-anomers of the deoxyribonucleotides.

NeuroD proteins bind to 5' regulatory regions of neurogenic genes that are involved in neuroectodermal differentiation, including development of neural and endocrine tissues. As described in the Examples given below, murine neuroD1 has been detected in neuronal, pancreatic and gastrointestinal tissues in embryonic and adult mice suggesting that neuroD1 functions in the transcription regulation in these tissues. NeuroD proteins alter the expression of subject genes by, for example, down-regulating or up-regulating transcription, or by inducing a change in transcription to an alternative open reading frame.

DNA sequences recognized by the various neuroD proteins may be determined using a number of methods known in the literature including immunoprecipitation (Biedenkapp et al., *Nature* 335:835–837, 1988; Kinzler and Vorgelstein, *Nuc. Acids Res.* 17:3645–3653, 1989; and Sompayrac and Danna, *Proc. Natl. Acad. Sci. USA* 87:3274–3278, 1990; which are incorporated by reference herein), protein affinity columns (Oliphant et al., *Mol. Cell. Biol.* 9:2944–2949, 1989; which is incorporated by reference herein), gel mobility shifts (Blackwell and Weintraub, *Science* 250:1104–1110, 1990; which is incorporated by reference herein), and Southwestern blots (Keller and Maniatis, *Nuc. Acids Res.* 17:4675–4680, 1991; which is incorporated by reference herein).

One embodiment of the present invention involves the construction of inter-species hybrid neuroD proteins and hybrid neuroD proteins containing at least one domain from two or more neuroD family members to facilitate structure-function analyses or to alter neuroD activity by increasing or decreasing the neuroD-mediated transcriptional activation of neurogenic genes relative to the wild-type neuroD(s). Hybrid proteins of the present invention may contain the replacement of one or more contiguous amino acids of the native neuroD protein with the analogous amino acid(s) of neuroD from another species or other protein of the neuroD family. Such interspecies or interfamily hybrid proteins include hybrids having whole or partial domain replacements. Such hybrid proteins are obtained using recombinant DNA techniques. Briefly, DNA molecules encoding the hybrid neuroD proteins of interest are prepared using generally available methods such as PCR mutagenesis, site-directed mutagenesis, and/or restriction digestion and ligation. The hybrid DNA is then inserted into expression vectors and introduced into suitable host cells. The biological activity may be assessed essentially as described in the assays set forth in more detail in the Examples that follow.

The invention also provides synthetic peptides, recombinantly derived peptides, fusion proteins, and the like that include a portion of neuroD or the entire protein. The subject peptides have an amino acid sequence encoded by a nucleic acid which hybridizes under stringent conditions with an oligonucleotide of 15 or more contiguous nucleotides of SEQ ID NO:1, SEQ ID NO:3, SEQ ID NO:8, SEQ ID NO:10, SEQ ID NO:12, SEQ ID NO:14, or SEQ ID NO:16. Representative amino acid sequences of the subject peptides are disclosed in SEQ ID NO:2, SEQ ID NO:4, SEQ ID NO:9, SEQ ID NO:11, SEQ ID NO:13, SEQ ID NO:15, and SEQ ID NO:17. The subject peptides find a variety of uses, including preparation of specific antibodies and preparation of agonists and antagonists of neuroD activity.

As noted above, the invention provides antibodies that bind to neuroD proteins. The production of non-human antisera or monoclonal antibodies (e.g., murine, lagormorph, porcine, equine) is well known and may be accomplished by, for example, immunizing an animal with neuroD protein or peptides. For the production of monoclonal antibodies, antibody producing cells are obtained from immunized animals, immortalized and screened, or screened first for the production of the antibody that binds to the neuroD protein or peptides and then immortalized. It may be desirable to transfer the antigen binding regions (e.g., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety. Alternatively, a human monoclonal antibody or portions thereof may be identified by first screening a human B-cell cDNA library for DNA molecules that encode antibodies that specifically bind to the neuroD family member, e.g., according to the method generally set forth by Huse et al. (*Science* 246:1275–1281, 1989, which is incorporated by reference herein in its entirety). The DNA molecule may then be cloned and amplified to obtain sequences that encode the antibody (or binding domain) of the desired specificity.

The invention also provides methods for inducing the expression of genes, such as neurotransmitters or neuromodulatory factors, that are associated with neuronal phenotype in a cell that does not normally express those genes. For example, the modulation of gene expression by neuroD can be carried out in cells of the neuroectodermal lineage, glial cells, neural crest cells, and epidermal epithelial basal stem cells, and all types of both mesodermal and endodermal lineage cells. NeuroD expression may also be used as a means of inducing expression of genes associated with pancreatic and gastrointestinal phenotype, e.g., insulin or gastrointestinal-specific enzymes.

As illustrated in Example 10, the expression of Xenopus neuroD1 protein in stem cells causes redirection of epidermal cell differentiation and induces terminal differentiation into neurons, i.e., instead of epidermal cells. Epithelial basal stem cells (i.e., in skin and mucosal tissues) are one of the few continuously regenerating cell types in an adult mammal. Introduction of the subject nucleotide sequences into an epithelial basal stem cell may be designed to achieve transient, constitutive, or regulated expression, and may be accomplished in vitro or in vivo using a suitable gene therapy vector delivery system (e.g., a retroviral vector), a microinjection technique (see, for example, Tam, *Basic Life Sciences* 37:187–194, 1986, which is incorporated by reference herein in its entirety), or a transfection method (e.g., naked or liposome encapsulated DNA or RNA; see, for example, *Trends in Genetics* 5:138, 1989; Chen and Okayama, *Biotechniques* 6:632–638, 1988; Mannino and Gould-Fogerite, *Biotechniques* 6:682–690, 1988; Kojima et al., *Biochem. Biophys. Res. Comm.* 207:8–12, 1995; which are incorporated by reference herein in their entirety).

Transformed host cells of the present invention are useful in vitro as convenient sources of neuronal and other growth factors for screening anti-cancer drugs capable of driving terminal differentiation in neural tumors, as sources of recombinantly expressed neuroD protein for use as an antigen in preparing monoclonal and polyclonal antibodies useful in diagnostic assays, and for screening for compounds capable of increasing or decreasing the activity of neuroD.

Transformed host cells of the present invention are also useful in vivo for transplantation at sites of traumatic neural injury where motor or sensory neural activity has been lost, e.g., for treating patients with hearing or vision loss due to optical or auditory nerve damage, patients with peripheral nerve damage and loss of motor or sensory neural activity, and patients with brain or spinal cord damage from traumatic injury. For example, donor cells from a patient such as epithelial basal stem cells are cultured in vitro and then transformed or transduced with a neuroD nucleotide sequence. The transformed cells are then returned to the patient by microinjection at the site of neural dysfunction. In addition, as neuroD appears capable of regulating expression of insulin, transformed host cells of the present invention may be useful for transplantation into patients with diabetes. For example, donor cells from a patient such as fibroblasts, pancreatic islet cells, or other pancreatic cells are harvested and transformed or transfected with a neuroD nucleotide sequence. The genetically engineered cells are then returned to the patient. In another embodiment, such engineered host cells may find use in the treatment of malabsorption syndromes.

Furthermore, the nucleotide sequences of the subject invention are useful for constructing cDNA and oligonucleotide probes for Northern or Southern blots, dot-blots, or PCR assays for identifying and quantifying the level of expression of neuroD in a cell. In addition, birth defects and spontaneous abortions may result from expression of an abnormal neuroD protein; thus, screening neuroD expression may be useful in prenatal screening of mothers in utero.

The neuroD sequences of the subject invention are also useful for constructing recombinant cell lines, ova, and transgenic embryos and animals including dominant-negative and "knock-out" recombinant cell lines in which the transcription regulatory activity of neuroD protein is down-regulated or eliminated. Such cells may contain altered neuroD coding sequences that result in the expression of a defective neuroD protein that is not capable of enhancing, suppressing or activating transcription of its target gene(s). The subject cell lines and animals find uses in screening for candidate therapeutic agents capable of either substituting for neuroD or correcting the cellular defect caused by a defective neuroD. Alternatively, cell lines expressing wild-type neuroD proteins may be useful for correcting birth defects that result from defective neuroD expression.

In addition, neuroD polynucleotide molecules may be joined to reporter genes, such as β-galactosidase or luciferase, and inserted into the genome of a suitable embryonic host cell such as a mouse embryonic stem cell by, for example, homologous recombination (for review, see Capecchi, *Trends in Genetics* 5:70–76, 1989; which is incorporated by reference). Cells expressing neuroD may then be obtained by subjecting the differentiating embryonic cells to cell sorting, leading to the purification of a population neuroblasts that are useful for studying neuroblast sensitivity to growth factors or chemotherapeutic agents that may be used as a source of neuroblast-specific protein products or gene transcripts.

As illustrated in Example 14. neuroD1 "knock-out" mice had diabetes, as demonstrated by blood glucose levels 2 and 3 times that of wild-type mice, and they died within four days of birth, while heterozygous mutants exhibited wild-type blood glucose levels. These results suggest that neuroD1 "knock-out" mice may be useful for studying methods to rescue homozygous mutants and as hosts to test transplant tissue for treating diabetes. These results suggest further that in vivo correction of neuroD1 deficiencies may therapeutically benefit diabetes patients.

The subject neuroD genes also are useful for constructing gene transfer vectors (e.g., retroviral vectors, and the like) wherein neuroD is inserted into the coding region of the vector under the control of a promoter. NeuroD gene therapy may be used to correct traumatic neural injury that has resulted in loss of motor or sensory neural function. For these therapies, gene transfer vectors may either be injected directly at the site of the traumatic injury, or the vectors may be used to construct transformed host cells that are then injected at the site of the traumatic injury. The results disclosed in Example 10 indicate that introduction of neuroD1 induces a non-neuronal cell to become a neuron. suggesting that transplantation and/or gene therapy with neuroD1 could be used to repair neural defects resulting from traumatic injury. NeuroD1 also may be useful for treating neurological disorders such as Alzheimer's disease, Huntington's disease, and Parkinson's disease, in which a population of neurons have been damaged. For such therapies, recombinant neuroD1 sequences may be introduced into existing neurons, or endogenous neuroD1 expression is induced in existing neurons in vivo. Alternatively, neuroD1 expression is induced in non-neuronal cells (e.g., glial cells in the brain or basal epithelial cells) to induce expression of genes that confer a complete or partial neuronal phenotype that ameliorates aspects of the disease. As an example, Parkinson's disease is caused, at least in part, by the death of neurons that supply the neurotransmitter dopamine to the basal ganglia. Increasing the levels of neurotransmitter ameliorates the symptoms of Parkinson's disease. Expression of neuroD1 in basal ganglia neurons or glial cells may induce aspects of a neuronal phenotype such that the neurotransmitter dopamine is produced directly in these cells. Alternatively, donor cells expressing a neuroD gene could be transplanted into the affected region. Also, neuroD1 can be expressed in non-pancreatic cells to induce expression of genes that confer a complete or partial pancreatic phenotype that ameliorates aspects of diabetes. Within yet another embodiment, neuroD1 is expressed in pancreatic islet cells to induce expression of genes that induce the expression of insulin.

The subject neuroD genes also are useful for the preparation of transplantable recombinant neuronal precursor cell populations from embryonic ectodermal cells, non-neural basal stem cells, and the like. The isolated polynucleotide molecules encoding neuroD proteins of the present invention permit the establishment of primary (or continuous) cultures of proliferating embryonic neuronal stem cells under conditions mimicking those that are active in development and cancer. The resultant cell lines find uses: i) as sources of novel neural growth factors, ii) in screening assays for anti-cancer compounds, and iii) in assays for identifying novel neuronal growth factors. For example, a high level of expression of neuroD was observed in the embryonic optic tectum, indicating that neuroD1 protein may regulate expression of factors trophic for growing retinal cells. Such cells may be useful sources of growth factors, and may be useful in screening assays for candidate therapeutic compounds.

The cell lines and transcription regulatory factors disclosed herein offer the unique advantage that since they are active very early in embryonic differentiation they represent potential switches, e.g., ON→OFF or OFF→ON, controlling subsequent cell fate. If the switch can be shown to be reversible (i.e., ON⇌OFF), the neuroD genes and proteins disclosed herein provide exciting opportunities for restoring lost neural and/or endocrine functions in a subject.

The following examples are offered by way of illustration and not by way of limitation.

EXAMPLE 1

Construction of the embryonic stem cell "179" cDNA library

A continuous murine embryonic stem cell line (i.e., the ES cell line) having mutant E2A (the putative binding partner of myoD) was used as a cell source to develop a panel of embryonic stem cell tumors. Recombinant ES stem cells were constructed (i.e., using homologous recombination) wherein both alleles of the putative myoD binding partner E2A were replaced with drug-selectable marker genes. ES cells do not make functional E12 or E47 proteins, both of which are E2A gene products. ES cells form subcutaneous tumors in congenic mice (i.e., strain 129J) that appear to contain representatives of many different embryonal cell types as judged histologically and through the use of RT-PCR gene expression assays. Individual embryonic stem cell tumors were induced in male 129J strain mice by subcutaneous injection of $1\times10^7$ cells/site. Three weeks later each tumor was harvested and used to prepare an individual sample of RNAs. Following random priming and second strand synthesis the ds-cDNAs were selected based on their size on 0.7% agarose gels and those cDNAs in the range of 400–800 bp were ligated to either Bam HI or Bgl II linkers. (Linkers were used to minimize the possibility that an internal Bam HI site in a cDNA might inadvertently be cut during cloning, leading to an abnormally sized or out-of-frame expression product.) The resultant individual stem cell tumor DNAs were individually ligated into the Bam HI cloning site in the "f1-VP16" 2µ yeast expression vector. This expression vector, f1-VP16, contains the VP16 activation domain of Herpes simplex virus (HSV) located between Hind III (HIII) and Eco RI (RI) sites and under the control of the *Saccharomyces cereviseae* alcohol dehydrogenase promoter; with LEU2 and Ampicillin-resistance selectable markers. Insertion of a DNA molecule of interest into the Hind III site of the f1-VP16 vector (i.e., 5' to the VP16 nucleotide sequence), or into a Bam HI site (i.e., 3' to the VP16 sequence but 5' to the Eco RI site), results in expression of a VP16 fusion protein having the protein of interest joined in-frame with VP16. The resultant cDNA library was termed the "179-library".

EXAMPLE 2

Identification and cDNA cloning of mouse neuroD1

A two-hybrid yeast screening assay was used essentially as described by Fields and Song (*Nature* 340:245, 1989) and modified as described herein was used to screen the 179-library described in Example 1. Yeast two-hybrid screens are reviewed as disclosed in Fields and Sternglanz (*Trends in*

Genetics 10:286–292, 1994). The library was screened for cDNAs that interacted with LexA-Da, a fusion protein between the Drosophila Da (Daughterless) bHLH domain and the prokaryotic LexA-DNA binding domain. The *S. cerevisiae* strain L40 contained multimerized LexA binding sites cloned upstream of two reporter genes, namely, the HIS3 gene, and the β-galactosidase gene, each of which was integrated into the L40 genome. The *S. cereviseae* strain L40 containing a plasmid encoding the LexA-Da fusion protein was transformed with CsCl gradient-purified f1-VP16-179-cDNA library. Transformants were maintained on medium selecting both plastids (the LexA-Da plasmid and the cDNA library plasmid) for 16 hours before being subjected to histidine selection on plates lacking histidine, leucine, tryptophan, uracil, and lysine. Clones that were HIS$^+$ were subsequently assayed for the expression of LacZ. To eliminate possible non-specific cloning artifacts, plasmids from HIS$^+$/LacZ$^+$ were isolated and transformed into *S. cereviseae* strain L40 containing a plasmid encoding a LexA-Lamin fusion. Clones that scored positive in the interaction with lamin were discarded. Approximately 400 cDNA clones, which represented 60 different transcripts, were identified as positive in these assays. Twenty-five percent of the original clones were subsequently shown to be known bHLH genes on the basis of their reactivity with specific cDNA probes. One cDNA clone encoding a VP16-fusion protein that interacted with Da but not lamin was identified as unique by sequence analysis. This clone, initially termed tango, is now referred to as neuroD1.

The unique cDNA identified above, VP 16-neuroD, contained an approximately 450 bp insert that spanned the bHLH region. Sequence analysis showed that the clone contained an insert encoding a complete bHLH amino acid sequence motif that was unique and previously unreported. Further analysis suggested that while the cDNA contained conserved residues common to all members of the bHLH protein family, several residues were unique and made it distinct from previously identified bHLH proteins. The DNA cloned in VP16-neuroD is referred to as "neuroD1." The neuroD1 cDNA insert was subcloned as a Bam HI-Not I insert into Bam HI-Not I linearized pBluescript SK$^+$. The resulting plasmid was designated pSK+1-83.

The neuroD1 insert contained in the VP16-neuroD plasmid was used to reprobe a mouse cDNA library prepared from mouse embryos at developmental stage e10.5. Candidate clones were isolated and sequenced essentially as described above. Several clones were isolated. One clone, designated pKS$^+$m7a RX, was deposited at the American Type Culture Collection, 12301 Parklawn Drive, Rockville, Md. 20852 USA, on May 6, 1994, under accession number 75768. Plasmid pKS$^+$m7a RX contains 1646 bp of murine neuroD1 cDNA as an EcoRI-XhoI insert. The amino acid sequence encoded by the insert begins at amino acid residue +73 and extends to the carboxy-terminus of the neuroD1 protein. The plasmid contains about 855 bp of neuroD1 coding sequence (encoding amino acids 73–536).

None of the mouse cDNAs contained the complete 5' coding sequence. To obtain the 5' neuroD1 coding sequence, a mouse strain 129/Sv genomic DNA library was screened with the VP16-neuroD plasmid insert (450 bp). Genomic clones were isolated and sequenced and the sequences were aligned with the cDNA sequences. Alignment of the sequence and comparison of the genomic 5' coding sequences with the Xenopus neuroD1 clone (Example 8) confirmed the 5' neuroD1 coding sequence. The complete neuroD1 coding sequence and deduced amino acid sequence are shown in SEQ ID NOS:1 and 2.

EXAMPLE 3

NeuroD/neuroD bHLH proteins share common structural similarities that include a basic region that binds DNA and an HLH region involved in protein-protein interactions required for the formation of homodimers and heterodimeric complexes. A comparison of the amino acid sequence of the basic region of murine neuroD1 (amino acids 102 to 113 of SEQ ID NO:2) with basic regions of other bHLH proteins revealed that murine neuroD1 contained all of the conserved residues characteristic among this family of proteins. However, in addition, neuroD1 contained several unique residues. These unique amino acid residues were not found in any other known HLH, making neuroD1 a distinctive new member of the bHLH family. The NARERNR basic region motif in neuroD1 (amino acids 107-113 of SEQ ID NO:2) is also found in the Drosophila AS-C protein, a protein thought to be involved in neurogenesis. Similar, but not identical, NARERRR and NERERNR motifs (SEQ ID NOS:5 and 6, respectively) have been found in the Drosophila Atonal and MASH (mammalian achaete-scute homolog) proteins, respectively, which are also thought to be involved in neurogenesis. The NARER motif (SEQ ID NO:7) of neuroD1 is shared by other bHLH proteins, and the Drosophila Daughterless (Da) and Mammalian E proteins. The basic region of bHLH proteins is important for DNA binding site recognition, and there is homology between neuroD1 and other neuro-proteins in this functional region. Within the important dimer-determining HLH region of neuroD1, a low level of homology was recorded with mouse twist protein (i.e., 51% homology) and with MASH (i.e., 46% homology). NeuroD1 contains several regions of unique peptide sequence within the bHLH domain including the junction sequence (MHG).

EXAMPLE 4

Tissue expression patterns of neuroD1, neuroD2, and neuroD3

NeuroD1 expression was analyzed during embryonic development of mouse embryos using in situ hybridization. The probe used was an antisense neuroD1 single-stranded riboprobe labeled with digoxigenin (Boehringer Mannheim). Briefly, a riboprobe was prepared from plasmid pSK+1-83 using T7 polymerase and digoxigenin-11-UTP for labeling. The hybridized probe was detected using anti-digoxigenin antibody conjugated with alkaline phosphatase. Color development was carried out according to the manufacturer's instructions. Stages of development are commonly expressed as days following copulation and where formation of the vaginal plug is e0.5. The results recorded in the in situ hybridization studies were as follows:

In the e9.5 mouse embryo, neuroD1 expression was observed in the developing trigeminal ganglia.

In the e10.5 mouse embryo, a distinctive pattern of neuroD1 expression was observed in all the cranial ganglia (i.e., V-XI) and in dorsal root ganglia (DRG) in the trunk region of the embryo. At this time, neuroD1 expression was also observed in the central nervous system in post-mitotic cells in the brain and spinal cord that were undergoing neuronal differentiation. In the spinal cord, the ventral portion of the cord from which the motor neurons arise and differentiate was observed to express neuroD1 at high levels; and expression in the posterior-ventral spinal cord was higher when compared to more mature anterior-ventral spinal cord.

In the e11.5 mouse embryo, the ganglionic expression pattern of neuroD1 observed in e10.5 persisted. Expression in the spinal cord was increased over the level of expression observed in e10.5 embryos, which was consistent with the presence of more differentiating neurons at this stage. At this stage neuroD1 expression was also observed in other sensory organs in which neuronal differentiation occurs, for example, in the nasal epithelium, otic vesicle, and retina of the eye. In both of these organs neuroD1 expression was observed in the region containing differentiating neurons.

In the e14.5 mouse embryo, expression of neuroD1 was observed in cranial ganglia and DRG, but expression of neuroD1 persisted in the neuronal regions of developing sensory organs and the central nervous system (CNS). Thus, neuroD1 expression was observed to be transient during neuronal development.

In summary, expression of neuroD1 in the neurula stage of the embryo (e 10), in the neurogenic derivatives of neural crest cells, the cranial and dorsal root ganglia, and post mitotic cells in the CNS suggests an important possible link between expression and generation of sensory and motor nerves. Expression occurring later in embryonic development in differentiating neurons in the CNS and in sensory organs (i.e., nasal epithelium and retina) also supports a role in development of the CNS and sensory nervous tissue. Since neuroD1 expression was transient, the results suggest that neuroD1 expression is operative as a switch controlling formation of sensory nervous tissue. It is noteworthy that in these studies neuroD1 expression was not observed in embryonic sympathetic and enteric ganglia (also derived from migrating neural crest cells). Overall, the results indicate that neuroD1 plays an important role in neuronal differentiation.

In addition to the in situ studies described above, Northern blot analysis was done to determine in what tissues of the mouse neuroD1, neuroD2, and neuroD3 were expressed. Total RNA was isolated from whole mouse embryos and adult mouse tissues. RNA isolation was performed using RNazol B according to the protocol provided (Cinna/Biotex CS-105B). RNA was size fractionated on 1.5% agarose gels and transferred to Hybond-N membranes. Hybridization was carried out in 7% SDS, 0.25M $Na_2PO_4$, 10 mg/ml BSA, 1 mM EDTA at 65° C. for at least 5 hours and then washed in 0.1×SSC and 0.1% SDS at 55° C.–60° C. Probes for analyzing mouse mRNA were prepared from fragments representing the divergent carboxy-terminal regions 3-prime of the bHLH domain to avoid cross-hybridization between genes. Probe for neuroD1 was made from a 350 base pair PstI fragment from the mouse neuroD1 cDNA (Lee et al., 1995) that encompasses the region coding for amino acids 187-304; probe for neuroD2 was made from a 635 base pair PstI fragment from the mouse neuroD2 cDNA that encompasses the region from amino acid 210 through to the 3-prime non-translated region; and probe for neuroD3 was made from a 400 base pair ApaI-BamHI fragment from the neuroD3 genomic region that is 3-prime to the region coding the bHLH domain.

After labeling with $^{32}P$, the above-described fragments were used to probe Northern blots containing RNAs prepared from various tissues of newborn and adult mice. Both neuroD1 and neuroD2 were detected in the brain of both newborn and adult mice, whereas, neuroD3 transcripts were not detected in any of the tissues tested. RNA extracted from dissected regions of the adult mouse nervous system demonstrated that neuroD1 was more abundant in the cerebellum than the cortex, whereas neuroD2 was expressed at relatively equivalent levels in both cerebellum and cortex.

To determine when during mouse embryonic development neuroD2 and neuroD3 were expressed in comparison to neuroD1, RNA was prepared from whole embryos at various developmental stages. In accord with previous reports (Lee et al., 1995), neuroD1 mRNA was first detected at low levels at embryonic day 9.5 and at increasing levels through embryonic day 12.5, the latest embryonic stage tested. NeuroD2 mRNA was first detected at embryonic day 11 and also increased in abundance through embryonic day 12.5. Although we did not detect neuroD3 in the adult tissues, the embryonic expression pattern showed a transient expression between embryonic day 10 and 12 and then declined to undetectable levels by embryonic day 16. Collectively, these data demonstrate that neuroD3 is expressed transiently during embryogenesis, similar to the expression pattern of MATH1 (Akazawa et al., 1995), and that the temporal expression of neuroD1 and neuroD2 partly overlap with neuroD3, but that their expression persists in the adult nervous system.

EXAMPLE 5

NeuroD1 is expressed in neural and brain tumor cells: murine probes identify human neuroD1

Given the expression pattern in mouse embryo (Example 4), Northern blots of tumor cell line mRNAs were examined using murine neuroD1 cDNA (Example 2) as a molecular probe. As a first step, cell lines that have the potential for developing into neurons were screened. The D283 human medulloblastoma cell line, which expressed many neuronal markers, expressed high levels of neuroD1 by Northern blot analysis. NeuroD1 was also transcribed at various levels by different human neuroblastoma cell lines and in certain rhabdomyosarcoma lines that are capable of converting to neurons.

EXAMPLE 6

Recombinant cells expressing NeuroD1

Recombinant murine 3T3 fibroblast cells expressing either a myc-tagged murine neuroD1 protein or myc-tagged Xenopus neuroD1 protein were made. The recombinant cells were used as a test system for identifying antibody to neuroD described below.

Xenopus neuroD1 protein was tagged with the antigenic marker Myc to allow the determination of the specificity of anti-neuroD1 antibodies to be determined. Plasmid CS2+MT was used to produce the Myc fusion protein. The CS2+MT vector (Turner and Weintraub, ibid.) contains the simian cytomegalovirus IE94 enhancer/promoter (and an SP6 promoter in the 5' untranslated region of the IE94-driven transcript to allow in vitro RNA synthesis) operatively linked to a DNA sequence encoding six copies of the Myc epitope tag (Roth et al, J. Cell Biol. 115:587–596, 1991; which is incorporated herein in its entirety), a polylinker for insertion of coding sequences, and an SV40 late polyadenylation site. CS2-MT was digested with Xho I to linearize the plasmid at the polylinker site downstream of the DNA sequence encoding the Myc tag. The linearized plasmid was blunt-ended using Klenow and dNTPs. A full length Xenopus neuroD1 cDNA clone was digested with Xho I and Eae I and blunt-ended using Klenow and dNTPs, and the 1.245 kb fragment of the Xenopus neuroD1 cDNA was isolated. The neuroD1 fragment and the linearized vector were ligated to form plasmid CS2+MT x1-83.

CS2+MT was digested with Eco RI to linearize the plasmid at the polylinker site downstream of the DNA sequence encoding the Myc tag. The linearized plasmid was blunt-ended using Klenow and dNTPs and digested with Xho I to obtain a linearized plasmid having an Xho I adhesive end and a blunt end. Plasmid pKS+m7a containing a partial murine neuroD1 cDNA was digested with Xho I, and the neuroD1 containing fragment was blunt-ended and digested with Xba I to obtain the approximately 1.6 kb fragment of the murine neuroD1 cDNA. The neuroD1 fragment and the linearized vector were ligated to form plasmid CS2+MT M1-83(m7a).

Plasmids CS2+MT x1-83 and CS2+MT M1-83(m7a) were each transformed into murine 3T3 fibroblast cells and used as a test system for identifying antibody against neuroD1 (Example 7).

EXAMPLE 7

Antibodies to NeuroD1

A recombinant fusion protein of maltose binding protein (MBP) and amino acid residues 70-355 of murine neuroD1 was used as an antigen to evoke antibodies in rabbits. Specificity of the resultant antisera was confirmed by immunostaining of the recombinant 3T3 cells described above. Double-immunostaining of the recombinant cells was observed with monoclonal antibodies to Myc (i.e., the control antigenic tag on the transfected DNA) and with rabbit anti-murine neuroD1 in combination with anti-rabbit IgG. The specificity of the resultant anti-murine neuroD1 sera was investigated further by preparing mouse 3T3 fibroblasts cells transfected with different portions of neuroD1 DNA. Specificity seemed to map to the glutamic acid-rich domain (i.e., amino acids 66-73 of SEQ ID NO:2). The anti-murine antisera did not react with cells transfected with the myc-tagged Xenopus neuroD1. In a similar manner, Xenopus neuroD1 was used to generate rabbit anti-neuroD antisera. The antisera was Xenopus-specific and did not cross react with cells transfected with Myc-tagged murine neuroD1.

EXAMPLE 8

NeuroD1 is a highly evolutionarily conserved protein: sequence of Xenopus neuroD1

Approximately one million clones from a stage 17 Xenopus head cDNA library made by Kintner and Melton (*Development* 99:311, 1987) were screened with the mouse cDNA insert as a probe at low stringency. The hybridization was performed with 50% formamide/4xSSC at 33° C. and washed with 2xSSC/0.1% SDS at 40° C.

Positive clones were identified and sequenced. Analysis of the Xenopus neuroD1 cDNA sequence (SEQ ID NO:3) revealed that neuroD1 is a highly conserved protein between frog and mouse. The deduced amino acid sequences of frog and mouse (SEQ ID NOS:2 and 4) show 96% identity in the bHLH domain (50 of 52 amino acids are identical) and 80% identity in the region that is carboxy-terminal to the bHLH domain (159 of 198 amino acids are identical). The domain structures of murine and Xenopus neuroD1 are highly homologous with an "acidic" N-terminal domain (i.e., glutamic or aspartic acid rich); a basic region; helix 1, loop, helix 2; and a proline rich C-terminal region. Although the amino terminal regions of murine and Xenopus neuroD1 differ in amino acid sequence, both retain a glutamic or aspartic acid rich "acidic domain" (amino acids 102 to 113 of SEQ ID NO:2 and amino acids 56 to 79 of SEQ ID NO:4). It is highly likely that the acidic domain constitutes an "activation" domain for the neuroD1 protein, in a manner analogous to the activation mechanisms currently understood for other known transcription regulatory factors.

EXAMPLE 9

Neuronal expression of Xenopus neuroD1

The expression pattern of neuroD1 in whole mount Xenopus embryos was determined using in situ hybridization with a single stranded digoxigenin-labeled Xenopus neuroD1 antisense cDNA riboprobe. Embryos were examined at several different stages.

Consistent with the mouse expression pattern, by late stage, all cranial ganglia showed very strong staining patterns. In Xenopus, as in other vertebrate organisms, neural crest cells give rise to skeletal components of the head, all ganglia of the peripheral nervous system, and pigment cells. Among these derivatives, the cranial sensory ganglia, which are of mixed crest and placode origin, represent the only group of cells that express neuroD1. High levels of neuroD1 expression in the eye were also observed, correlating with active neuronal differentiation in the retina at this stage. Expression is observed in the developing olfactory placodes and otic vesicles, as was seen in mice. The pineal gland also expressed neuroD1. All of this expression was transient, suggesting that neuroD1 functions during the differentiation process but is not required for maintenance of these differentiated cell types.

As early as stage 14 (i.e., the mid-neurula stage) neuroD1 expression was observed in the cranial neural crest region where trigeminal ganglia differentiate. Primary mechanosensory neurons in the spinal cord, also referred to as Rohon-Beard cells and primary motor neurons, showed neuroD1 expression at this stage.

By stage 24, all of the developing cranial ganglia, trigeminal, facio-acoustic, glosso-pharyngeal, and vagal nervous tissues showed a high level of neuroD1 expression. High levels of expression of neuroD1 were also observed in the eye at this stage. (Note that in Xenopus neuronal differentiation in the retina occurs at a much earlier stage than in mice, and neuroD1 expression was correspondingly earlier and stronger in this animal model.)

In summary, in Xenopus as in mouse, neuroD1 expression was correlated with sites of neuronal differentiation. The remarkable evolutionary conservation of the pattern of neuroD1 expression in differentiating neurons supports the notion that neuroD1 has been evolutionarily conserved both structurally and functionally in these distant classes, which underscores the critical role performed by this protein in embryonic development.

EXAMPLE 10

Expression of neuroD1 and neuroD2 converts non-neuronal cells into neurons

To further analyze the biological functions of neuroD1, a gain-of-function assay was conducted. In this assay, RNA was microinjected into one of the two cells in a 2-cell stage Xenopus embryo, and the effects on later development of neuronal phenotype were evaluated. For these experiments myc-tagged Xenopus neuroD1 transcripts were synthesized in vitro using SP6 RNA polymerase. The myc-tagged-neuroD1 transcripts were microinjected into one of the two cells in a Xenopus 2-cell embryo, and the other cell of the embryo served as an internal control.

Synthesis of capped RNA for the *Xenopus laevis* injections was done essentially as described (Kreig, P. A. and D.

A. Melton., *Meth. Enzymol.* 155:397–415, 1987) using the SP6 transcription of the pCS2-hND2, pCS2-hND1, pCS2-mND2, and pCS2MT-mND2. The capped RNA was phenol/chloroform extracted followed by separation of unincorporated nucleotides using a G-50 spin column. Approximately 350 pg or capped RNA was injected into one cell of 2-cell stage albino *Xenopus laevis* embryo in a volume of approximately 5 nl, as described previously (Turner and Weintraub, 1994). Embryos were allowed to develop in 0.1×modified Barth's saline (MBS) and staged according to Nieuwkoop and Faber (Nieuwkoop, P. D. and J. Faber, "Normal Table of *Xenopus laevis*," North-Holland Publishing Co., Amsterdam, Holland, 1967). Embryos were fixed in MEMFA for 2 hours at room temperature and stored in methanol. Embryos were hydrated through a graded series of methanol/PBS solutions and prepared for immunohistochemistry as described (Turner and Weintraub, 1994). The embryos were stained with an anti-NCAM antibody (Balak et al. *Develop. Biol.* 119:540–550, 1987) diluted 1:500 (gift of Urs Rutishauser) followed by a goat anti-rabbit alkaline phosphatase conjugated secondary antibody, or stained with the monoclonal anti-myc tag 9e10 antibody. Presence of the antibody was visualized by NBT/BCIP color reaction according to protocol provided (Gibco).

Antibodies to Xenopus N-CAM, a neural adhesion molecule, anti-Myc (to detect the exogenous protein tag), and immunostaining techniques were used to evaluate phenotypic expression of the neuronal marker (and control) gene during the subsequent developmental stages of the microinjected embryos. Remarkably, an evaluation of over 130 embryos that were injected with neuroD1 RNA showed a striking increase in ectopic expression of N-CAM on the microinjected side of the embryo (i.e., Myc+), as judged by increased immunostaining. The increased staining was observed in the region from which neural crest cells normally migrate. It is considered likely that ectopic expression (or over-expression) of neuroD1 caused neural crest stem cells to follow a neurogenic cell fate. Outside the neural tube, the ectopic immunostaining was observed in the faciocranial region and epidermal layer, and in some cases the stained cells were in the ventral region of the embryo far from the neural tube. The immunostained cells not only expressed N-CAM ectopically, but displayed a morphological phenotype of neuronal cells. At high magnification, the N-CAM expressing cells exhibited typical neuronal processes reminiscent of axonal processes.

To confirm that the ectopic N-CAM expression resulted from a direct effect on the presumptive epidermal cells and not from aberrant neural cell migration into the lateral and ventral epidermis, neuroD1 RNA was injected into the top tier of 32-cell stage embryos, in order to target the injection into cells destined to become epidermis. N-CAM staining was observed in the lateral and ventral epidermis without any noticeable effect on the endogenous nervous system, indicating that the staining of N-CAM in the epidermis represents the conversion of epidermal cell fate into neuronal cell fate.

Ectopic generation of neurons by neuroD1 was confirmed with other neural specific markers, such as neural-specific class II β-tubulin (Richter et al., *Proc. Natl. Acad. Sci. USA* 85:8066, 1988), acetylated (α-tubulin (Piperno and Fuller, *J. Cell. Biol.* 101:2085, 1985), tanabin (Hemmati-Brinvanlou et al., *Neuron* 9:417, 1992), neurofilament(NF)-M (Szaro et al., *J. Comp. Neurol.* 273:344, 1988), and Xen-1.2 (Ruiz i Altaba, *Development* 115:67, 1992). The embryos were subjected to immunochemistry as described by Turner and Weintraub (*Genes Dev.* 8:1434, 1994, which is incorporated by reference herein) using primary antibodies detected with alkaline phosphatase-conjugated goat anti-mouse or anti-rabbit antibodies diluted to 1:2000 (Boehringer-Mannheim). Anti-acetylated alpha-tubulin was diluted 1:2000. Anti-Xen-1 was diluted 1:1. Anti-NF-M was diluted 1:2000. Embryos stained for NF-M were fixed in Dent's fixative (20% dimethylsulfoxide/80% methanol) and cleared in 2:1 benzyl benzoate/benzyl alcohol as described by Dent et al. (*Development* 105:61, 1989, which is incorporated by reference herein). In situ hybridization of embryos was carried out essentially as described by Harland (in *Methods in Cell Biology*, B. K. Kay, H. J. Pend, eds., Academic Press, New York, N.Y., Vol. 36, pp. 675–685, 1991, which is incorporated by reference herein) as modified by Turner and Weintraub (ibid.). In situ hybridization with β-tubulin without RNase treatment can also detect tubulin expression in the ciliated epidermal cells. All of these markers displayed ectopic staining on the neuroD1 RNA injected side. Injection of neuroD1 mRNA into vegetal cells led to no ectopic expression of neural markers except in one embryo that showed internal N-CAM staining in the trunk region, suggesting the absence of cofactors or the presence of inhibitors in vegetal cells. However, the one embryo that showed ectopic neurons in the internal organ tissue suggests that it may be possible to convert non-ectodermal lineage cells into neurons under certain conditions.

The embryos were also stained with markers that detect Rohon-Beard cells (cells in which neuroD1 is normally expressed). Immunostaining using the method described above for Rohon-Beard cell-specific markers such as HNK-1 (Nordlander, *Dev. Brain Res.* 50:147, 1989, which is incorporated by reference herein) at a dilution of 1:1, Islet-1 (Ericson et al., *Science* 256:1555, 1992 and Korzh et al., *Development* 118:417, 1993) at a dilution of 1:500, and in situ hybridization as described above with shaker-1 (Ribera et al., *J. Neurosci.* 13:4988, 1993) showed more cells staining on the injected side of the embryos.

The combined results support the notion that ectopic expression of neuroD1 induced differentiation of neuronal cells from cells that, without neuroD1 microinjection, would have given rise to non-neuronal cells. In summary, these experiments support the notion that ectopic neuroD1 expression can be used to convert a non-neuronal cell (i.e., uncommitted neural crest cells and epidermal epithelial basal stem cells) into a neuron. These findings offer for the first time the potential for gene therapy to induce neuron formation in injured neural tissues.

Interesting morphological abnormalities were observed in the microinjected embryos. In many cases the eye on the microinjected side of the embryo failed to develop. In other embryos, the spinal cord on the microinjected side of the embryo failed to develop properly, and the tissues were strongly immunopositive when stained with anti-N-CAM. In addition, at the mid-neurula stage many microinjected embryos exhibited an increase in cell mass in the cranial region of the embryo from which (in a normal embryo) the neural crest cells and their derivatives (i.e., cranial ganglionic cells) would migrate. The observed cranial bulge exhibited strong immunostaining with antibodies specific for N-CAM. These results were interpreted to mean that morphological changes in the eye, neural crest, and spinal cord resulted from premature neural differentiation which altered the migration of neural and neural crest precursor cells.

NeuroD1-injected embryos were also assayed for alteration in the expression of Xtwist, the Xenopus homolog of Drosophila twist, to determine whether neuroD1 converted non-neuronal components of neural crest cells into the neural lineage. In wild-type embryos, Xtwist is strongly expressed in the non-neuronal population cephalic neural crest cells that give rise to the connective tissue and skeleton of the head. NeuroD1-injected embryos were completely missing Xtwist expression in the migrating cranial neural crest cells on the injected side. The failure to generate sufficient cranial mesenchymal neural crest precursors in neuroD1-injected embryos was also observed morphologically, since many of the injected embryos exhibited poor branchial arch development in the head. Furthermore, the increased mass of cells in the cephalic region stained very strongly for N-CAM, β-tubulin, and Xen-1, indicating that these cells were neural in character.

The converse experiment in which frog embryos were injected with Xtwist mRNA showed that ectopic expression of Xtwist significantly decreased neuroD1 expression on the injected side. Thus, two members of the bHLH family, neuroD1 and Xtwist, may compete for defining the identity of different cell types derived from the neural crest. In the neuroD1-injected embryos, exogenous neuroD1 may induce premigratory neural crest to differentiate into neurons in situ, and consequently they fail to migrate to their normal positions.

The effect of introduction of exogenous neuroD1 on the fate of cells that normally express neuroD1, such as cranial ganglia, eye, otic vesicle, olfactory organs, and primary neurons, and on other CNS cells that normally do not express neuroD1, was determined by staining for differentiation markers. When the cranial region of the embryo was severely affected by ectopic neuroD1, the injected side of the embryos displayed either small or no eyes in addition to poorly organized brains, otic vesicles, and olfactory organs. Moreover, as the embryos grew, the spinal cord showed retarded growth, remaining thinner and shorter on the neuroD1-injected side.

N-CAM staining in the normal embryo at early stages was not uniform throughout the entire neural plate, but rather was more prominent in the medial region of the neural plate. Injected embryos analyzed for N-CAM expression showed that the neural plate on the injected side of the early stage embryos was stained more intensely and more laterally. The increase in N-CAM staining was not associated with any lateral expansion of the neural plate as assayed by visual inspection and staining with the epidermal marker EpA. This was in contrast to what has been observed with XASH-3 injection that causes neural plate expansion. These observations suggest that the first effects of neuroD1 are to cause neuronal precursors in the neural plate to differentiate prematurely.

To determine whether neuroD1 caused neuronal precursors to differentiate prematurely, injected embryos were stained using two neuronal markers that are expressed in differentiated neurons, neural specific β-tubulin and tanabin. In situ hybridization for β-tubulin and tanabin was carried out as described above. Over-expression of neuroD1 dramatically increased the β-tubulin signals in the region of the neural plate containing both motor neurons and Rohon-Beard cells at stage 14. The earliest ectopic β-tubulin positive cells on the injected side were observed at the end of gastrulation when the control side did not yet show any β-tubulin positive cells. Tanabin was also expressed in more cells in the spinal cord in the neuroD1 injected side of the embryos at stage 14. These results suggest that neuroD1 can cause premature differentiation of the neural precursors into differentiated neurons. This is a powerful indication that, when ectopically expressed or over-expressed, neuroD1 can differentiate mitotic cells into non-dividing mature neurons.

To determine if neuroD2 also was capable of inducing ectopic neuronal development in the frog, mouse neuroD2 RNA was injected into one side of a two cell *X. laevis* embryo, the uninjected side serving as a control. The neuroD2 mRNA was made from pCS2-MTmND2, an expression vector that was constructed as follows. Expression vectors were made in the pCS2+ or pCS2+MT (Turner, D. L. and H. Weintraub, *Genes & Dev.* 8:1434–1447, 1994), both contain the simian CMV promoter and the MT contains six copies of the myc epitope recognized by the 9e10 monoclonal antibody (ATCC:CRL 1729) cloned in-frame upstream of the insert. The 1.75 kb full length human neuroD1 cDNA (Tamimi et al., *Genomics* 34:418–421, 1996) from plasmid phcnd1-17a was cloned into the EcoRI site to make pCS2-hND1-17s (hereafter referred to as pCS2-hND1). The 1.53 kb genomic region containing the entire coding sequence of the human neuroD2 gene (described in Example 11) was cloned into the StuI-XbaI site to make pCS2-hND2-14B1 (hereafter referred to as pCS2-hND2). The mouse 1.95 kb neuroD2 cDNA was cloned into the EcoRI-XhoI sites to make pCS2-mND2-1.1.1 (hereafter referred to as pCS2-mND2). For the myc-tagged construct, a synthetic oligonucleotide mediated mutagenesis was used to introduce an EcoRI site adjacent to the initial ATG codon to result in the myc-tag and neuroD2 coding regions being in-frame to make pCS2MT-mND2.

When injected into *Xenopus laevis*, mouse neuroD2 mRNA was able to induce ectopic neuronal development as determined by immunohistochemistry with an anti-NCAM antibody. An anti-myc tag antibody, 9E10, was used to confirm that most ectodermal cells on the injected side of the frog expressed the myc-tagged mouse neuroD2 and approximately 80–90% of injected embryos stained positively with either the anti-myc or anti-NCAM antibodies. Injection of RNA encoding the human neuroD2 gene resulted in an ectopic neuronal phenotype similar to that seen with Xenopus neuroD1 and murine neuroD2. This demonstrates that both neuroD1 and neuroD2 can regulate the formation of neurons and that the human and mouse neuroD2 proteins are capable of functioning in the developing Xenopus embryo.

Developmental expression patterns suggest two distinct sub-families of neurogenic bHLH genes. MATH1 and neuroD3 share similarity in the bHLH region and have similar temporal expression patterns, with RNA expression detected around embryonic day 10, but not persisting in the mature nervous system. MATH-1 RNA was localized to the dorsal neural tube in 10.5–11.5 day embryos, but by birth was present only in the external granule cell layer of the cerebellum, the progenitors of the cerebellar granule cell layer (Akazawa et al., 1995). In contrast, the neuroD1, neuroD2, and MATH2/NEX-1 genes are expressed in both differentiating and mature neurons. Northern analysis demonstrated that neuroD2 expression begins around embryonic day 11 and continues through day 16, the latest embryonic time point tested. NeuroD2 was detected in the brain of neonates as well as adult mice, with relatively equal abundance in both the cerebellum and cortex. Similar to neuroD2, the CNS expression of neuroD1 persists postnatally, as well as does its expression in the beta cells of the pancreas (Naya et al., 1995). Northern blot analysis indicated that neuroD1 expression in the adult mouse brain is most abundant in the cerebellum with lower levels in the cerebral cortex and brain stem. NEX-1/MATH-2 gene expression is reported to occur by embryonic day 11.5 and at embryonic day 15.5 its expression is limited to the intermediate zone adjacent to the mitotically active ventricular zone, suggesting that NEX-1/MATH2 is expressed primarily in the newly differentiating neurons at this stage (Bartholoma and Nave, 1994; Shimizu et al., 1995). In mature brain, NEX-1/MATH-2 is expressed in neurons comprising the hippocampus, subsets of cortical neurons, and post migratory cerebellar granule cells, but the reports disagree on whether this gene is expressed in the dentate gyrus of the hippocampus. It is interesting to note that the Northern analysis of MATH2 expression reported by Shimizu et al. (1995) shows high levels in the cerebral cortex and low levels in the cerebellum, the opposite of the expression pattern seen for neuroD1, suggesting that these genes may also have significant differences in relative abundance in specific regions of the nervous system. Therefore, it appears that MATH-1 and neuroD3 are expressed early in nervous system development and may have a role in either determining or expanding a population of neuronal precursors, whereas the persistent expression of neuroD1, neuroD2 and NEX-1/MATH-2 suggest a role in initiating and maintaining expression of genes related to neuronal differentiation.

Kume et al. (*Biochem. Biophys. Res. Comm.* 219:526–530, 1996) have reported the cloning of a helix-loop-helix gene from rat brain using a strategy designed to identify genes that are expressed during tetanic stimulation of hippocampal neurons in a model of long-term-potentiation. The gene they describe, KW8, is the rat homolog of the mouse and human neuroD2 gene described here. Kume et al. also describe expression in the adult brain, including the hippocampus. Subsequently, Yasunami et al. (*Biophys. Res. Comm.* 220:754–758, 1996) reported the mouse NDRF gene, which is nearly identical to neuroD2 and demonstrates a similar expression pattern in adult brain by in situ hybridization.

While expression of either neuroD1 or neuroD2 in *Xenopus leavis* embryos resulted in ectopic neuronal development, it is interesting to note that neither neuroD1 nor neuroD2 was capable of converting all cell types in which it was present into neurons. As in the case of neuroD1, the ectopic neurons induced by neuroD2 were confined to a subpopulation of ectodermal cells, as indicated by the spotty NCAM positive staining pattern. The apparent restricted activity of the neuroD proteins to a subset of cells derived from the ectoderm suggests that other factors may regulate their activity, such as the notch pathway that mediates lateral inhibition during *Drosophila neurogenesis*.

While the induction of ectopic neurogenesis by both neuroD1 and neuroD2 in Xenopus embryos suggests a similar function, the developmental expression patterns and in vitro transfection experiments indicate that the family members may serve both overlapping and distinct functions. Previous studies have demonstrated that neuroD/beta2 and NEX-1/MATH2 can bind the core CANNTG sequence of an E-box as a heterodimer with an E-protein and activate transcription.

In the work presented here, it is shown that both neuroD1 and neuroD2 can activate a construct containing multimerized E-boxes. They also activate a construct driven by a genomic fragment from the neuroD2 gene that presumably contains regulatory regions for neuroD2, and the temporal expression pattern of neuroD1 and neuroD2 proteins in embryogenesis and P19 differentiation suggests a model in which neuroD1 may activate neuroD2 expression during development. Most important, however, is the demonstration that neuroD1 and neuroD2 have different capacities to activate a construct driven by the core regulatory sequences of the GAP-43 gene, demonstrating that the highly related neuroD1 and neuroD2 proteins are capable of regulating specific subsets of genes. This promoter contains several E-boxes and it remains to be determined if neuroD2 directly binds to these sites.

In the bHLH region, neuroD1 and neuroD2 differ by only 2 amino acids and it would be anticipated that they recognize the same core binding sequences. Therefore, the differential regulation of transcriptional activity may be determined independently of DNA binding. The amino acid following the histidine in the junction region of the basic region is a glycine in neuroD1, NEX-1/MATH2, and MATH1, an aspartate in neuroD2, and an asparagine in neuroD3. This residue is positioned at the same site as the lysine residue in the myogenic bHLH proteins that has been shown to be one of the critical for myogenic activity (Davis et al., *Cell* 60:733–746, 1990; Davis, R. L. and H. Weintraub, *Science* 256:1027–1030, 1992; Weintraub et al., *Genes & Dev.* 5:1377–1386, 1991). In this case, it has been postulated to be a site of potential interaction with co-activator factors that regulate transcriptional activity. If the neuroD proteins have a similar mechanism for exerting their regulatory activities, it is possible that amino acid variability in this amino acid mediates different target specificities. Alternatively, the more divergent amino- and carboxyterminal regions could confer regulation by interaction with other activators or repressors.

The different expression patterns in the mature nervous system and the subtle differences in target genes is similar to myogenic bHLH proteins. In mature muscle, MyoD is expressed in fast muscle fibers and myogenin in slow fibers (Asakura et al., *Develop. Biol.* 171:386–398, 1995; Hughes et al., *Development* 118:1137–1147, 1993) and transfection studies demonstrate that sequences adjacent to the core E-box sequence can differentially regulate the ability of MyoD and myogenin to function as transcriptional activators (Asakura et al., *Molec. & Cell. Biol.* 13:7153–7162, 1993), presumably by interaction of other regulatory factors with the non-bHLH regions of MyoD and myogenin. For the neuroD-related genes, the partially overlapping expression patterns and partially overlapping target genes suggest that they may act in a combinatorial fashion to directly regulate overlapping subsets of genes and thereby confer specific neuronal phenotypes. In this model, it is possible that a small family of neuroD-related transcription factors acts to establish the identity of a limited number of neuronal sub-types and that local inductive events influence the generation of a higher complexity. Alternatively, it is possible that many additional members of this sub-family are yet to be identified and they may act to directly determine specific neuronal attributes.

EXAMPLE 11

Genomic clones of human neuroD1, neuroD2 and neuroD3 and mouse neuroD3

Genomic clones encoding human neuroD1 were obtained by probing a human fibroblast genomic library with the mouse neuroD1 cDNA. Host *E. coli* strain LE392 (New England Biolabs) were grown in LB+10 mM $MgSO_4$, 0.2% maltose overnight at 37° C. The cells were harvested and resuspended in 10 mM $MgSO_4$ to a final OD600 of 2. The resuspended cells were used as hosts for phage infection. The optimal volume of phage stock for use in this screening was determined by using serial dilutions of the phage stock of a human fibroblast genomic library in lambda FIX II (STRATAGENE) to infect LE392 cells (New England Biolabs). To obtain approximately 50,000 plaques per plate, a 2.5 µl aliquot of the phage stock was used to infect 600 µl of the resuspended LE392 cells. The cells were incubated with the phage for 15 minutes at 37° C., after which the cells were mixed with 6.5 ml of top agar warmed to 50° C. The top agar was plated on solid LB, and incubated overnight at 37° C. A total of 22 15-cm plates were prepared in this manner.

Duplicate plaque lifts were prepared. A first set of HYBOND membranes (Amersham) were placed onto the plates and allowed to sit for 2 minutes. The initial membranes were removed and the duplicate membranes were laid on the plates for 4 minutes. The membranes were allowed to air dry; then the phage were denatured in 0.5M NaOH, 1.5M NaCl for 7 minutes. The membranes were neutralized with two washes in neutralization buffer (1.5M NaCl, 0.5M Tris, pH 7.2). After neutralization, the membranes were crosslinked by exposure to UV. A 1 kb Eco RI-Hind III fragment containing murine neuroD1 coding sequences was random primed using the Random Priming Kit (Boehringer Mannheim) according to the manufacturer's instructions. Membranes were prepared for hybridization by placing six membranes in 10 ml of FBI hybridization buffer (100 g polyethylene glycol 800, 350 ml 20% SDS, 75 ml 20×SSPE; add water to a final volume of one liter) and incubating the membranes at 65° C. for 10 minutes. After 10 minutes, denatured salmon sperm DNA was added to a final concentration of 10 µg/ml and denatured probe was added to a final concentration of 0.25–0.5×10$^7$ cpm/ml. The membranes were hybridized at 65° C. for a period of 8 hours to overnight. After incubation, the excess probe was removed, and the membranes were washed first in 2×SSC, 0.1% SDS for 30 minutes at 50° C. The first wash was followed by a final wash in 0.1×SSC, 0.1% SDS for 30 minutes at 55° C. (moderate stringency). Autoradiographs of the membranes were prepared. The first screen identified 55 putative positive plaques. Thirty-one of the plaques were subjected to a secondary screen using the method essentially set forth above. Ten positive clones were identified and subjected to a tertiary screen as described above. Eight positive clones were identified after the tertiary screen. Of these eight clones, three (14B1, 9F1 and 20A1) were chosen for further analysis. Clones 14B1 and 20A1 were deposited at the American Type Culture Collection, 12301 Parklawn Drive, Rockville, Md. 20852 USA, on Nov. 1, 1995, under accession numbers 69943 and 69942, respectively.

Phage DNA was prepared from clones 14B1, 9F1, and 20A 1. The 14B1 and 20A1 phage DNA were digested with Pst I to isolate the 1.2 kb and 1.6 kb fragments, respectively, that hybridized to the mouse neuroD1 probe. The 9F1 phage DNA was digested with Eco RI and SacI to obtain an approximately 2.2 kb fragment that hybridizes with the mouse neuroD1 probe. The fragments were each subcloned into plasmid BLUESCRIPT SK (STRATAGENE) that had been linearized with the appropriate restriction enzyme(s). The fragments were sequenced using SEQUENASE Version 2.0 (US Biochemical) and the following primers: the universal primer M13-21, the T7 primer, and the T3 primer.

Sequence analysis of clones 9F1 (SEQ ID NOS:8 and 9), and 14B1 (SEQ ID NOS:10 and 11) showed a high similarity between the mouse and human coding sequences at both the amino acid and nucleotide level. In addition, while clones 9F1 and 14B1 shared 100% identity in the HLH region at the amino acid level (i.e., residues 117-156 in SEQ ID NO:9 and residues 137-176 in SEQ ID NO:11), they diverged in the amino-terminal of the bHLH. This finding strongly suggests that 14B1 is a member of the neuroD family of genes. Sequence analysis demonstrates that clone 9F1 has a high degree of homology throughout the sequence region that spans the translation start site to the end of the bHLH region. The 9F1 clone has 100% identity to mouse neuroD1 in the HLH region (i.e., residues 117–156 in SEQ ID NO:9 and residues 117–156 in SEQ ID NO:2), and an overall identity of 94%. The 14B1 clone also has 100% identity to the HLH region (i.e., residues 137-176 in SEQ ID NO:11 and residues 117–156 in SEQ ID NO:2), but only 40% identity to 9F1 and 39% identity to mouse neuroD1 in the amino-terminal region. This demonstrates that 9F1 is the human homolog of mouse neuroD1, whereas the strong conservation of the neuroD HLH identifies 14B1 as another member of the neuroD HLH subfamily. Human clone 9F$_1$ (represented by SEQ ID NOS: 8 and 9) is referred to as human neuroD1. Human clone 14B1 is referred to as neuroD2 (SEQ ID NOS:10 and 11, and human clone 20A1 is referred to as neuroD3 (SEQ ID NOS:12 and 13).

A fragment of the human neuroD2 gene was used to screen both a mouse genomic library and an embryonic day 16 mouse cDNA library. An 800 bp Hind III-Eag I fragment from the neuroD2 sequences from clone 14B1 was random primed with $^{32}$P, and used to screen a 16-day mouse embryo cDNA library essentially as described previously. Filters were prehybridized in FBI hybridization buffer (see above) at 50° C. for 10 minutes. After prehybridization, denatured salmon sperm DNA was added to a final concentration of 10 µg/ml; denatured probe was added to a final concentration of one million cpm/ml. The filters were hybridized at 50° C. overnight. After incubation, excess probe was removed, and the filters was washed first in 2×SSC, 0.1% SDS for 30 minutes at 60° C. Genome clones were obtained and characterized. Five independent cDNAs were mapped by restriction endonucleases and demonstrated identical restriction sites and sequence. One clone, designated 1.1.1, contained 1.46 kb of murine neuroD2 cDNA as an Eco RI-Hind III insert. The nucleotide sequence and deduced amino acid sequences are shown in SEQ ID NOS:16 and 17, respectively. A comparison with the corresponding mouse genomic sequence demonstrated that the entire coding region of neuroD2 is contained in the second exon.

The mouse neuroD2 cDNA sequence indicated a predicted protein of 382 amino acids that differs from the major open reading frame in the human neuroD2 gene at only 9 residues, all in the aminoterminal portion of the protein. The human neuroD2 protein was found to have 98% similarity to neuroD1 and MATH2 in the bHLH region and 90% similarity in the 30 amino acids immediately carboxyterminal to the bHLH region. Similar to neuroD1 and MATH2, neuroD2 contains an aminoterminal region rich in glutamate residues that may constitute an acidic activation domain, and has other regions of similarity to neuroD1 throughout the protein.

Mouse neuroD3 was obtained by screening a 129SV mouse genomic library cloned in lambda-Dash II (STRATAGENE), using a labeled Pst-Pst genomic fragment containing the human neuroD coding sequence using conditions essentially as described above for selecting mouse neuroD2, with the exception that the prehybridization and hybridization were carried out at 55° C. and the final wash was carried out at 50° C.

Since all identified members of the family of genes related to neuroD1 are known to have their entire coding sequence in a single exon, the major open reading frame (ORF) encoded in the genomic DNA from human and mouse neuroD3 were determined (SEQ ID NO:12 and SEQ ID NO:21, respectively). The predicted amino acid sequences of the mouse and human neuroD3 proteins are based on the major ORF in the corresponding genomic DNAs, since cDNAs have not been cloned for these genes. The genomic sequence of mouse neuroD3 contains a major ORF of 244 amino acids and the human neuroD3 gene an ORF of 237 amino acids that differs from the predicted mouse protein at 26 positions. The entire coding region of other neuroD family members is contained within a single exon, and therefore it is possible that the ORF in the neuroD3 genomic DNA represents the entire coding region, a notion supported by the conservation between mouse and human that extends to the stop codon. The major ORF predicts a smaller protein than related neuroD family members, and lacks the acidic rich aminoterminal region. The bHLH region has some elements of the loop that are similar to MATH1, but the overall level of homology in the bHLH region is closer to the neuroD-related genes. In contrast to neuroD2, the neuroD3 protein does not contain significant regions of homology to neuroD1 or MATH2/NEX-1 outside of the bHLH region and does not have an aminoterminal region rich in glutamates or acidic amino acids.

The Genbank accession numbers are: human neuroD2, U58681; mouse neuroD2, U58471; human neuroD3, U63842; mouse neuroD3, U63841.

EXAMPLE 12

Chromosome mapping of human neuroD1 clones

FISH karyotyping was performed on fixed metaphase spreads of the microcell hybrids essentially as described (Trask et al., *Am. J. Hum. Genet.* 48:1–15, 1991; and Brandriff et al., *Genomics* 10:75–82, 1991; which are incorporated by reference herein in their entirety). NeuroD1 sequences were detected using the 9F1 or 20A1 phage DNA as probes labeled using digoxigenin-dUTP (Boehringer Mannheim) according to the manufacturer's instructions. Phage DNA was biotinylated by random priming (Gibco/BRL BioNick Kit) and hybridized in situ to denatured metaphase chromosome spreads for 24–48 hours. Probes were detected with rhodamine-conjugated antibodies to digoxigenin, and chromosomes were counterstained with DAPI (Sigma). Signals were viewed through a fluorescence microscope and photographs were taken with color slide film. FISH analysis indicated clone 9F1 maps to human chromosome 2q, and clone 20A1 maps to human chromosome 5.

Chromosome mapping was also carried out on a human/rodent somatic cell hybrid panel (National Institute of General Medical Sciences, Camden, N.J.). This panel consists of DNA isolated from 24 human/rodent somatic cell hybrids retaining one human chromosome. For one set of experiments, the panel of DNAs were digested with Eco RI and electrophoresed on an agarose gel. The DNA was transferred to Hybond-N membranes (Amersham). A random primed (Boehringer Mannheim) 4 kb Eco RI-Sac I fragment of clone 9F1 was prepared. The filter was prehybridized in 10 ml of FBI hybridization buffer (see above) at 65° C. for 10 minutes. After prehybridization, denatured salmon sperm DNA was added to a final concentration of 10 µg/ml; denatured probe was added to a final concentration of one million cpm/ml. The filter was hybridized at 65° C. for a period of 8 hours to overnight. After incubation, excess probe was removed, and the filter was washed first in 2×SSC, 0.1% SDS for 30 minutes at 65° C. The first wash was followed by a final stringent wash in 0.1×SSC, 0.1% SDS for 30 minutes at 65° C. An autoradiograph of the filter was prepared. Autoradiographs confirmed the FISH mapping results.

In the second experiment, the panel was digested with Pst I, electrophoresed and transferred essentially as described above. A random-primed (Boehringer Mannheim) 1.6 kb Pst I fragment of clone 20A1 was prepared. The membrane was prehybridized, hybridized with the 20A1 probe and washed as described above. Autoradiographs of the Southern filter showed that 20A1 mapped to human chromosome 5 and confirmed the FISH mapping results. After autoradiography, the 20A1-probed membrane was stripped by a wash in 0.5M NaOH, 1.5M NaCl. The membrane was neutralized in 0.5M Tris-HCl (pH 7.4), 1.5M NaCl. The filter was washed in 0.1×SSC before prehybridization. A random-primed (Boehringer Mannheim) 1.2 kb Pst I fragment of clone 14B1 was prepared. The washed membrane was prehybridized and hybridized with the 14B1 probe as described above. After washing under the previously described conditions, the membrane was autoradiographed. Autoradiographs demonstrated that clone 14B1 mapped to chromosome 17.

EXAMPLE 13

Human neuroD1 complementary DNA

To obtain a human neuroD1 cDNA, one million plaque forming units (pfu) were plated onto twenty LB+10 mM $MgSO_4$ (150 mm) plates using the Stratagene human cDNA library in Lambda ZAP II in the bacterial strain XL-1 Blue (Stratagene). Plating and membrane lifts were performed using standard methods, as described in Example 11. After UV cross-linking, the membranes were pre-hybridized in an aqueous hybridization solution (1% bovine serum albumin, 1 mM EDTA, 0.5M $Na_2HPO_4$ (pH 7.4), 7% SDS) at 50° C. for two hours.

The mouse neuroD1 cDNA insert was prepared by digesting the pKS+m7a RX plasmid with Eco RI and Xho I, and isolating the fragment containing the cDNA by electroelution. A probe was made with the cDNA containing fragment by random primed synthesis with random hexanucleotides, dGTP, dATP, dTTP, alpha-$^{32}$P-labeled dCTP, and Klenow in a buffered solution (25 mM Tris (pH6.9), 50 mM KCl, 5 mM $MgCl_2$, 1 mM DTT). The probe was purified from the unincorporated nucleotides on a G-50 SEPHAROSE column. The purified probe was heat denatured at 90° C. for three minutes.

After prehybridization, the denatured probe was added to the membranes in hybridization solution. The membranes were hybridized for 24 hours at 50° C. Excess probe was removed from the membranes, and the membranes were washed in 0.1×SSC, 0.1% SDS for 20 minutes at 50° C. The wash solution was changed five times. The membranes were blotted dry and covered with plastic film before being subjected to autoradiography. Autoradiography of the filters identified 68 positive clones. The clones were plaque-purified and rescreened to obtain 40 pure, positive clones. The positive clones were screened with a random-primed Pst I fragment from clone 9F1 (human neuroD1). Twelve positive clones that hybridized with the human neuroD1 genomic probe were isolated.

The plasmid vector containing cDNA insert was excised in vivo from the lambda phage clone according to the STRATAGENE methodology. Briefly, eluted phage and XL-1 Blue cells (200 microliters of OD 600=1) were mixed with R408 helper phage provided by Stratagene for 15 minutes at 37° C. Five milliliters of rich bacterial growth media (2×YT, see Sambrook et al., ibid.) was added, and the cultures were incubated for 3 hours at 37° C. The tubes were heated at 70° C. for 20 minutes and spun for 5 minutes at 4,000×g. After centrifugation, 200 microliters of supernatant were added to the same volume of XL-1 Blue cells (OD=1), and the mixture was incubated for 15 minutes at 37° C., after which the bacterial cells were plated onto LB plates containing 50 mg/ml ampicillin. Each colony was picked and grown for sequencing template preparation. The clones were sequenced and compared to the human genomic sequence. A full length cDNA encoding human neuroD1 that was identical to the 9F1 neuroD1 genomic sequence was obtained and designated HC2A. The nucleotide and deduced amino acid sequences are shown in SEQ ID NOS:14 and 15, respectively. Clone HC2A was deposited at the American Type Culture Collection, 12301 Parklawn Drive, Rockville, Md. 20852 USA, on Nov. 1, 1995, under accession number 69944.

Using a random-primed radiolabeled antisense probe to the mouse neuroD2 (Boehringer Mannheim), the expression pattern was determined using Northern analysis. Filters containing murine RNA from the brain and spinal cords of embryonic through adult mice were probed at high stringency and washed in 0.1×SSC, 0.1% SDS at 65° C. Northern analysis showed neuroD2 expression in the brain and spinal cords of mice from embryonic day 12.5 through adult.

Experiments were conducted also to isolate a cDNA corresponding to mouse neuroD3 mRNA. Using procedures similar to those described above, a random-primed 1.1 kb Pst I fragment from human neuroD3 clone 20A1 was prepared and used to screen mouse embryo and newborn mouse brain libraries. For unknown reasons, no positive clones were obtained. Likewise, attempts to clone human neuroD3 cDNA have been unsuccessful. The difficulty in obtaining neuroD3 cDNA may be secondary to instability of the construct in the library, since deletions in the genomic DNA were common during amplification.

EXAMPLE 14

Construction of knock-out mice

Knock-out mice in which the murine neuroD1 coding sequence was replaced with the β-galactosidase gene and the neomycin resistance gene (neo) were generated i) to assess the consequences of eliminating the murine neuroD1 protein during mouse development and ii) to permit examination of the expression pattern of neuroD1 in embryonic mice. Genomic neuroD1 sequences used for these knock-out mice were obtained from the 129/Sv mice so that the homologous recombination could take place in a congenic background in 129/Sv mouse embryonic stem cells. Several murine neuroD1 genomic clones were isolated from a genomic library prepared from 129/Sv mice (Zhuang et al., *Cell* 79:875–884, 1994; which is incorporated herein by reference in its entirety) using the Bam HI-Not I neuroD1 cDNA containing fragment of pSK+1-83 (Example 2) as a random-primed probe essentially as described in Example 11. Plasmid pPNT (Tybulewicz et al., *Cell* 65:1153–1163, 1991; which is incorporated herein by reference in its entirety) containing the neomycin resistance gene (neo; a positive selection marker) and the *Herpes simplex* virus thymidine kinase gene (hsv-tk; a negative selection marker) under the control of the PGK promoter provided the vector backbone for the targeting construct. A 1.4 kb 5' murine neuroD1 genomic 3 kb cytoplasmic β-galactosidase gene were inserted between the Eco RI and Xba I sites of the pPNT vector, and an 8 kb fragment containing the genomic 3' untranslated sequence of neuroD1 was inserted into the vector backbone between into the Xho I and Not I sites.

To prepare an Eco RI-Xba I fragment containing neuroD1 promoter sequences joined to the β-galactosidase gene, a 1.4 kb Eco RI(vector-derived)-Asp 718 fragment containing the 5' untranslated murine neuroD1 genomic sequence was ligated to a Hind III-Xba I fragment containing the cytoplasmic β-galactosidase gene such that the Asp 718 and Hind III sites were destroyed. The resulting approximately 4.4 kb Eco RI-Xba I fragment, containing the 5' neuroD1 genomic sequence (including the neuroD1 promoter) and the β-galactosidase gene in the same transcriptional orientation, was inserted into Eco RI-Xba I linearized pPNT to yield the plasmid pPNT/5'+β-gal. A neuroD1 fragment containing 3' untranslated DNA was obtained from a murine neuroD1 genomic clone that had been digested with Spe I and Not I(vector-derived) to yield an 8 kb fragment. To obtain a 5'Xho I site, the 8 kb fragment was inserted into Spe I-Not I linearized pBlueskriptSK+(Stratagene), and the resulting plasmid digested with Xho I and Not I to obtain the 8 kb neuroD1 3' genomic fragment. The Xho I-Not I fragment was inserted into Xho I-Not I linearized pPNT/5'+β-gal to yield the neuroD1 targeting vector. The final construct contained the 5'neuroD1 fragment, the β-galactosidase gene, and the 3' genomic neuroD1 fragment in the same orientation, and the hsv-tk and neomycin resistance genes in the opposite orientation.

The targeting construct was transfected by electroporation into mouse embryonic stem (ES) cells. A 129/Sv derived ES cell line, AK-7 described by Zhuang et al. (ibid.) was used for electroporation. These ES cells were routinely cultured on mitomycin C-treated (Sigma) SNL 76/7 cells (feeder cells) as described by McMahon and Bradley (Cell 62:1073–1085, 1990; which is incorporated herein by reference in its entirety) in culture medium containing high glucose DMEM supplemented with 15% fetal bovine serum (Hyclone) and 0.1 µM β-mercaptoethanol. To prepare the targeting construct for transfection, 25 µg of the targeting construct was linearized by digestion with Not I, phenol-chloroform extracted, and ethanol precipitated. The linearized vector was then electroporated into 1–2×10$^7$ AK-7 (ES) cells. The electroporated cells were seeded onto three 10 cm plates, with one plate receiving 50% of the electroporated cells and the remaining two plates each receiving 25% of the electroporated cells. After 24 hours, G418 was added to each of the plates to a final concentration of 150 µg/ml . After an additional 24 hours, gancyclovir was added to a final concentration of 0.2 µM to the 50% plate and one of the 25% plates. The third plate containing 25% of the electroporated cells was subjected to only G418 selection to assess the efficiency of gancyclovir selection. The culture medium for each plate was changed every day for the first few days, and then changed as needed after selection had occurred. After 10 days of selection, a portion of each colony was picked microscopically with a drawn micropipette, and was directly analyzed by PCR as described by Joyner, et al. (*Nature* 338:153–156, 1989; which is incorporated herein by reference in its entirety). Briefly, PCR amplification was performed as described (Kogan et al., *New England J. Med.* 317:985–990, 1987; which is incorporated herein by reference in its entirety) using 40 cycles of 93° C. for 30 seconds, 57° C. for 30 seconds, and 65° C. for 3 minutes. To detect the wild-type allele, primers JL34 and JL36 (SEQ ID NOS:18 and 19, respectively) were used in the PCR reaction, to detect the mutant neuroD1 allele, primers JL34 and JL40 (SEQ ID NOS:18 and 20, respectively) were used in the PCR reaction. Positive colonies, identified by PCR, were subcloned into 4-well plates, expanded into 60 mm plates and frozen into 2–3 ampules.

Among the clones that were selected for both G418-resistance (positive selection for neo gene expression) and gancyclovir-resistance (negative selection for hsv-tk gene expression). 10% of the population contained correctly targeted integration of the vector into the murine neuroD1 locus (an overall 10% targeting frequency). The negative selection provided 4–8 fold enrichment for homologous recombination events.

To generate chimeric mice, each positive clone was thawed and passaged once on feeder cells. The transfected cells were trypsinized into single cells, and blastocysts obtained from C57BL/6J mice were injected with approximately 15 cells. The injected blastocysts were then implanted into pseudopregnant mice (C57BL/6J x CBA). Four male chimeras arose from the injected blastocysts (AK-71, AK-72, AK-74 and AK-75). The male chimeras AK-71 and AK-72 gave germ-line transmission at a high rate as determined by the frequency of agouti coat color transmission to their offspring (F1) in a cross with C57BL/6J female mice. Since 50% of the agouti coat color offspring (F1) should represent heterozygous mutants, their genotypes were determined by Southern blot analysis. Briefly, genomic DNA prepared from tail biopsies was digested with Eco RI and probed with the 1.4 kb 5' genomic sequence used to make the targeting construct. This probe detects a 4 kb Eco RI fragment from the wild-type allele and a 6.3 kb Eco RI fragment from the mutant allele. Therefore, a Southern analysis would show a single 4 kb band for a wild-type mouse, 4 kb and 6.3 kb fragments for a heterozygous mouse, and a single 6.3 kb band for a homozygous mutant mouse. The resulting offspring (F1) heterozygous (±) mice, were mated with sibling heterozygous mice to give rise to the homozygous (−/−) mutant mice.

To study neuroD1 expression patterns in embryonic mice, chimeric mice or F1 heterozygous progeny from the chimera x C57B/6J mating were crossed with C57B/6J. Litters resulting from these crosses were harvested from pregnant females and stained for β-galactosidase activity. The embryos were dissected away from all the extra-embryonic tissue and the yolk sac was reserved for DNA analysis. The embryos were fixed for one hour in a fixing solution (0.1M phosphate buffer containing 0.2% glutaraldehyde, 2% formaldehyde, 5 mM EGTA (pH 7.3), 2 mM $MgCl_2$). The fixing solution was removed by three thirty-minute rinses with rinse solution (0.1M phosphate buffer (pH 7.3) containing 2 mM $MgCl_2$, 0.1% sodium deoxycholate, 0.2% NP-40). The fixed embryos were stained overnight in the dark in rinse solution containing 1 mg/ml X-gal, 5 mM sodium ferricyanide, 5 mM sodium ferrocyanide. After staining, the embryos were rinsed with PBS and stored in the fixing solution before preparation for examination. Examination of stained tissue from fetal and postnatal mice heterozygous for the mutation confirmed the neuroD1 expression pattern in neuronal cells demonstrated previously by in situ hybridization (Example 4), and also demonstrated neuroD1 expression in the pancreas and gastrointestinal tract.

Blood glucose levels were detected using PRECISION QID blood glucose test strips and a PRECISION QID blood glucose sensor (Medisens Inc., Waltham, Mass.) according to the manufacturer's instruction. A tissue sample was taken for DNA analysis and the pups were fixed for further histological examination. Blood glucose levels in mice homozygous for the mutation (neuroD1) had blood glucose levels between 2 and 3 times higher than the blood glucose level of wild-type mice. Heterozygous mutants exhibited similar blood glucose levels as wild-type mice. Mice that were homozygous for the mutation (lacking neuroD1) had diabetes as demonstrated by high blood glucose levels and died by day four; some homozygous mice died at birth.

EXAMPLE 15

NeuroD1 expression and activity in PC12 and P19 embryonic carcinoma cells

Murine PC12 pheochromacytoma cells differentiate into neurons in tissue culture in the presence of appropriate inducers, i.e., nerve growth factor. Neither induced nor non-induced murine PC12 cells expressed neuroD1 transcripts, nor did control 3T3 fibroblasts produce detectable levels of neuroD1 transcription products.

P19 cells are a well characterized mouse embryonic carcinoma cell line with the ability to differentiate into numerous cell types, including skeletal and cardiac muscle, or neurons and glia following treatment with dimethylsulfoxide (DMSO) or retinoic acid (RA) (Jones-Villeneuve et al., *Molec. & Cell. Biol.* 3:2271–2279, 1983), respectively. To determine whether P19 cells expressed endogenous neuroD genes during neuronal differentiation, RNA expression was analyzed for neuroD1, neuroD2, and neuroD3 in both uninduced and induced P19 cells. To induce the formation of neurons, P19 cells were cultured as aggregates in Petri dishes in the presence of retinoic acid for four days. The aggregates were then plated into tissue culture dishes in the absence of retinoic acid and neuronal differentiation occurred during a five day period, as evidenced by the formation of neurofilament positive process bearing cells.

NeuroD1 mRNA was most abundant after the cells were aggregated and treated with RA for 4 days, and continued to be expressed at decreased levels during the period of neuronal differentiation. NeuroD2 was not detected during the period of RA induction, but became abundant during the period of neuronal differentiation.

Both neuroD1 and neuroD2 signals were modestly enhanced when the differentiated P19 cultures were grown in the presence of Ara-C which eliminates some of the non-neuronal dividing cells, suggesting that the neuroD1 and neuroD2 genes are preferentially expressed in the post-mitotic cell population. NeuroD3 was first detected after two days of induction, and was most abundant after 4 days of induction), however, unlike neuroD1, neuroD3 mRNA was not detected at the later, more differentiated, time points. Therefore, the temporal expression pattern of neuroD1, neuroD2, and neuroD3 in differentiating P19 cells was similar to that seen during embryonic development: a peak of neuroD3 expression at the time of neuronal commitment and early neurogenesis, early and persistent expression of neuroD1, and slightly later and persistent expression of neuroD2. Hence, P19 cells are potentially useful in screening assays for identifying inducers of neuroD1 expression that may stimulate nerve regeneration and differentiation of neural tumor cells.

NeuroD1 and neuroD2 are both expressed in neurons and both can induce neurogenesis when expressed in frog embryos. To determine if they have the ability to activate similar target genes, expression vectors were constructed driving the human neuroD1 or neuroD2 coding regions from a simian cytomegalovirus promoter; these vectors are pCS2-hND1 and pCS2-hND2, whose construction is described in Example 10. The activity of neuroD1 and neuroD2 was assayed on reporter constructs co-transfected into P19 cells. Other members of the neuroD family have been shown to bind consensus E-box sequences in vitro. Gel shift assays have demonstrated that MATH-1 and NEX-1/MATH-2 bind the consensus E-box site CAGGTG as a heterodimer with the E47 protein, and activate the transcription of reporter constructs (Akazawa et al., *J. Biol. Chem.*, 270:8730–8738, 1995; Bartholoma and Nave, 1994; Shimizu et al., *Eur. J. Biochem.*, 229:239–248, 1995). In vitro gel shift assays demonstrated that neuroD1 and neuroD2 proteins can bind to an oligo containing the core E-box CACCTG as a heterodimer with an E-protein. Therefore, neuroD1 and neuroD2 proteins were tested for the ability to activate transcription of the reporter construct P4RTK-luc, which is composed of a multimerized E-box with the same core sequence and the minimal promoter from the thymidine kinase gene driving the reporter gene luciferase.

Prior to transfection, P19 cells were cultured in minimal essential medium alpha supplemented with 10% fetal bovine serum. Transfections were performed as previously described (Tamura, M. and M. Noda, *J. Cell Biol* 126: 7731994), using BBS calcium chloride precipitation. Forty-eight hours after transfection, the cells were harvested and assayed for luciferase and lacZ. Construction of the expression vectors pCS2-hND1 and pCS2-hND2 were as described in Example 10. The pGAP43-luc construct, a neuronal specific promoter construct that is upregulated in vivo in post-mitotic, terminally differentiating neurons (Nedivi et al., *J. Neurosci.* 12:691–704, 1992), contained the 760 base pair promoter region driving luciferase in a pGL2 vector modified to contain a poly-A site upstream of the multiple cloning site. The p4RTK-luc construct was made by placing the 4RTK region from HindIII to XhoI of the p4RTK-CAT vector (Weintraub et al., *Proc. Natl. Acad. Sci.* 87:5623–5627, 1990) into the promoterless luciferase vector. Luciferase assays were performed according to Current Protocols in Molecular Biology (Brasier, A. R., John Wiley & Sons, New York, 1989, which is hereby incorporated by reference).

When P19 cells were transfected as described above, it was observed that cotransfection with either pCS2-ND1 or pCS2-ND2 modestly increased the level of activity from p4RTK-luc in P19 cells between two and four-fold.

Additional reporter constructs were tested in P19 cells to determine whether the neuroD and neuroD2 proteins had different transcriptional activation potentials. Tests were conducted to determine the ability of pCS2-ND1 and pCS2-ND2 to transactivate the luciferase reporter construct, pGAP43-luciferase. In contrast to the simple E-box driven reporter, pCS2-ND1 did not show significant transactivation of the pGAP43-luciferase, while pCS2-ND2 induced expression from this construct by approximately 4-fold over the basal activity.

The myogenic bHLH proteins show auto- and cross-regulation, and expression of NEX-1/MATH-2 has been shown to activate a reporter driven by the NEX-1/MATH-2 promoter (Bartholoma and Nave, 1994). To determine if neuroD1 or neuroD2 could activate a construct containing the neuroD2 promoter, an expression vector was constructed that contained a one kilobase fragment upstream of the mouse neuroD2 gene, terminating in the first exon, driving the luciferase reporter gene. P19 cells were co-transfected with this pND2-luc reporter construct and either of the neuroD expression vectors. Both pCS2-ND1 and pCS2-ND2 transactivated this reporter construct, suggesting that neuroD2 may be auto-regulated and cross-regulated by other members of the neuroD family, in a manner analogous to the regulation of the myogenic bHLH genes.

Together these transfection experiments demonstrate that neuroD1 and neuroD2 proteins can both activate some target genes, such as a multimerized E-box reporter and the neuroD2 promoter; whereas the reporter construct driven by the GAP43 promoter seems to be preferentially activated by neuroD2.

EXAMPLE 16

In situ localization of neuroD1 and neuroD2 RNA in adult mouse brain

To address whether neuroD1 and neuroD2 were expressed in neurons in the adult mouse brain and whether they were expressed in the same cells, in situ hybridizations were performed using $^{35}$S-UTP labeled RNA probes. Sections of adult mouse brain were hybridized to anti-sense probes derived from the mouse neuroD1 and neuroD2 cDNA fragments using T3 and T7 generated transcripts for sense and anti-sense probes, and incorporating $^{35}$S-UTP label. Frozen 4–5 micron sagittal sections of adult mouse brain were cut, placed on Fisher SUPERFROST slides (Fisher Scientific, Tustin, CH), and frozen at −80° C. Hybridization to $^{35}$S-UTP labeled probes and autoradiography was performed according to Masters et al. (*J. Neurosci.* 14:5844–5857, 1994, which is hereby incorporated by reference). After washing to remove unhybridized probe, sections were coated with liquid photographic emulsion. After development of the emulsion, dark field optics illuminated the silver grains as white spots at magnification XI60.

In the cerebellum, neuroD1 was easily detected in the granule layer, whereas the neuroD2 signal was less intense in this region and was largely restricted to the region of the Purkinje cells. In contrast, the neuroD1 and neuroD2 signals in the pyramidal cells and dentate gyrus of the hippocampus were easily detected. The neuroD2 probe hybridized preferentially to the region of the Purkinje cell layer. These results demonstrate that neuroD1 and neuroD2 are expressed in neuronal populations in the mature nervous system, and that their relative level of expression varies among neuronal populations.

EXAMPLE 17

Neurogenic bHLH genes in human tumor specimens and in neuroectodermal tumor cell lines Northern blot analysis was used to evaluate expression of neuroD family members and hash1 in surgical specimens from 13 medulloblastomas, five supratentorial PNETs, six pediatric gliomas, and cell lines derived from 14 neuroectodermal tumors and three gliomas. For these analyses, RNA extraction, gel electrophoresis, transfer to membranes, and hybridization were carried out according to standard protocols (e.g., Sambrook et al.). Hybridization was conducted under stringent conditions in FBI buffer (described in Example 11). Hybridizations were incubated for a minimum of 5 hours at 65°–70° C., and filters were washed in 0.1×SSC, 0.1% SDS at 55°–63° C., depending on the probe. Probes were derived from regions outside the conserved HLH domains in order to avoid cross-hybridization among genes. None of the probes used in these experiments cross-reacted with RNA from other family members under these hybridization conditions. In situ hybridization analysis was used to confirm data obtained by Northern blot analysis, and to determine whether expression of these genes was ubiquitous in tumor cells.

Human tumor tissue samples were obtained at crainiotomy. Samples were either snap frozen in liquid nitrogen and stored at −80° C., or were placed in tissue culture medium, mechanically disassociated, filtered, and the cell pellet collected by centrifugation. The cell lines analyzed for expression of neurogenic bHLH genes are listed in Table 1. Cell lines were obtained from the American Type Culture Collection (ATCC) except for: NLF, NGP, and NMB, which were obtained from G. Brodeur, University of Pennsylvania, and UW228, T9AG and SNB 19, which were obtained from J. Silver and M. Berger, University of Washington. Y79, WERI, H209 and H82 cells were grown in RPMI 1640 (GIBCO) with 10% FBS (HYCLONE). The remainder were grown in Eagles MEM with Earle's BSS, 1x non-essential amino acids (GIBCO), 1 mM pyruvate (GIBCO) and 10% FBS or FCS.

90:5648–5652, 1993). None of the probes cross-reacted with RNA from other family members under the hybridization conditions used.

The results of Northern blot analyses are summarized in Table 1. In Table 1, "nd" indicates that the sample was not tested for expression in that sample. Because of the small size of the samples, it was not possible to assay all of the samples for all four genes in this study.

TABLE 1

NEUROD Genes and HASH1 in Medulloblastoma

| Patient | Age | Sex | Distant Metastasis | NEUROD1 | NEUROD2 | NEUROD3 | HASH1 |
|---|---|---|---|---|---|---|---|
| 1 | 5 | M | Yes | + | – | + | – |
| 2 | 7 | M | No | + | + | – | – |
| 3 | 9 | M | Yes | + | + | + | – |
| 4 | 10 | M | No | + | + | – | – |
| 5* | 10 | M | No | + | – | + | – |
| 6 | 1 | F | No | + | + | – | – |
| 7 | 7 | M | No | + | – | – | – |
| 8 | 13 | M | Yes | + | nd | + | – |
| 9 | 7 | F | Yes | nd | nd | + | – |
| 10 | 9 | M | No | + | + | nd | – |
| 11 | 8 | M | No | + | – | nd | – |
| 12 | 6 | M | No | + | – | nd | – |
| 13 | 3 | M | No | + | nd | nd | – |

*Atypical histology, tumor progressed early in treatment.

Total RNA was extracted from confluent cell lines and tissue specimens or cell pellets using TRIZOL reagent (GIBCO). Northern analysis was performed according to standard protocols with minor modifications (Bennahmias, S., American Biotech Lab 7(8):10–12, 1989; Chin, M. S. et al., J. Comparative Neurol. 349:389–400, 1994). Because amounts of the surgical specimens were limited, neuroD2 or neuroD3 expression was determined for some specimens on stripped membranes that had previously been used for hybridization with probes corresponding to neuroD1 or hash1 expression, respectively. To ensure that previously applied probes had been adequately removed from the stripped filters, the filters were reprobed only after negative results were obtained in a four-day exposure to x-ray film. Human neuroD1 messenger RNA was detected using either a full length 1.6 kB cDNA probe (SEQ ID NO:14), or an 800 base pair probe from a region to the 3' side of the bHLH domain, and which was isolated by Kpn digestion (Lee, J. E. et al., Science 268:836–844, 1995). The probe used to detect expression of human neuroD2 spanned 500 base pairs in the region 3' of the bHLH coding region and located between Pst I and Sac I excision sites (McCormick et al., Mol. Cell Biol. 16:5792–5800, 1996). The human neuroD3 probe spanned 800 base pairs from the Sma I to Pst I restriction sites of the clone SK20A1 (McCormick et al., 1996). Hash1 probes spanned the bHLH domain and were obtained using PCR primers 5'GTCACAAGTCAGCGCCCAAG 3' (SEQ ID NO:23) and 5'CGACGAGTAGGATGAGACCG 3' (SEQ ID NO:24). Hash1 findings were confirmed using a probe derived from a 0.9kb fragment isolated from a human fetal cDNA library (STRATAGENE) that was homologous to the published sequence in the 3' untranslated region of this cDNA (Ball et al., Proc. Natl. Acad. Sci. USA The results indicated that neuroD1 was expressed in all 12 medulloblastoma surgical specimens analyzed with this probe. Specimens 2, 3, 4, 6, and 10 also expressed neuroD2.

Nine of the surgical samples were analyzed for neuroD3 expression (samples 1–9 in Table 1). Of these, five expressed neuroD3. Four of the patients whose tumors expressed neuroD3 presented with disseminated disease, and the fifth (patient #5) developed clinical and radiographic progression in the three-week interval between tumor resection and initiation of radiation therapy. The association observed between neuroD3 expression and medulloblastoma dissemination was significant using the Fisher exact test. These observations suggested that the expression of neuroD3 in a medulloblastoma indicates an aggressive form of the tumor.

For conducting the in situ hybridizations, paraformaldehyde-fixed frozen tumor specimens were sectioned at 12 micron intervals then pretreated with 4% Proteinase K, acidic anhydride and 0.1% TRITON X-100 (neuroD1) or 4% Proteinase K and acidic anhydride (neuroD2 and neuroD3). In situ analysis was performed according to published procedure except that the concentration of NBT was reduced ten-fold for neuroD2 and neuroD3 assays (Schaeran-Wiemers and Gerfin-Moser, Histochem. 100:431–440, 1993, which is hereby incorporated by reference).

In situ hybridization using probes corresponding to neuroD1, neuroD2 and neuroD3 were conducted with medulloblastoma samples. When antisense probes were used robust staining was observed in the characteristically scant cytoplasm, whereas background hybridization obtained with sense probes was minimal. In tumors that expressed neuroD1, nearly all the cells were positive, a result consistent with the homogeneous nature of medulloblastomas. Expression of neuroD1 and neuroD3 in esthesioneuroblastoma samples, a rare type of neuroblastoma, when assayed by in situ analysis demonstrated patchy expression, suggesting that expression may be more heterogeneous in some types of neuroblatsoma tumors than in others.

Medulloblastoma samples probed with a human clone of hash1 (Ball et al., 1993) were uniformly negative when analyzed by Northern blot analysis. In contrast, three of five supratentorial PNETs expressed hash1. These results suggest that while medulloblastoma and cerebral PNETs are similar histologically, they probably derive from distinct progenitor cell populations, and they can be differentiated by analyzing tumor samples for hash1 expression.

Six pediatric gliomas, including cerebellar pilocytic astrocytoma, cerebral pilocytic astrocytoma, ependymoma and malignant astrocytoma specimens as well as three human glioma cell lines failed to express any of the neurogenic bHLH messenger RNAs when analyzed by Northern blot with probes corresponding to neuroD1, neuroD2, and neuroD3.

Cell lines derived from various neuroectodermal tumors were analyzed to further elucidate the patterns of neurogenic bHLH expression. Northern blot analysis was performed on 13 cell lines derived from tumors of presumed neuroectodermal origin. Consistent with the above-described analysis of patient samples, the metastatic medulloblastoma cell lines D283 and D341 expressed neuroD1 and neuroD3 (see Table 2). These observations suggest that co-detection of neuroD1 and neuroD3 expression products is a means of distinguishing medulloblastoma from other types of PNETs.

TABLE 2

NEUROD Genes and HASH1 in Cell Lines

| | NeuroD1 | NeuroD2 | NeuroD3 | Hash1 |
|---|---|---|---|---|
| Medulloblastoma: | | | | |
| D283 | + | – | + | – |
| D341 | + | – | + | – |
| UW228 | – | – | – | – |
| DAOY | – | – | – | – |
| Neuroblastoma: | | | | |
| SKN-SH | + | – | – | + |
| NLF | – | – | – | – |
| NGP | + | – | – | + |
| NMB | – | – | – | + |
| IMR32 | + | – | – | + |
| SKN-MC | – | – | – | – |
| Retinoblastoma: | | | | |
| Y79 | + | – | + | – |
| WERI | + | – | – | – |
| Small Cell Lung Cancer: | | | | |
| H82 | + | – | + | – |
| H209 | – | – | + | + |
| Glioma: | | | | |
| SNB 19 | – | – | – | – |
| T98G | – | nd | nd | – |
| SF767 | – | – | – | – |

While the medulloblastoma cell lines did not express hash1, a gene critical for sympathoadrenal lineage development, it is notable that the neuroblastoma cell lines SKN-SH, NGP, NMB and IMR 32 did express this gene. (Guillemot et al., *Cell* 75:463–476, 1993). A number of neuroblastoma cell lines, i.e., SKN-SH, NGP, and IMR32, coexpressed hash1 and neuroD1. NeuroD2 and neuroD3 expression was not detected in any of the neuroblastoma cell lines that were analyzed. These observations suggest that neuroblastoma can be distinguished from other types of brain tumors by the co-detection of hash1 and neuroD1 expression.

No neuroD mRNAs were detected by Northern blot analysis in DAOY and UW228 medulloblastoma cells or in NLF and SKN-MC neuroblastoma cells. However, these cell lines may express bHLH proteins other than those tested (e.g., atonal homologs), or expression in these cells may be below the limit of detection by Northern blot analysis.

Retinoblastoma cell lines also were analyzed by Northern blot analysis. These were observed to express neuroD genes but not hash1. Y79, a cell line derived from familial retinoblastoma, expressed neuroD1 and neuroD3. WERI, a spontaneous retinoblastoma cell, expressed neuroD1 but not any of the others for which expression was evaluated. NeuroD1 is expressed in developing and mature retina, but expression in normal retina of neuroD2 and neuroD3 has not been reported. Achaete-scute homologs are expressed in late but not early retinal progenitors (Jasoni et al., *Development* 120:769–783, 1994; Jasoni and Reh, *J. Comparative Neurol.* 369:319–327, 1996). These data suggest that the retinoblastomas from which Y79 and WERI cell lines were derived from early retinal progenitors.

The lineage from which small cell lung cancers arise remains controversial. This type of cancer cell expresses proteins that normally are found in the central nervous system. One aspect of small cell lung cancer is that the patient's body frequently develops an autoimmune reaction against the cancer cells, and the resulting self-antibodies may subsequently attack the brain itself. Two small cell lung cancer cell lines, H82 and H209, were analyzed by Northern blot as described above for bHLH gene expression. It was observed that H82 cells expressed neuroD1 and neuroD3, and H209 cells expressed hash1 and neuroD3 (see Table 2). Possible explanations for these observations are that neurogenic bHLH factors are expressed because these tumors arise from neuroendocrine cells, or that neuroD/achaete-scute genes are deregulated in these tumors, thus conferring them with a neuronal phenotype although they were derived from a nonneuronal lineage.

NeuroD2 was not expressed in any neuroectodermal tumor cell line tested. As several of the tumors analyzed had expressed neuroD2 (see Table 1), this result was unexpected. It is possible that none of the cell lines tested were derived from neuroD2-expressing tumors. Alternatively, neuroD2 expression might confer a growth disadvantage to cells so that they are selected against in culture.

From the foregoing it will be appreciated that, although specific embodiments of the invention have been described herein for purposes of illustration, various modification may be made without deviating from the spirit and scope of the invention.

The embodiments of the invention in which an exclusive property or privilege is claimed are defined as follows:

1. A method of classifying a human neuroectodermal tumor by analyzing a sample of a tumor comprising:
  measuring the expression of at least one basic helix loop helix gene in a sample of a tumor; and
  determining that the tumors belongs to a subclass of neuroectodermal tumor if the basic helix loop helix gene expressed in the sample corresponds to a predetermined profile of basic helix loop helix expression associated with the subclass of neuroectodermal tumors.

2. The method of claim 1, wherein the basic helix loop helix gene is selected from among the group consisting of neuroD1, neuroD2, and neuroD3.

3. The method of claim 1, wherein the expression of neuroD1, neuroD2, and neuroD3 genes is measured in the sample.

4. A method of classifying a human neuroectodermal tumor as a medulloblastoma by analyzing a sample of a neuroectodermal tumor comprising:
  measuring neuroD1 and neuroD3 expression in a sample of a neuroectodermal tumor; and
  determining that the neuroectodermal tumor is a medulloblastoma if both neuroD1 and neuroD3 expression are detected in the sample.

5. A method of prognosticating a human medulloblastoma by analyzing a sample of a human medulloblastoma comprising:
  measuring neuroD3 expression in a sample of a human medulloblastoma; and determining that the medulloblastoma is an aggressive medulloblastoma if neuroD3 expression is detected in the sample.

6. The method of claim 5, wherein the step of measuring neuroD3 expression comprises:

hybridizing, under stringent conditions, RNA from the sample with a nucleic acid probe corresponding to a non-conserved region of neuroD3 and that is capable of hybridizing under stringent conditions with the nucleotide sequence shown in SEQ ID NO:12; and determining that neuroD3 is expressed in the sample if duplexes between the RNA and the nucleic acid probe are detected in the product of the hybridization reaction.

* * * * *

UNITED STATES PATENT AND TRADEMARK OFFICE
CERTIFICATE OF CORRECTION

PATENT NO. : 5,795,723
DATED : August 18, 1998
INVENTOR(S) : S.J. Tapscott et al.

Page 1 of 2

It is certified that error appears in the above-identified patent and that said Letters Patent is hereby corrected as shown below:

COLUMN     LINE

On the title page:

| COLUMN | LINE | |
|---|---|---|
| [63] Pg. 1, col. 1 | Related U.S. App. Data | Text should read --Continuation-in-part of PCT/US96/17532, Oct. 30, 1996, which is a continuation-in-part of Ser. No. 552,142, Nov. 2, 1995, Pat. No. 5,695,995, which is a continuation-in-part of PCT/US95/05741, May 8, 1995, which is a continuation-in-part of Ser. No. 239,238, May 6, 1994, abandoned.-- |
| 8 | 30 | "11,13," should read --11, 13,-- |
| 11 | 25 | "SEQ ID NO:O10," should read --SEQ ID NO:10,-- |
| 23 | 61 | Before "α-tubulin" delete "(" |
| 23 | 62 | "Hermmati-Brinvanlou" should read -- Hemmati-Brinvanlo--. |
| 26 | 11 | "(ATCC:CRL 1729)" should read --(ATCC:CRL1729)-- |
| 29 | 46 | "20A 1" should read --20A1-- |
| 30 | 12 | "9F$_1$" should read --9F1-- |
| 33 | 60 | After "genomic" insert --fragment together with the-- |
| 35 | 44 | "MgCl$_2$," should read --MgCl$_2$,-- |

UNITED STATES PATENT AND TRADEMARK OFFICE
CERTIFICATE OF CORRECTION

PATENT NO. : 5,795,723
DATED : August 18, 1998
INVENTOR(S) : S.J. Tapscott et al.

It is certified that error appears in the above-identified patent and that said Letters Patent is hereby corrected as shown below:

| COLUMN | LINE | |
|---|---|---|
| 36 | 33 | After "differentiation." delete paragraph return |
| 38 | 23 | "XI60." should read --X160.-- |
| 39 | 2 | "SNB 19," should read --SNB19,-- |

Signed and Sealed this

Fifth Day of September, 2000

Attest:

Q. TODD DICKINSON

*Attesting Officer*　　*Director of Patents and Trademarks*